US006204246B1

(12) United States Patent
Bosch et al.

(10) Patent No.: US 6,204,246 B1
(45) Date of Patent: *Mar. 20, 2001

(54) HYBRID TOXIN

(75) Inventors: Hendrik Jan Bosch, Utrecht; Willem Johannes Stiekema, Wageningen, both of (NL)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/001,982

(22) Filed: Dec. 31, 1997

Related U.S. Application Data

(63) Continuation-in-part of application No. 08/602,737, filed as application No. PCT/EP94/02909 on Sep. 1, 1994, now Pat. No. 5,736,131.

(30) Foreign Application Priority Data

Sep. 2, 1993 (GB) .................................... 9318207

(51) Int. Cl.[7] .......................... A01N 37/18; C07K 14/325
(52) U.S. Cl. ................. 514/12; 514/2; 530/350; 530/825
(58) Field of Search ................. 530/350, 825; 514/12, 2

(56) References Cited

U.S. PATENT DOCUMENTS

| | | | |
|---|---|---|---|
| 5,508,264 | 4/1996 | Bradfish et al. | 514/12 |
| 5,593,881 | * 1/1997 | Thompson et al. | 435/418 |
| 5,736,131 | 4/1998 | Bosch et al. | 424/93.2 |

FOREIGN PATENT DOCUMENTS

| | | |
|---|---|---|
| 0228838 | 4/1992 | (EP) . |
| WO91/01087 | 2/1991 | (WO) . |
| WO95/30753 | 11/1995 | (WO) . |

OTHER PUBLICATIONS

Li et al. Crystal structure of delta–endotoxin from Bacillus thuringiensis at 2.5 Angstrom resolution. Nature 353: 815–821, Oct. 1991.*
De Maagd et al. Domain III substitution in Bacillus thuringiensis delta endotoxin CryIA(b) results in superior toxicity for *Spodoptera exigua* and altered membrane protein recognition. Applied and Environmental Microbiology 62: 1537–1543, May 1996.*
Honee et al., *Molecular Microbiology*, 5(11):2799–2806 (1991).
Nakamura et al., *Agric. Biol. Chem.*, 54(3):715–724 (1990).
Ge et al., *Proc. Nat. Acad. Sci.*, USA 86:4037–4041 (1989).
Bosch et al., *Bio/technology* 12:915–918 (1994).
Visser et al., Domain–function studies of *Bacillus thuringiensis* crystal proteins: a genetic approach in *Bacillus thuringiensis*, an environmental biopesticide: theory and practice. (eds, Entwistle et al.) Chicester: Wiley & Sons (1993).
Schnepf et al., *J. Biol. Chem.*, 265(34):20923–20930 (1990).
Raymond et al., *Mol. Microbiology* 4(11):1967–1973 (1990).

* cited by examiner

Primary Examiner—Karen Cochrane Carlson
Assistant Examiner—Gabriele E. Bugaisky
(74) Attorney, Agent, or Firm—J. Timothy Meigs

(57) ABSTRACT

The present invention provides, inter alia, a B.t. hybrid toxin fragment comprising at its C-terminus domain III of a first Cry protein, or a part of said domain or a protein substantially similar to said domain; and comprising at its N-terminus the N-terminal region of a second Cry protein, or a part of said region or a protein substantially similar to said region.

28 Claims, 7 Drawing Sheets

FIG. 6A

```
              1520       1530       1540       1550       1560       1570
                *          *          *          *          *          *
CRYIGTOX      AAAAGTCTGGCTCGTAACAATACCATTAATCCAGATAGAATTACACAGATACCATTGACG
              :::        :::  ::   :::::  :::  :::::::  :::::::   ::  :::::  ::    :
CRYICTOX      CGTAGTGCAACTCTTACAAATACAATTGATCCAGAGAGAATTAATCAAATACCTTTAGTG
                                              |         |                    |
Hybrid HK28-                                 -12        -1                  -24
```

FIG. 6B

```
                490        500        510        520        530
                 *          *     #    *          *          *
CRYIGTOX      GGLRQVASNRRSSLVMYGWTHKSLARNNTINPDRITQIPLTKVDTRGTGV
               :          :    ::: :    ::: :  :: :::: :             :
CRYICTOX      TG-----------VVFSWTHRSATLTNTIDPERINQIPLVKGFRVWGGT
                                      |   |     |
Hybrid HK28-                         -12  -1   -24
```

HYBRID TOXIN

This application is a continuation-in-part of application Ser. No. 08/602,737, filed Feb. 21, 1996 now U.S. Pat. No. 5,736,131, which is a 371 of international application no. PCT/EP94/02909, filed Sep. 1, 1994. Both of the aforementioned applications are incorporated herein by reference.

FIELD OF THE INVENTION

The present invention relates to hybrid toxin fragments, and toxins comprising them, derived from *Bacillus thuringiensis* insecticidal crystal proteins.

BACKGROUND OF THE INVENTION

*Bacillus thuringiensis* (hereinafter B.t.) is capable of producing proteins that accumulate intra-cellularly as crystals. These crystal proteins are toxic to a number of insect larvae. Based on sequence homology and insecticidal specificity, crystal proteins have been categorized into different classes. Best studied are the CryI class of proteins, which are produced as 140 kDa protoxins and are active towards lepidopterans.

To some extent, the mode of action of crystal proteins has been elucidated. After oral uptake, the crystals dissolve in the alkaline environment of the larval midgut. The solubilized proteins are subsequently processed by midgut proteinases to a proteinase-resistant toxic fragment of about 65 kDa, which binds to receptors on epithelial cells of the insect midgut and penetrates the cell membrane. This eventually leads to bursting of the cells and death of the larvae.

The activity spectrum of a particular crystal protein is to a large extent determined by the occurrence of receptors on the midgut epithelial cells of susceptible insects. The activity spectrum is co-determined by the efficiency of solubilization of the crystal protein and its proteolytic activation in vivo.

The importance of the binding of the crystal protein to midgut epithelial receptors is further demonstrated where insects have developed resistance to one of the crystal proteins, such that the binding of crystal proteins to midgut epithelial cells in resistant insects is significantly reduced.

Toxic fragments of crystal proteins are thought to be composed of three distinct structural domains. Domain I, the most N-terminal domain, consists of 7 a-helices. Domain II comprises 3 β-sheets. Domain III, the most C-terminal domain, folds into a β-sandwich. If projected on CryI sequences, domain I runs from about amino acid residues 28 to 260, domain II from about 260 to 460, and domain III from about 460 to 600.

DESCRIPTION OF THE INVENTION

The present invention concerns hybrid crystal proteins particularly, though not exclusively, involving CryIC together with CryIE, CryIA, or CryIG. The nucleotide sequence of the CryIC gene from B.t. sub. sp. entomocidus 60.5 is given in SEQ ID NO:1, and the corresponding amino acid sequence of the protein encoded by said nucleotide sequence is given in SEQ ID NO:2. The nucleotide sequence of the CryIE gene from B.t. sub. sp. kenyae 4FI is given in SEQ ID NO:3, and the corresponding amino acid sequence of the protein encoded by said nucleotide sequence is given in SEQ ID NO:4. The nucleotide sequence of a B.t. CryIG gene is given in SEQ ID NO:9, and the corresponding amino acid sequence of the protein encoded by said nucleotide sequence is given in SEQ ID NO:10. These proteins are toxic to lepidopterans, but within this order of insects, each protein has different specificity. CryIC, for example, is particularly active against *S. exigua* and *M. brassicae*.

According to the present invention, there is provided an isolated B.t. hybrid toxin fragment comprising at its C-terminus domain III of a first Cry protein, or a part of said domain or a protein substantially similar to said domain; and comprising at its N-terminus the N-terminal region of a second Cry protein, or a part of said region or a protein substantially similar to said region. For example, a preferred B.t. hybrid toxin fragment according to the present invention comprises at its C-terminus domain III of a first Cry protein and comprises at its N-terminus domains I and II of a second Cry protein. A preferred fragment is one that does not bind to the CryIC binding site in an insect gut when it comprises at its C-terminus domain III of CryIC, or a part of said domain or a protein substantially similar to said domain; or one that does not bind to a CryIA binding site when it comprises at its C-terminus domain III of CryIA, or a part of said domain or a protein substantially similar to said domain.

In the context of the present invention, "substantially similar" means a pure protein having an amino acid sequence that is at least 75% similar to the sequence of a protein according to the invention. It is preferred that the degree of similarity is at least 85%, more preferred that the degree of similarity is at least 90%, and still more preferred that the degree of similarity is at least 95%. In the context of the present invention, two amino acid sequences with at least 75%, 85%, 90%, or 95% similarity to each other have at least 75%, 85%, 90%, or 95% identical or conservatively replaced amino acid residues in a like position when aligned optimally allowing for up to 6 gaps, with the proviso that, with respect to the gaps, a total not more than 15 amino acid residues are affected. For the purpose of the present invention, conservative replacements may be made between amino acids within the following groups:

(i) Serine and Threonine;
(ii) Glutamic acid and Aspartic acid;
(iii) Arginine and Lysine;
(iv) Asparagine and Glutamine;
(v) Isoleucine, Leucine, Valine, and Methionine;
(vi) Phenylalanine, Tyrosine, and Tryptophan; and
(vii) Alanine and Glycine, with the proviso that in SEQ ID NO:6, Ser and Tyr are conservative replacements at position 620, and Ala and Glu are conservative replacements at position 618; and that in SEQ ID NO:8, Ser and Tyr are conservative replacements at position 627, and Ala and Glu are conservative replacements at position 625.

In the context of the present invention, "part" of a protein means a peptide comprised by said protein and having at least 80% of the consecutive sequence thereof.

In the context of the present invention, "binding site" means a site on a molecule wherein the binding between site and toxin is reversible such that the Ka between site and toxin is in the order of at least $10^4$ $dm^3 mole^{-1}$.

The toxin fragment may comprise at its N-terminus the N-terminal region of any insecticidal protein from B.t. being commonly known as "Cry" or "Cyt", including: CryIA(a), CryIA(b) CryIA(c), CryIB, CryIC, CryID, CryIE, CryIF, CryIG, CryIH, CryIIA, CryIIB, CryIIC, CryIIIA, CryIIIB, CryIIIB(b), CryIVA, CryIVB, CryIVC, CryIVD, CYTA, CryX1(IIIC), CryX2(IIID), CryX3, CryV, and CryX4, or a part of said region or a protein substantially similar to said region. The toxin fragment may comprise at its C-terminus domain III of CryIC, or a part of said domain or a protein substantially similar to said domain.

Thus, the fragment may comprise domain II of CryIE, CryIB, CryID, CryIA, or CryIG, or a part of said domain II or a protein substantially similar to said domain II, and domain III of CryIC or a part of said domain III or a protein substantially similar to said domain III. It is particularly preferred that the fragment comprises domains I and II of CryIE, CryIB, CryID, CryIA, or CryIG, or a part thereof or a protein substantially similar to said domains I and II, and domain III of CryIC or a part thereof or a protein substantially similar to said domain III.

It is most preferred that the toxin fragment comprises a region at its C-terminus comprising the sequence from amino acid position 454 to position 602 of CryIC, or a sequence substantially similar to said sequence. The fragment may comprise a region at its C-terminus comprising the sequence from amino acid position 478 to 602 of Cry IC, or a sequence substantially similar to said sequence, with the proviso that if the sequence comprising amino acids 478 to 602 of CryIC is fused directly to the C-terminus of domain II of CryIA, CryIB, CryID, CryIE, or CryIG, then the folding of the fusion product is satisfactory to yield an insecticidal component of the fragment. The routineer in the art will recognize that it may be necessary to add a peptide region to the C-terminus of domain II that spaces the C-terminal region of CryIC apart, thus enabling it to fold in such a way as to exhibit insecticidal activity.

It is most particularly preferred that the toxin fragment according to the invention comprises one of the following:
i) an amino acid sequence from about amino acid 1 to about amino acid 620 in SEQ ID NO:6, or an amino acid sequence from about amino acid 1 to about amino acid 620 in SEQ ID NO:6, wherein with respect to said sequence, at least one of the following alterations is present:
Ile at position 609 is replaced with Leu,
Ala at position 618 is replaced with Glu,
Ser at position 620 is replaced with Tyr;
ii) an amino acid sequence from about amino acid 1 to about amino acid 627 in SEQ ID NO:8, or an amino acid sequence from about amino acid 1 to about amino acid 627 in SEQ ID NO:8, wherein with respect to said sequence, at least one of the following alterations is present:
Ile at position 616 is replaced with Leu,
Ala at position 625 is replaced with Glu,
Ser at position 627 is replaced with Tyr; and
iii) an amino acid sequence from about amino acid 1 to about amino acid 602 in SEQ ID NO:12.

Whatever amino acid alterations are permitted, however, one or more of the following residues indicated sequence-wise with respect to the CryIC sequence is invariable: Phe (501), Val (478), Trp (479), and Thr (486).

The invention also includes a hybrid toxin comprising the above disclosed fragment or a toxin at least 85% similar to such a hybrid toxin, which has substantially similar insecticidal activity or receptor binding properties.

The invention still further includes pure proteins that are at least 90% similar to the toxin fragments or hybrid toxins according to the invention.

The invention still further includes recombinant DNA comprising a sequence encoding a protein comprising an amino acid sequence of one of the above-disclosed toxins or fragments thereof. The invention still further includes recombinant DNA comprising the sequence from about nucleotide 1 to about nucleotide 1860 given in SEQ ID NO:5, or DNA similar thereto encoding a substantially similar protein; or recombinant DNA comprising the sequence from about nucleotide 1 to about nucleotide 1881 in SEQ ID NO:7, or DNA similar thereto encoding a substantially similar protein; or recombinant DNA comprising the sequence from about nucleotide 1 to about nucleotide 1806 in SEQ ID NO:11, or DNA similar thereto encoding a substantially similar protein.

In the context of the present invention, "similar DNA" means a test sequence that is capable of hybridizing to the inventive recombinant sequence. When the test and inventive sequences are double stranded, the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably, the hybridization is performed under stringent conditions, with either the test or inventive DNA preferably being supported. Thus, either a denatured test or inventive sequence is preferably first bound to a support and hybridization is effected for a specified period of time at a temperature of between 50 and 70° C. in double strength citrate buffered saline containing 0.1% SDS, followed by rinsing of the support at the same temperature but with a buffer having a reduced SC concentration. Depending upon the degree of stringency required, and thus the degree of similarity of the sequences, such reduced concentration buffers are typically single strength SC containing 0.1% SDS, half strength SC containing 0.1% SDS and one tenth strength SC containing 0.1% SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1% SDS. Typical stringent conditions are as follows: hybridization at 7% sodium dodecyl sulfate (SDS), 0.5 M NaPO$_4$ pH 7.0, 1 mM EDTA at 50° C.; wash with 2×SSC, 1% SDS, at 50° C.

The recombinant DNA may further encode a protein having herbicide resistance, plant growth-promoting, anti-fungal, anti bacterial, anti-viral, and/or anti-nematode properties. In the case that the DNA is to be introduced into a heterologous organism, it may be modified to remove known mRNA instability motifs (such as AT rich regions) and polyadenylation signals, and/or codons that are preferred by the organism into which the recombinant DNA is to be inserted may be used so that expression of the thus modified DNA in the organism yields substantially similar protein to that obtained by expression of the unmodified recombinant DNA in the organism in which the protein components of the hybrid toxin or toxin fragments are endogenous.

The invention still further includes a DNA sequence complementary to one that hybridizes under stringent conditions with the recombinant DNA according to the invention.

Also included in the present invention are the following: a vector containing such a recombinant (or complementary thereto) DNA sequence; a plant or microorganism that includes and enables expression of such DNA; plants transformed with such DNA; the progeny of such plants that contain the DNA stably incorporated and hereditable in a Mendelian manner; and/or the seeds of such plants and such progeny.

The invention still further includes protein derived from expression of the recombinant DNA of the invention, and insecticidal protein produced by expression of the recombinant DNA within plants transformed therewith.

The invention still further includes the following: an insecticidal composition containing one or more of the toxin fragments or toxins comprising them according to the invention; a process for combating insects that comprises exposing them to such fragments or toxins or compositions; and an extraction process for obtaining insecticidal proteins from organic material containing them, comprising submitting the material to maceration and solvent extraction.

DESCRIPTION OF THE FIGURES

FIG. 6A shows the alignment of the cry1G and cry1C genes with the crossover points of the cry1G/cry1C hybrids. The position relative to the first nucleotide of the start codon of cry1G is shown.

FIG. 6B shows the alignment of the encoded Cry1G and Cry1C proteins with the crossover points of the Cry1G/Cry1C hybrids. The approximate position of the domain II–III border is indicated by #. The position relative to the initiation codon of Cry1G is also indicated.

DESCRIPTION OF THE SEQUENCES IN THE SEQUENCE LISTING

Figure 1:
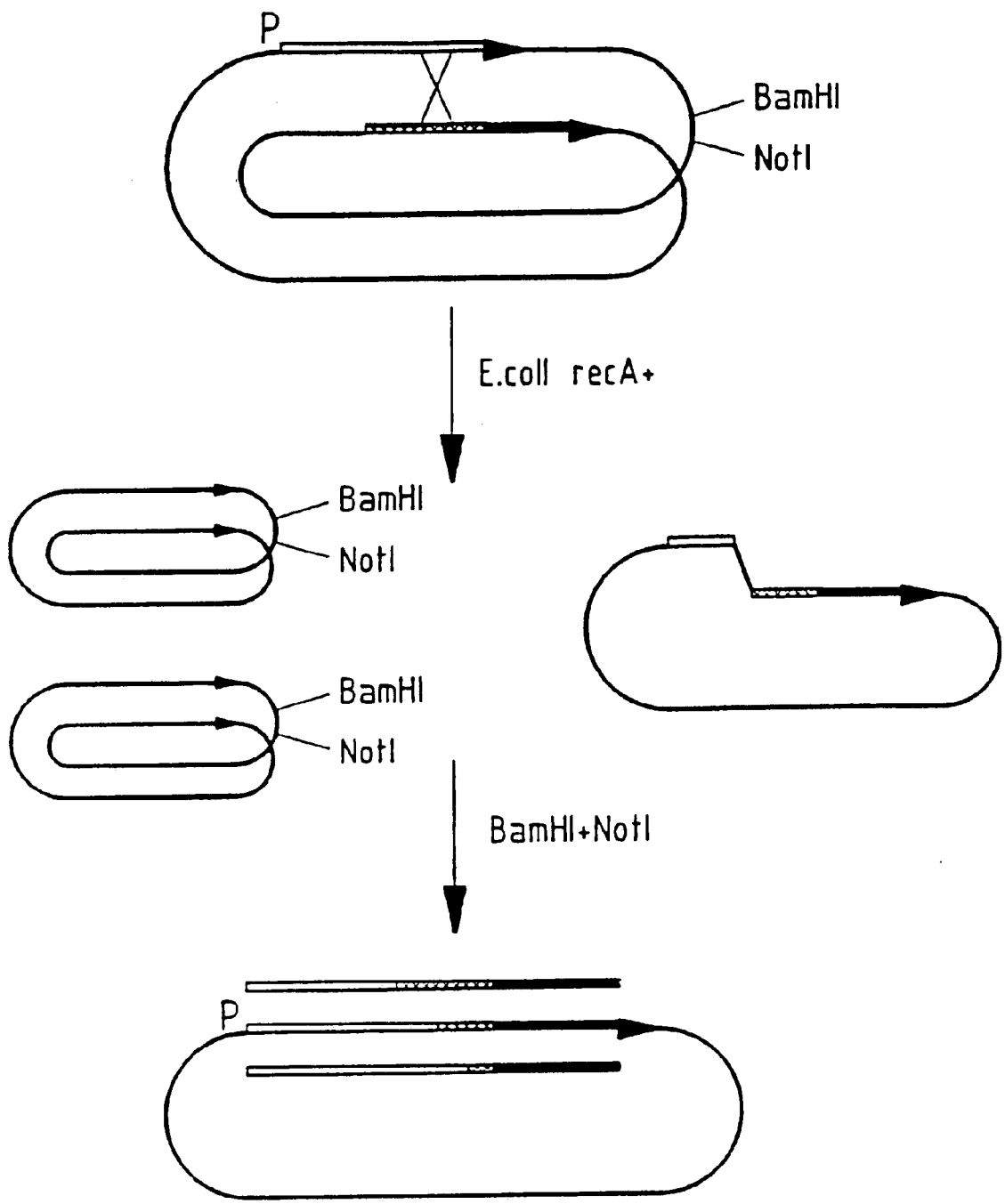
FIG. 1 shows the generation of hybrid crystal protein genes via in vivo recombination. Tandem plasmids (pBD560 and pBD 650) carrying two truncated crystal protein genes in direct repeat orientation are constructed. The 5' located gene (open bar) lacks the protoxin encoding region (solid bar) and of the 3' located gene (dashed bar) part of the domain I encoding region is deleted. In vivo recombination between homologous regions (domain II and III) occurs in recA+ strain JM101. Selection against non-recombinants by digestion with NotI and BamHI and subsequent transformation results in sets of plasmids encoding hybrid crystal proteins.

SEQ ID NO:1 shows the nucleotide sequence of the CryIC gene from B.t. sub. sp. entomocidus 60.5.

SEQ ID NO:2 shows the amino acid sequence of the protein encoded by the CryIC gene shown in SEQ ID NO:1.

SEQ ID NO:3 shows the nucleotide sequence of the CryIE gene from B.t. sub. sp. kenyae 4FI.

SEQ ID NO:4 shows the amino acid sequence of the protein encoded by the CryIE gene shown in SEQ ID NO:3.

SEQ ID NO:5 shows the nucleotide sequence encoding a preferred CryIE/CryIC B.t. hybrid toxin fragment according to the invention.

SEQ ID NO:6 shows the amino acid sequence of the protein encoded by the nucleotide sequence shown in SEQ ID NO:5.

SEQ ID NO:7 shows the nucleotide sequence of a CryIA/CryIC hybrid toxin fragment according to the invention.

SEQ ID NO:8 shows the amino acid sequence of the protein encoded by the nucleotide sequence depicted in SEQ ID NO:7.

SEQ ID NO:9 shows the nucleotide sequence of a B.t. CryIG gene.

SEQ ID NO:10 shows the amino acid sequence of the protein encoded by the CryIG gene shown in SEQ ID NO:9.

SEQ ID NO:11 shows the nucleotide sequence encoding a preferred CryIG/CryIC B.t. hybrid toxin fragment (hybrid HK28-24) according to the invention.

SEQ ID NO:12 shows the amino acid sequence of the protein encoded by the nucleotide sequence shown in SEQ ID NO:12.

SEQ ID NOs:13–15 are oligonucleotides.

The invention will be further apparent from the following non-limiting Examples, which describe the production of B.t. hybrid toxin fragments according to the invention, taken in conjunction with the associated Figures and Sequence Listing.

EXAMPLES

Production of Plasmids Encoding Hybrid Toxin Fragments

In the production of plasmids carrying the CryIC or CryIE genes, *Escherichia coli* XLI-blue (Stratagene Inc.) is used as plasmid host except in cases were JM101 is used as recA+ background. A vector for the expression of crystal proteins in *E. coli* is derived from pKK233-2 (Pharmacia LKB Biotechnology). The size of pKK233-2 is reduced by deleting an EcoRI-PvuII fragment carrying the gene encoding tetracycline resistance. Subsequently a 6 bp XhoI linker is ligated into the HindIII site resulting in pBD10. Plasmid BK+ is created by insertion of a BglII linker in the SacI site of Bluescript SK+ (Stratagene Inc.). The polylinker of BK+ from BglII to XhoI is introduced between the NcoI-XhoI site in pBD10. The resulting expression vector pBD11 contains the highly expressed trc promoter, the lacZ ribosome binding site and ATG initiation codon. The initiation codon overlaps with a NcoI site and is followed by the polylinker to facilitate insertions into the vector. Transcription is terminated by the rrnB transcription terminator.

The cloning of the cryIC and cryIE genes from B.t. sub. sp. entomocidus 60.5 and kenya 4F1 respectively is as described previously (Honée et al., 1990 (Appl. Environ. Microbiol. 56, pp. 823–825); Visser et al., 1990 (J. Bacteriol. 172, pp. 6783–6788)). For cloning purposes, an NcoI site overlapping with the start codon of cryIC is created by in vitro mutagenesis. A BglII site is created directly downstream of the translation termination codon of cryIC by site directed mutagenesis, resulting in the sequence ATAA GATCTGTT (SEQ ID NO:13—stop-codon underlined). The NcoI-BglII fragment containing the cryIC coding region is ligated into pBD11, resulting in CryIC expression plasmid pBD150. pBD155 is a derivative of pBD150, in which the polylinker sequences 3' of cryIC are deleted.

A DraI fragment from pEM 14 (Visser et al., 1990) containing the complete cryIE gene is cloned in the EcoRV site of SK+, resulting in plasmid pEM15. Subsequently, an NcoI site is introduced by site directed mutagenesis at the start codon of the gene, and cryIE is transferred as an NcoI-XhoI fragment to pBD11, resulting in CryIE expression plasmid pBD160.

Plasmids carrying only toxic fragment-encoding regions of the cryI genes are constructed. BglII linkers are ligated to XmnI sites present at bp position 1835 of cryIC, and to the HgiAI site at position 1839 of cryIE. Subsequently, NcoI-BglII fragments containing the cryIC (1835 bp) and cryIE (1839 bp) toxic fragment-encoding regions are ligated into pBD11, resulting in pBD151 and pBD161 respectively as described below.

Tandem plasmids used for the generation of cryIC-cryIE hybrid genes are constructed as follows: BamHI linkers are ligated to pBD160 digested with HpaI. This DNA is incubated with BamHI and XhoI and the truncated cryIE gene running from bp 704 is ligated into pBD151 resulting in pBD560. To construct a tandem plasmid for the generation of cryIE-cryIC hybrids, pBD155 is digested with NsiI and XhoI. The fragment carrying the truncated cryIC gene, running from bp 266, is ligated into PstI/XhoI digested pBD161, resulting in plasmid pBD650. Due to polylinker sequences, unique NotI and BamH1 restriction sites are present between the truncated cryI genes present in the tandem plasmids pBD560 and pBD650.

DNA Manipulations and Construction of Hybrid Toxins

All recombinant DNA techniques are as described by Sambrook et al. 1989 (in "Molecular Cloning, A Laboratory Manual: Cold Spring Harbour Press, Cold Spring Harbour). DNA sequencing is performed by the dideoxytriphosphate method with fluorescent dyes attached to the dideoxynucleotides. Analysis is automated by using an Applied Biosystems 370A nucleotide sequence analyzer.

Figure 2:
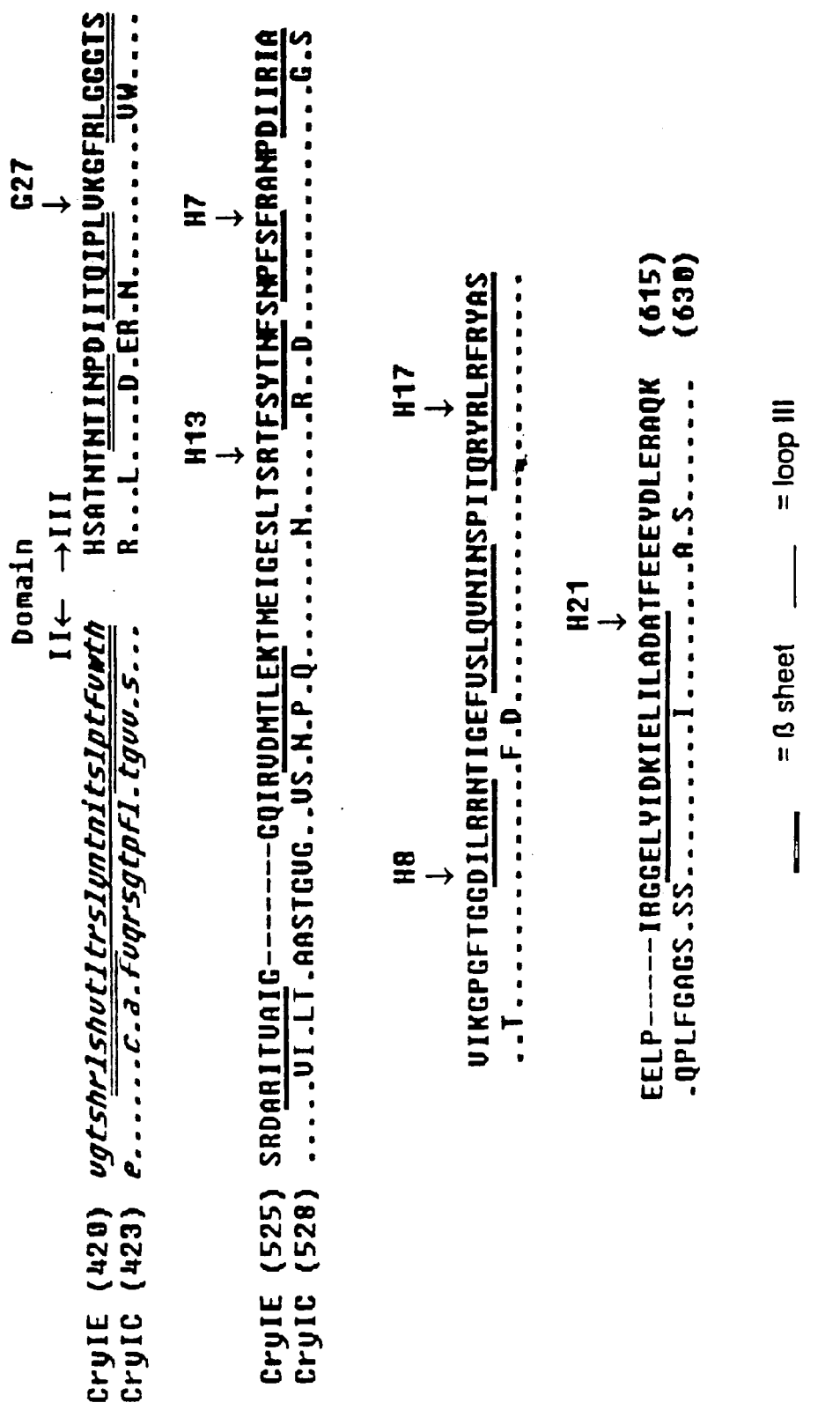
FIG. 2 shows the alignment of amino acid residues 420 to 630 of CryIE and CryIC. The border between domain II and III is indicated. Only amino acid residues of CryIC that differ from CryIE are depicted; identical residues are indicated by dots. The crossover positions (G27, H13, H7, H8, H17, and H21) in the CryIE/CryIC hybrid toxin fragments according to the invention are indicated on the Figure.

The homology present between cryI genes permits intramolecular recombination in vivo. Two tandem plasmids are created, each carrying two truncated crystal protein genes overlapping only in domains II and III. Therefore, recombination occurs only in regions encoding domains II and III. In-frame recombinations, which can be selected for by restriction enzyme digestion, generate plasmids that express full size 140 kDa hybrid protoxins. To generate in vivo recombinants, a tandem plasmid (either pBD560 or pBD650; FIG. 2) is transferred to JM101. 5 mg of DNA is isolated from independently generated recombinants and is digested with NotI and BamHI cutting between the two truncated cryI genes to select against non-recombinants, and the DNA is transformed to E. coli XL1-blue. 5 single colonies are grown and protein patterns and plasmid content are analyzed.

CryIC/CryIE and CryIE/CryIC hybrid toxins are generated using the tandem plasmids pBD560 and pBD650 respectively, which are allowed to recombine in a recA+ background. DNA is isolated, digested, and transferred to recA-strain as described above.

100 colonies of 20 independent experiments are analyzed on SDS-PAGE. 85% of these clones produce a 140 kDa protein indicating in frame recombinations between cryIC and cryIE, and cryIE and cryIC, respectively. In E. coli, CryI proteins are produced as crystals that can be solubilized in vitro at high pH. Approximately 15% of hybrid toxins produced as above are solubilized at high pH. The recombinants producing soluble hybrid toxins are first classified using restriction enzymes. Subsequently, for each class, the crossover point of selected hybrids is determined by DNA sequence analysis. All crossovers resulting in soluble hybrid toxins occur in or very close to domain III.

Protein Purification and Analysis

Crystal proteins are isolated essentially as described by Convents et al. (J. Biol. Chem. 265, pp. 1369–1375; Eur. J. Biochem., 195, pp. 631–635). Briefly, recombinant E. coli are grown at 30° C. in 250 ml TB medium to an $OD_{660}$ of 10–15. Crystals isolated from the E.coli lysate are solubilized during incubation for 2 hours in 20 mM $Na_2CO_3$, 10 mM dithiothreitol, 100 mM NaCl, pH10, at 37° C. The pH of the solution is lowered to 8 with Tris-HCl and incubated with trypsin. The toxin solution is dialysed against 20 mM Tris-HCl, 100 mM, NaCl pH9. Subsequently, the toxic fragment is purified on a Mono Q 5/5 column connected to a fast-protein liquid chromatography (FPLC) system (Pharmacia LKB Biotechnology). Proteins are separated by 7.5% sodium dodecyl sulfate-polyacrylamide gel electrophoreses.

Biochemical Analysis and Isolation of 65 kDa Toxic Fragments

Isolated crystals of purified CryIC, CryIE, and the hybrid proteins are solubilized at high pH and incubated with trypsin. Like CryIC and CryIE, all soluble hybrid toxins with crossovers in domain III are converted to stable 65 kDa fragments. The 65 kDa fragments can be purified using anion exchange chromatography under similar conditions as the parental proteins. Hybrids F59 and F71, which have crossovers in domain II, are completely degraded by trypsin. Apparently, although these hybrids do not precipitate as insoluble aggregates, trypsin cleavage sites buried in the parental proteins may become exposed to trypsin. Because of this phenomenon, no 65 kDa fragments are isolated from F59 and F71.

Table 1 shows the constitution of 5 CryIE/CryIC hybrid toxins: (G27, H8, H17, H13, H7, and H21) and 4 CryIC/CryIE hybrid toxins (F59, F71, F26, and E7) with reference to the CryIC and CryIE proteins from which they are derived. The amino acid sequences of the CryIE/CryIC toxins comprising the toxic fragments of the present invention run to amino acid 1189 of the CryIC parent protein. The amino acid sequences of the CryIC/CryIE hybrid toxins run to amino acid 1171 of the CryIE parent protein. Table 1 also shows the relative insecticidal effectiveness of these various hybrid toxins with respect to the CryIC and CryIE proteins.

TABLE 1

| Toxin | aa IE | aa IC | M. sexta | S. exigua | M. brassicae |
|---|---|---|---|---|---|
| IC | 0 | 28–627 | + + | + + | + + |
| IE | 29–612 | 0 | + + | — | — |
| G27 | 1–474 | 478–627 | + + | + + (+) | + (+) |
| H8 | 1–497 | 501—627 | + + | — | — |
| H17 | 1–529 | 533–627 | + + | — | — |
| H7 | 1–577 | 588–627 | — | — | — |
| H21 | 1–605 | 621–627 | | | |
| F59 | 421–612 | 1–423 | — | — | — |
| F71 | 428–612 | 1–430 | — | — | — |

TABLE 1-continued

| Toxin | aa IE | aa IC | M. sexta | S. exigua | M. brassicae |
|---|---|---|---|---|---|
| F26 | 455–612 (1171) | 1–458 | + + | — | — |
| E7 | 588-612 (1171) | 1-602 | + + | + + | + + |

Table 1. Constitution and toxicity of hybrid toxins with respect to the parent proteins. Most bioassays were performed with purified toxin fragments. In case of CryIC these run from about aa 28 to about aa 627, and in case of CryIE till 612. The length of complete protoxins is indicated between brackets.

Insect Toxicity Assays and Insecticidal Activity of cryIC/cryIE Hybrid Gene Products Bacterial cultures are concentrated to $OD_{660}$ 6.0, and 100 ml are spotted on 2 cm$^2$ of artificial diet in a 24-well tissue culture plate. Alternatively, diluted samples of purified toxins are applied to the diet. Second instar larvae of either *S. exigua, M. brassicae*, or *M. sexta* are fed on this diet (16 per sample dilution) for 5 days, after which the larval weight is scored. The relative growth (EC50, the concentration giving 50% growth reduction) is determined by calculating the ratio between the mean weight of larvae grown on diet supplemented with toxin and the mean weight of control larvae grown on a diet without toxin. *M. sexta* egg layers are supplied by Carolina Biological Supply Company, North Carolina, USA.

The toxic fragments encoded by the hybrid gene products are tested for activity towards three different insect species as described above. *M. sexta* is susceptible to both CryIC and CryIE. As may be anticipated from their sensitivity to trypsin, hybrids F59 and F71 are not active against this insect (Table 1). Although H7 is converted by trypsin to stable 65 kDa proteins, it is not toxic to *M. sexta*. All of the other hybrids given in Table 1 are toxic and are apparently in the native, biologically active conformation.

The 65 kDa fragment of CryIC is highly toxic towards *S. exigua* and *M. brassicae*, whereas CryIE is not. G27 (Table 1; FIG. 2), a CryIE-CryIC hybrid with a crossover at the junction of domain II and III is active towards both insects. This demonstrates that domain III of CryIC confers full activity towards *S. exigua* and *M. biassicae*. Hybrid H8, which differs in only three amino acid residues (see FIG. 3) from G27, although active against *M. sexta*, is not active against *S. exigua* and *M. brassicae*.

Figure 3:
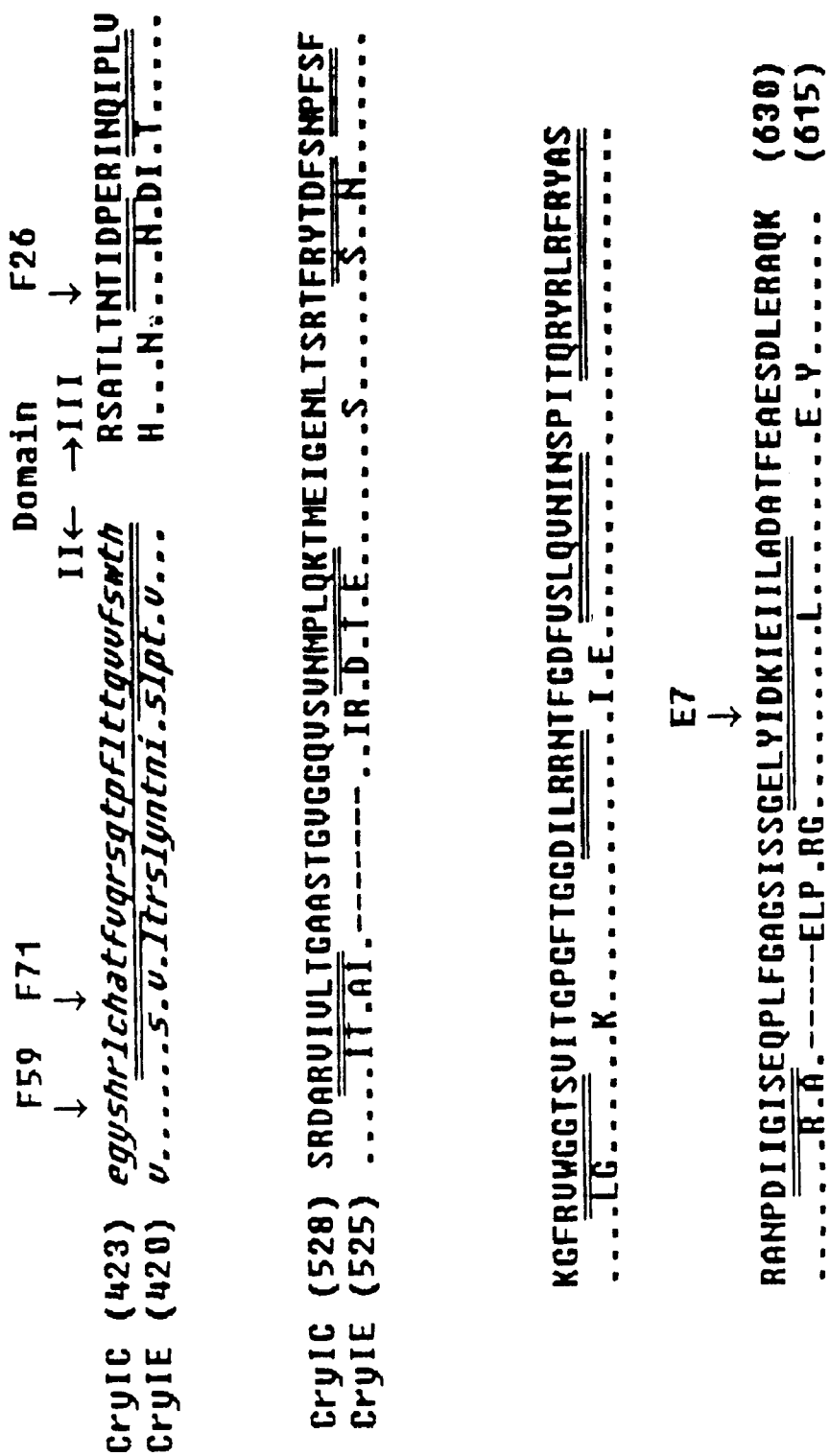
FIG. 3 shows the alignment of amino acid residues 420 to 630 of CryIE and CryIC. The border between domain II and III is indicated. Only amino acid residues of CryIC that differ from CryIE are depicted; identical residues are indicated by dots. The crossover positions (F59, F71, F26, and E7) in the CryIC/CryIE hybrid toxin fragments are indicated on the Figure.

F26 (Table 1; FIG. 3), the reciprocal hybrid of G27, in which domain III of CryIC has been exchanged by domain III of CryIE, is not active against *S. exigua* or *M. brassicae*. Apparently, although the protein is toxic to *M. sexta*, the CryIC sequences running from amino acid 28–462 are not sufficient to kill *S. exigua* and *M. brassicae*. Only when CryIC sequences up to amino acid residue 602 are present in the hybrid (E7) is insecticidal activity against these insects restored.

The present disclosure indicates that amino acid residues from 478–602 of CryIC can confer high insecticidal activity to CryIE against *S. exigua* and *M. brassicae*.

Biotinylation of Crystal Proteins and Binding Assays

Biotinylation is performed using biotin-N-hydroxysuccinimide ester essentially as described by the manufacturer (Amersham). 1 mg of crystal protein is incubated with 40 ml biotinylation reagent in 50 mM $NaHCO_3$, 150 mM NaCl, pH8, for one hour at 20° C. The solution is loaded on a Sephadex 25 column equilibrated with the same buffer containing 0.1% BSA to remove unbound biotin, and samples of the fractions are spotted on a nitrocellulose membrane. Fractions containing biotinylated crystal proteins are visualized using streptavidine-peroxidase conjugate (Amersham) which catalyzes the oxidation of luminol, resulting in chemiluminescence (ECL, Amersham), and pooled.

Brush border membrane vesicles are isolated as described by Wolfersberger et al. (1987) (Comp. Biochem. Physiol. 86a, pp. 301–308) except that the vesicles are washed once more with isolation buffer containing 0.1% Tween 20. Binding of biotinylated crystal proteins to brush border membrane vesicles (100 mg/ml) is performed in 100 ml of PBS containing 1% BSA, 0.1% Tween-20 (pH 7.6). Vesicles (20 μg vesicle protein) are incubated with 10 ng biotinylated crystal proteins in the presence or absence of 1000-fold excess of unlabelled crystal proteins for 1 hour at 20° C. Subsequently, the vesicles are re-isolated by centrifugation for 10 minutes at 14,000 g in an Eppendorf centrifuge, washed twice with binding buffer, re-suspended in sample buffer, denatured by heating, and loaded on 7.5% polyacrylamide gels. After electrophoresis, proteins are blotted to nitrocellulose membranes and biotinylated crystal proteins that are re-isolated with the vesicles are visualized by incubation of the nitrocellulose with streptavidin-peroxidase conjugate (Amersham), which catalyzes the oxidation of luminol, resulting in chemiluminescence (ECL, Amersham).

Figure 4:
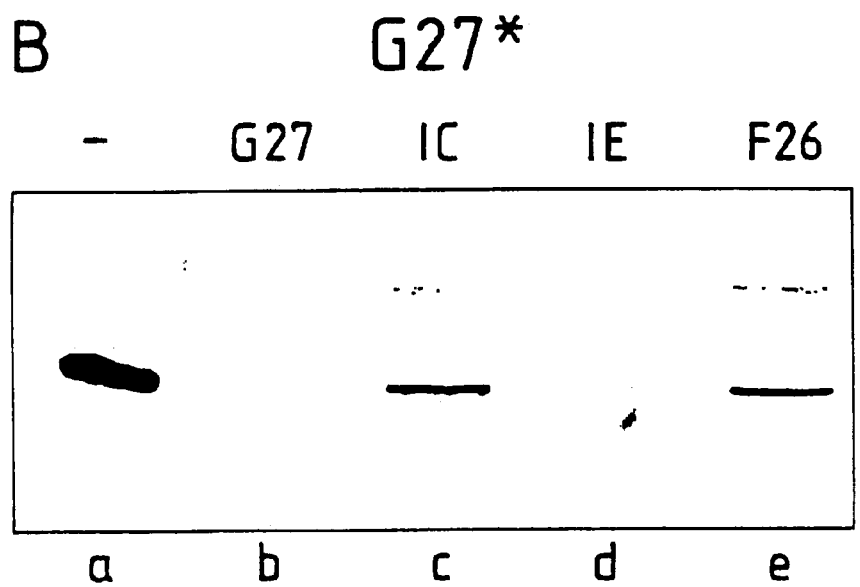
FIGS. 4A & 4B show the results of heterologous competition experiments. Biotinylated CryIC (panel 4A) and G27 (panel 4B) are incubated with S. exigua BBMV vesicles in the absence (lanes a) or presence of an excess of unlabelled protein as indicated. After the incubation, the vesicles are washed, loaded on a SDS-polyacrylamide gel and blotted to a nitrocellulose membrane. Biotinylated crystal proteins, re-isolated with the vesicles, are visualized using streptavidin-peroxidase conjugate and are indicated on the Figure with an arrow head.
Figure 4:
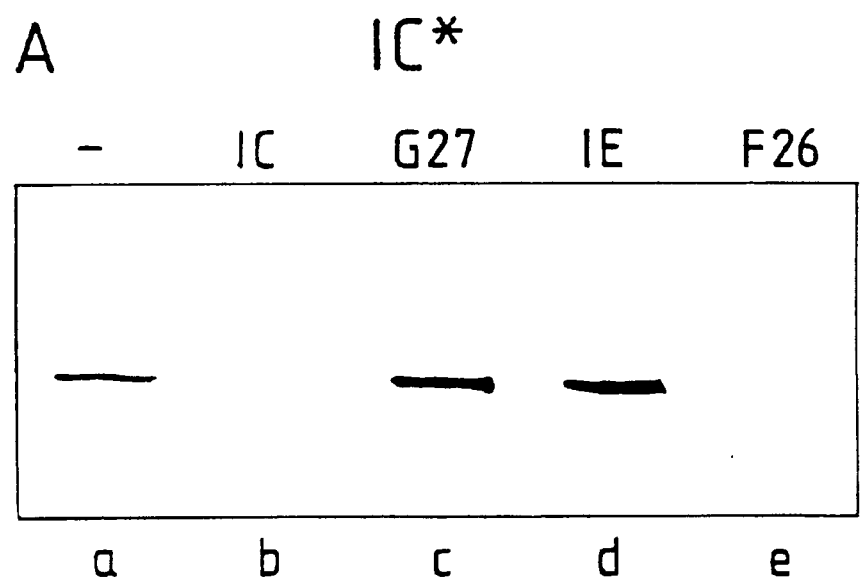

Because binding to epithelial gut cells is a key step in the mode of action of crystal proteins, the binding of crystal proteins to *S. exigua* brush border membrane vesicles is investigated in heterologous competition experiments. Competition experiments demonstrate that the binding of labeled CryIC (FIG. 4A, lane a) and labeled F26 (not shown) can be outcompeted by an excess of both unlabelled CryIC (lane b) or F26 (lane e) but not with an excess of G27 (lane c) or CryIE (lane d). Furthermore, binding of labeled G27 (FIG. 4B, lane a) and labeled CryIE (not shown) can be outcompeted by an excess of G27 (lane b) or CryIE (lane d), but not with an excess of CryIC (lane a) or F26 (lane e). From these results, it is concluded that G27 and CryIE recognize the same binding sites on *S. exigua* midgut membranes and that these sites differ from those that are recognized by CryIC and F26. The toxicity and binding assays combined demonstrate that G27 is as toxic as CryIC but that it binds a receptor different therefrom. As insects can develop resistance against a crystal protein by changing receptor binding characteristics, G27 may be used in resistance management programs as an alternative to CryIC.

Expression of cryIE/cryIC Hybrid Toxin Genes in Heterologous Systems

The G27 cryIE/cryIC hybrid toxin gene is expressed in *E.coli*, and the gene product exhibits at least the same insecticidal activity (at least against Spodoptera) as CryIC. Moreover, the product exhibits an increase in such activity when expressed in a *Bacillus thuringiensis* strain (see below). The gene encoding the G27 hybrid toxin is introduced into a suitable shuttle vector system, which is then introduced into an appropriate B.t. host. Such transformed cells are then cultured, and the resulting toxin from both whole cultures and purified crystals is assayed for insecticidal activity.

Figure 5:
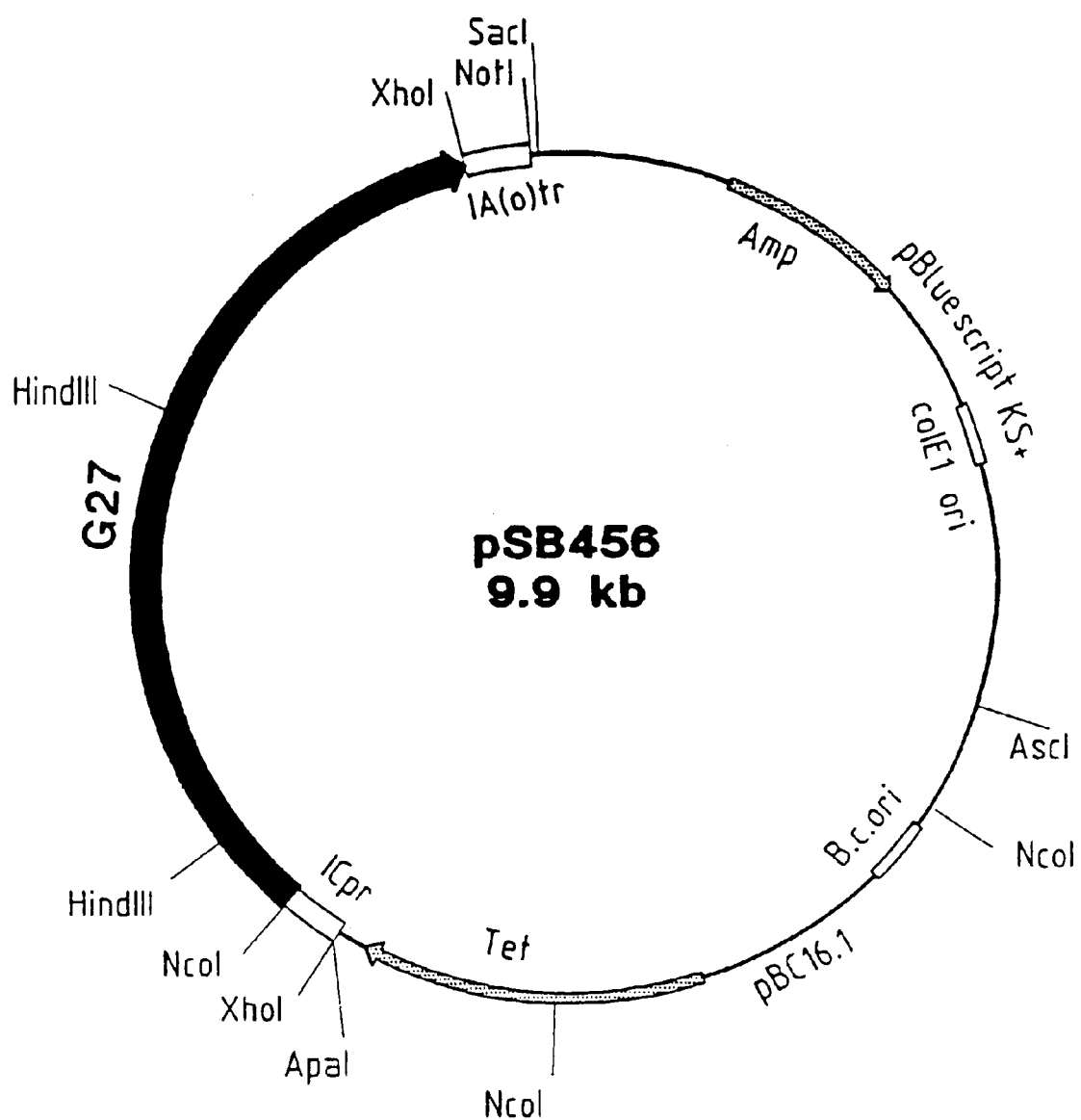
FIG. 5 shows the plasmid map of pSB456, which encodes the G27 hybrid toxin fragment and is used to transform the crystal toxin minus strain B.t. 51.

Construction of a G27-Containing Shuttle Vector, Transformation of Bt51, and Purification of Toxin Protein Therefrom The gene encoding hybrid G27 (3.4 kb) is cleaved from a pKK233 *E. coli* expression plasmid using NcoI and XhoI. The XhoI site is filled in using the Klenow fragment of *E. coli* DNA Polymerase I. The resulting fragment is ligated to NcoI/SmaI-digested pSB635 (pBluescriptKS+, $P_{cryIC}$, and the CryIA(c) transcription terminator). The resulting plasmid, pSB453, is digested with ApaI and NotI, yielding a 4.2 kbp fragment carrying the promoter, the hybrid G27 ORF, and the terminator. This fragment is ligated to ApaI/NotI-digested pSB634 (shuttle vector containing pBC16.1 and pBluescriptKS+), yielding pSB456 (see FIG. 5). Plasmid DNA isolated from *E. coli* DH10B is used to transform the crystal toxin minus B.t. strain, Bt51. Positive isolates are tetracycline resistant, show the presence of pSB456, and contain large inclusions corresponding to a 135 kDa protein (as determined by SDS-PAGE). G27 hybrid toxin samples are prepared from cultures of transformed Bt51 grown through sporulation at 30° C. in CYS-Tc$^{10}$ media. Insecticidal bioassays (Table 2) are performed on both full whole cultures and on washed crystal protein preparations. Controls include Bt51 (pSB440) containing the CryIC toxin and Bt5I (pSB636) containing CryIE. Toxin concentrations are estimated by SDS-PAGE.

TABLE 2

| Toxin | LC$_{50}$ | | | | |
|---|---|---|---|---|---|
| | Whole Culture (ppt) | | Washed Crystal Protein (ppm) | | |
| CryIC | 56(2) | 36(2) | 40(4) | 7.8(2) | 8.1(4) |
| CryIE | 79(1) | 78(1) | 33(4) | 11.1(6) | 7.5(4) |
| G27 | 29(2) | 21(2) | 25(4) | 4.7(4) | 6.0(4) |
| Ratio (IC/G27) | 1.93 | 1.71 | 1.60 | 1.66 | 1.35 |

Table 2. Bioassay of the hybrid toxin G27 in comparison to CryIC and CryIE. The number of samples is given in parentheses. The hybrid toxin G27 is about 50% more effective than either CryIE or CryIC with respect to toxicity to Spodoptera sp.

Production and Selection of Cry1G/Cry1C Hybrid Toxins

To obtain Cry1G/Cry1C hybrid toxins by in vivo recombination, expression vector pHK26 was constructed with a C-terminal truncated cryIG (a.k.a. Cry9A) gene (see, SEQ ID NO:9) and a N-terminal truncated cryIC gene (see, SEQ ID NO:1) cloned in tandem. The plasmid pHK26 contains the trc promoter followed by bases 1–1650 of cryIG, part of the pBluescript SK+ polylinker, and bases 266–3570 of cryIC. pHK26 is a derivative of pRM7 in which the cry1A(b) coding sequences from NcoI to BglII have been replaced by part of the cry1G gene. The 1650 bp NcoI-BglII cry1G fragment was isolated by PCR amplification from plasmid pSB 1501 using the primers dGCTAGCCATGGATCAAAATAAACACGGAATTATTG (SEQ ID NO:14) and dCTGGTCAGATCTTTGAAGTA-GAGCTCC (SEQ ID NO:15). After allowing intramolecular recombination of pHK26 in *E. coli* strain JM101, plasmid DNA was isolated and digested with BamHI and PinAI to linearize non-recombinant plasmids. Both BamHI as well as PinAI have unique recognition sites in pHK26, in the polylinker and at position 1074 of cryIC, respectively. The overlap between the two truncated cry genes in pHK26 that allows recombination extends approximately 1400 base pairs, yet primary interest was in recombinations in or close to domain III. Therefore, PinAI was chosen rather than a second enzyme with a recognition site in the polylinker. This strategy allowed linearization of recombinants with crossovers in front of the PinAI site, thereby effectively selecting for recombinants with crossovers in or near the domain III-encoding sequences.

Digested plasmids were transferred to *E. coli* XL1 cells by transformation, and plasmids from transformants were subsequently analyzed by restriction enzyme digestion and DNA electrophoresis. Over 80% of the transformants contained a plasmid with an insert size corresponding to a single, intact cry gene, indicating that selection for homologous recombination events had been efficient. Thirty separate colonies were grown in TB medium and assayed for production of alkaline-soluble protoxins that could be converted to stable 65 kD toxic fragments upon trypsin incubation. This screening method yielded 6 colonies producing a stable 65 kD toxic fragment of the expected size. The location of the crossovers in the hybrid genes was first determined by restriction analysis and finally by nucleotide sequencing. Only three different crossover sites occurred in the 6 hybrid genes thus tested. The hybrid genes were designated HK28-12, HK28-1, and HK28-24. The location of the three different crossover sites is shown in FIGS. 6A and 6B. The three crossovers are located close to the border between domains II and III, with the three hybrid toxins, designated HK28-12, HK28-1, and HK28-24, differing only one amino acid from each other. Both the solubility of the hybrid protoxins as well as the occurrence of trypsin-resistant products of the expected size suggested that these hybrids proteins were properly folded and might have biological activity. This was subsequently tested against larvae of *Spodoptera exigua*.

Toxicity of CryIG/CryIC Hybrid Toxins Towards *Spodoptera exigua*

Figure 7:
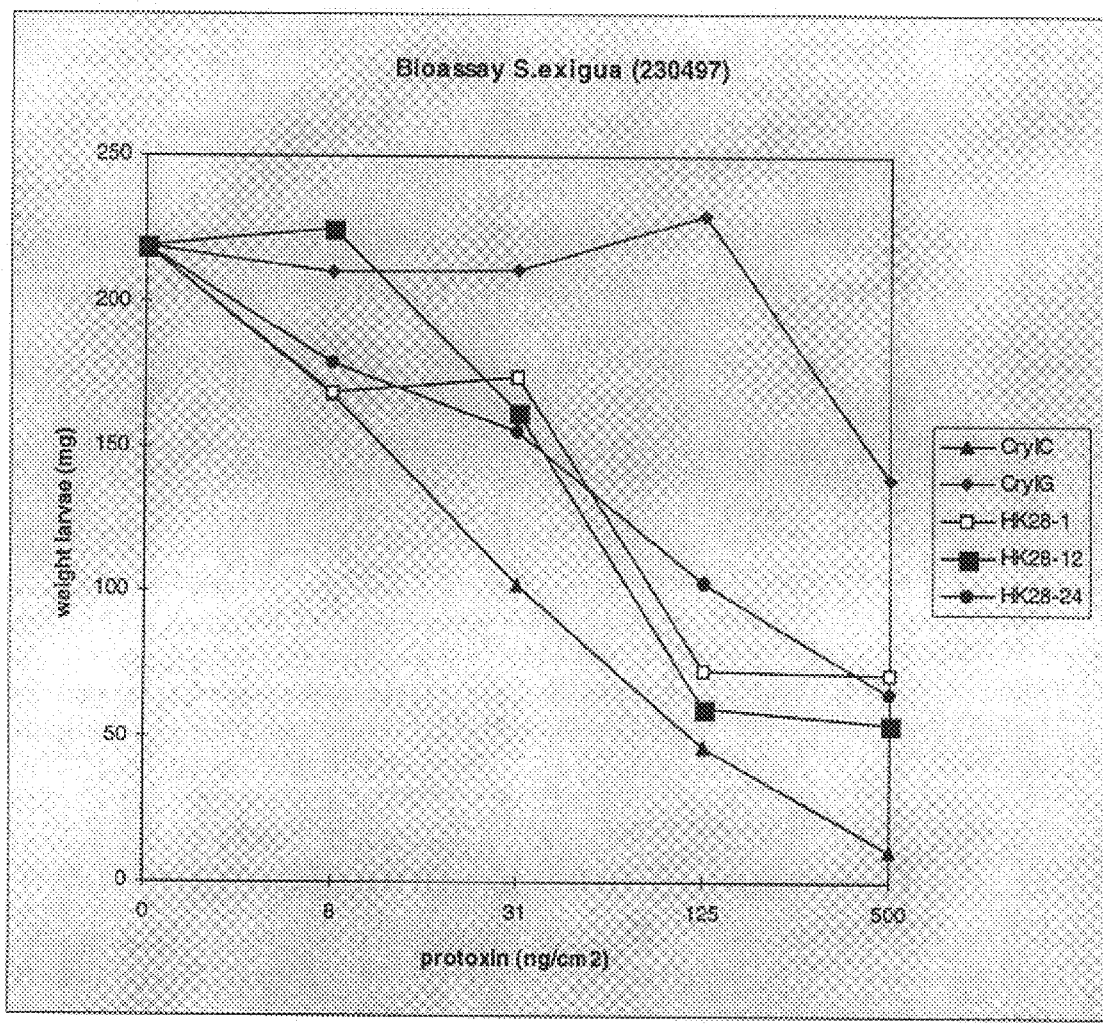
FIG. 7 shows the results of assays measuring the toxicity of Cry1G/Cry1C hybrid toxins towards *Spodoptera exigua*.

The cryIC, cryIG, and newly isolated cryIG/cryIC hybrid genes were introduced in *E. coli* strain XL1-blue and grown for 48 hours at 28° C. in TB medium with ampicillin. Cells were disrupted by sonification, and protoxin-containing crystals were isolated by cetrifugation. After washing the crystals, the protoxins were solubilized at high pH and the concentration of the 140 kD protoxins in the supernatant was estimated by SDS-PAGE. These samples were assayed for their toxicity to *S. exigua* larvae. Results are shown in FIG. 7.

CryIG protoxin is much less toxic to *S. exigua* than CryIC. The hybrids containing domain III of CryIC are significantly more toxic than Cry1G. These results show that, as was demonstrated earlier for CryIE and Cry1A(b), Cry1G can be made considerably more toxic to *S. exigua* by substituting its domain III with that of CryIC. For example, hybrid HK28-24 (SEQ ID NO:12) is much more toxic to *S. exigua* than Cry1G (SEQ ID NO:10). Hybrid HK28-24 is also much more toxic to *S. frugiperda* than Cry1G (data not shown).

Although the present invention has been particularly described with reference to the production of Cry1E/Cry1C and Cry1G/Cry1C hybrid toxins, the routineer in the art will appreciate that many other hybrid toxins having improved insecticidal characteristics may be produced according to the present disclosure. SEQ ID NOs:7 and 8, for example, depict the nucleotide and amino acid sequences, respectively, of a CryIA/CryIC hybrid toxin fragment according to the invention that has improved insecticidal activity. Hybrid toxins may be produced comprising domain III of CryIC and the N-terminal region, including domains I and II, of any other Cry protein. In terms of bioassays, the hybrid toxin-carrying transformants may be grown in SOP media to expedite the assay procedures and reduce the volumes of material required. Moreover, the genes encoding the Cry1E/Cry1C, Cry1G/Cry1C, Cry1A/Cry1C, and/or other hybrid toxins according to the invention may be transferred into toxin-encoding strains of B.t. and/or integrated into the chromosome of selected strains of B.t. or introduced into plant genomes to provide for insecticidal activity in situ within the plant per se. In this regard, it is particularly preferred that the recombinant DNA encoding the toxins is modified so that codons that are preferred by the plant into which the recombinant DNA is to be inserted are used, whereby expression of the thus modified DNA in the plant yields substantially similar protein to that obtained by expression of the unmodified recombinant DNA in the organism in which the protein components of the hybrid toxin or toxin fragments are endogenous.

Isolation of Additional B.t. Toxin Genes Based on Sequence Similarity to Known B.t. Toxin Genes A library is plated at a density of approximately 8,000 pfu per 10 cm Petri dish, and filter lifts of the plaques are made after 7 hours growth at 37° C. The plaque lifts are probed with the cDNA set forth in SEQ ID NO:1, 3, or 9 labeled with 32P-dCTP by the random priming method by means of a PrimeTime kit (International Biotechnologies, Inc., New Haven, Conn.). Exemplary hybridization conditions are 7% sodium dodecyl sulfate (SDS), 0.5 M $NaPO_4$ pH 7.0, 1 mM EDTA at 50° C. After hybridization overnight, the filters are washed with 2×SSC, 1% SDS at 50° C. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.). This experimental protocol can be used by one of ordinary skill in the art to obtain B.t. toxin genes substantially similar to those set forth in the Sequence Listing.

What is claimed is:

1. An insecticidal *Bacillus thuringiensis* hybrid toxin fragment, comprising:
   a) at a C-terminus of said fragment, domain m of III first Cry protein; and
   b) at an N-terminus of said fragment, domains I and II of a second Cry protein different from the first Cry protein.

2. An insecticidal *Bacillus thuringiensis* hybrid toxin fragment according to claim 1, wherein said first Cry protein is CryIC.

3. An insecticidal *Bacillus thuringiensis* hybrid toxin fragment according to claim 1, wherein said second Cry protein is selected from the group consisting of CryIA, CryIE, and CryIG.

4. An insecticidal *Bacillus thuringiensis* hybrid toxin fragment according to claim 3, wherein said second Cry protein is CryIA.

5. An insecticidal *Bacillus thuringiensis* hybrid toxin fragment according to claim 3, wherein said second Cry protein is CryIE.

6. An insecticidal *Bacillus thuringiensis* hybrid toxin fragment according to claim 3, wherein said second protein is CryIG.

7. An insecticidal *Bacillus thuringiensis* hybrid toxin fragment according to claim 1, wherein said first Cry protein is CryIC, and wherein said second Cry protein is CryIA, CryIE, or CryIG.

8. An insecticidal *Bacillus thuringiensis* hybrid toxin fragment according to claim 1, wherein said C-terminus comprises the sequence from amino acid position 454 to position 602 of SEQ ID NO:2.

9. An insecticidal *Bacillus thuringiensis* hybrid toxin fragment according to claim 1, wherein said C-terminus comprises the sequence from amino acid position 478 to position 602 of SEQ ID NO:2.

10. An insecticidal *Bacillus thuringiensis* hybrid toxin fragment according to claim 1, comprising a sequence selected from the group consisting of:
    a) amino acids 1–620 of SEQ ID NO:6; and
    b) amino acids 1–620 of SEQ ID NO:6, wherein at least one of the following substitutions is present:
       Ile at position 609 is replaced with Leu,
       Ala at position 618 is replaced with Glu,
       Ser at position 620 is replaced with Tyr.

11. An insecticidal *Bacillus thuringiensis* hybrid toxin fragment according to claim 1, comprising a sequence selected from the group consisting of:
    a) amino acids 1–627 of SEQ ID NO:8; and
    b) amino acids 1–627 of SEQ ID NO:8, wherein at least one of the following substitutions is present:
       Ile at position 617 is replaced with Leu,
       Ala at position 625 is replaced with Glu,
       Ser at position 627 is replaced with Tyr.

12. An insecticidal *Bacillus thuringiensis* hybrid toxin fragment according to claim 1, comprising
    amino acids 1–602 of SEQ ID NO:12.

13. An insecticidal *Bacillus thuringiensis* hybrid toxin fragment according to claim 1, wherein said hybrid toxin fragment binds to a binding site in an insect gut that is different than the site bound by said first Cry protein.

14. An insecticidal composition comprising the hybrid toxin fragment of claim 1.

15. A process for controlling insects, comprising exposing them to the insecticidal composition of claim 14.

16. An insecticidal *Bacillus thuringiensis* hybrid toxin fragment, comprising amino acids 1–602 of SEQ ID NO:12.

17. An insecticidal *Bacillus thuringiensis* hybrid toxin fragment that has at least 95% sequence identity with, and has substantially the same insecticidal specificity and substantially the same insecticidal activity as the hybrid toxin fragment of claim 16.

18. A polypeptide comprising the hybrid toxin fragment of claim 1.

19. A process for controlling insects, comprising exposing them to the hybrid toxin fragment of claim 1.

20. A process for controlling insects, comprising exposing them to the hybrid toxin fragment of claim 2.

21. A process for controlling insects, comprising exposing them to the hybrid toxin fragment of claim 3.

22. A process for controlling insects, comprising exposing them to the hybrid toxin fragment of claim 7.

23. A process for controlling insects, comprising exposing them to the hybrid toxin fragment of claim 8.

24. A process for controlling insects, comprising exposing them to the hybrid toxin fragment of claim 9.

25. A process for controlling insects, comprising exposing them to the hybrid toxin fragment of claim 10.

26. A process for controlling insects, comprising exposing them to the hybrid toxin fragment of claim 11.

27. A process for controlling insects, comprising exposing them to the hybrid toxin fragment of claim 12.

28. A process for controlling insects, comprising exposing them to the polypeptide of claim 18.

\* \* \* \* \*

UNITED STATES PATENT AND TRADEMARK OFFICE
CERTIFICATE OF CORRECTION

PATENT NO. : 6,204,246 B1
DATED : March 20, 2001
INVENTOR(S) : Hendrik Jan Bosch et al.

It is certified that error appears in the above-identified patent and that said Letters Patent is hereby corrected as shown below:

Claim 1,
Line 3, "domain m of III first" should read -- domain III of a first --.

Signed and Sealed this

Thirteenth Day of November, 2001

Attest:

*Nicholas P. Godici*

Attesting Officer

NICHOLAS P. GODICI
Acting Director of the United States Patent and Trademark Office

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 3567 base pairs
      (B) TYPE: nucleic acid
      (C) STRANDEDNESS: single
      (D) TOPOLOGY: unknown (ii) MOLECULE TYPE: cDNA (iii) HYPOTHETICAL: NO (iii) ANTI-SENSE: NO (vi) ORIGINAL SOURCE:
      (A) ORGANISM: Bacillus thuringiensis (ix) FEATURE:
      (A) NAME/KEY: CDS
      (B) LOCATION: 1..3567

(xi) SEQUENCE DESCRIPTION: SEQ ID NO: 1:

```
ATG GAG GAA AAT AAT CAA AAT CAA TGC ATA CCT TAC AAT TGT TTA AGT        48
Met Glu Glu Asn Asn Gln Asn Gln Cys Ile Pro Tyr Asn Cys Leu Ser
 1               5                  10                  15

AAT CCT GAA GAA GTA CTT TTG GAT GGA GAA CGG ATA TCA ACT GGT AAT        96
Asn Pro Glu Glu Val Leu Leu Asp Gly Glu Arg Ile Ser Thr Gly Asn
                20                  25                  30

TCA TCA ATT GAT ATT TCT CTG TCA CTT GTT CAG TTT CTG GTA TCT AAC       144
Ser Ser Ile Asp Ile Ser Leu Ser Leu Val Gln Phe Leu Val Ser Asn
            35                  40                  45

TTT GTA CCA GGG GGA GGA TTT TTA GTT GGA TTA ATA GAT TTT GTA TGG       192
Phe Val Pro Gly Gly Gly Phe Leu Val Gly Leu Ile Asp Phe Val Trp
    50                  55                  60

GGA ATA GTT GGC CCT TCT CAA TGG GAT GCA TTT CTA GTA CAA ATT GAA       240
Gly Ile Val Gly Pro Ser Gln Trp Asp Ala Phe Leu Val Gln Ile Glu
65                  70                  75                  80

CAA TTA ATT AAT GAA AGA ATA GCT GAA TTT GCT AGG AAT GCT GCT ATT       288
Gln Leu Ile Asn Glu Arg Ile Ala Glu Phe Ala Arg Asn Ala Ala Ile
                85                  90                  95

GCT AAT TTA GAA GGA TTA GGA AAC AAT TTC AAT ATA TAT GTG GAA GCA       336
Ala Asn Leu Glu Gly Leu Gly Asn Asn Phe Asn Ile Tyr Val Glu Ala
               100                 105                 110

TTT AAA GAA TGG GAA GAA GAT CCT AAT AAT CCA GAA ACC AGG ACC AGA       384
Phe Lys Glu Trp Glu Glu Asp Pro Asn Asn Pro Glu Thr Arg Thr Arg
           115                 120                 125

GTA ATT GAT CGC TTT CGT ATA CTT GAT GGG CTA CTT GAA AGG GAC ATT       432
```

-continued

```
Val Ile Asp Arg Phe Arg Ile Leu Asp Gly Leu Leu Glu Arg Asp Ile
    130                 135                 140

CCT TCG TTT CGA ATT TCT GGA TTT GAA GTA CCC CTT TTA TCC GTT TAT          480
Pro Ser Phe Arg Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT          528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT          576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT          624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT          672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA          720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT          768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT          816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC          864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG          912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT          960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC         1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA         1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT         1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT         1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT         1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT         1248
Arg Gly Arg Gly Thr Val Asp Ser Leu Thr Glu Leu Pro Pro Glu Asp
                405                 410                 415

AAT AGT GTG CCA CCT CGC GAA GGA TAT AGT CAT CGT TTA TGT CAT GCA         1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA         1344
Thr Phe Val Gln Arg Ser Gly Thr Pro Phe Leu Thr Thr Gly Val Val
        435                 440                 445
```

```
TTT TCT TGG ACG CAT CGT AGT GCA ACT CTT ACA AAT ACA ATT GAT CCA      1392
Phe Ser Trp Thr His Arg Ser Ala Thr Leu Thr Asn Thr Ile Asp Pro
450                 455                 460

GAG AGA ATT AAT CAA ATA CCT TTA GTG AAA GGA TTT AGA GTT TGG GGG      1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT      1488
Gly Thr Ser Val Ile Thr Gly Pro Gly Phe Thr Gly Gly Asp Ile Leu
            485                 490                 495

CGA AGA AAT ACC TTT GGT GAT TTT GTA TCT CTA CAA GTC AAT ATT AAT      1536
Arg Arg Asn Thr Phe Gly Asp Phe Val Ser Leu Gln Val Asn Ile Asn
                500                 505                 510

TCA CCA ATT ACC CAA AGA TAC CGT TTA AGA TTT CGT TAC GCT TCC AGT      1584
Ser Pro Ile Thr Gln Arg Tyr Arg Leu Arg Phe Arg Tyr Ala Ser Ser
            515                 520                 525

AGG GAT GCA CGA GTT ATA GTA TTA ACA GGA GCG GCA TCC ACA GGA GTG      1632
Arg Asp Ala Arg Val Ile Val Leu Thr Gly Ala Ala Ser Thr Gly Val
530                 535                 540

GGA GGC CAA GTT AGT GTA AAT ATG CCT CTT CAG AAA ACT ATG GAA ATA      1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT      1728
Gly Glu Asn Leu Thr Ser Arg Thr Phe Arg Tyr Thr Asp Phe Ser Asn
            565                 570                 575

CCT TTT TCA TTT AGA GCT AAT CCA GAT ATA ATT GGG ATA AGT GAA CAA      1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT      1824
Pro Leu Phe Gly Ala Gly Ser Ile Ser Ser Gly Glu Leu Tyr Ile Asp
            595                 600                 605

AAA ATT GAA ATT ATT CTA GCA GAT GCA ACA TTT GAA GCA GAA TCT GAT      1872
Lys Ile Glu Ile Ile Leu Ala Asp Ala Thr Phe Glu Ala Glu Ser Asp
610                 615                 620

TTA GAA AGA GCA CAA AAG GCG GTG AAT GCC CTG TTT ACT TCT TCC AAT      1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA      1968
Gln Ile Gly Leu Lys Thr Asp Val Thr Asp Tyr His Ile Asp Gln Val
            645                 650                 655

TCC AAT TTA GTG GAT TGT TTA TCA GAT GAA TTT TGT CTG GAT GAA AAG      2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
            675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
690                 695                 700

GAC CGT GGC TGG AGA GGA AGT ACA GAT ATT ACC ATC CAA GGA GGA GAT      2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG      2208
Asp Val Phe Lys Glu Asn Tyr Val Thr Leu Pro Gly Thr Val Asp Glu
            725                 730                 735

TGC TAT CCA ACG TAT TTA TAT CAG AAA ATA GAT GAG TCG AAA TTA AAA      2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC      2304
Ala Tyr Thr Arg Tyr Glu Leu Arg Gly Tyr Ile Glu Asp Ser Gln Asp
            755                 760                 765
```

| | |
|---|---|
| TTA GAA ATC TAT TTG ATC CGT TAC AAT GCA AAA CAC GAA ATA GTA AAT<br>Leu Glu Ile Tyr Leu Ile Arg Tyr Asn Ala Lys His Glu Ile Val Asn<br>770 775 780 | 2352 |
| GTG CCA GGC ACG GGT TCC TTA TGG CCG CTT TCA GCC CAA AGT CCA ATC<br>Val Pro Gly Thr Gly Ser Leu Trp Pro Leu Ser Ala Gln Ser Pro Ile<br>785 790 795 800 | 2400 |
| GGA AAG TGT GGA GAA CCG AAT CGA TGC GCG CCA CAC CTT GAA TGG AAT<br>Gly Lys Cys Gly Glu Pro Asn Arg Cys Ala Pro His Leu Glu Trp Asn<br>805 810 815 | 2448 |
| CCT GAT CTA GAT TGT TCC TGC AGA GAC GGG GAA AAA TGT GCA CAT CAT<br>Pro Asp Leu Asp Cys Ser Cys Arg Asp Gly Glu Lys Cys Ala His His<br>820 825 830 | 2496 |
| TCC CAT CAT TTC ACC TTG GAT ATT GAT GTT GGA TGT ACA GAC TTA AAT<br>Ser His His Phe Thr Leu Asp Ile Asp Val Gly Cys Thr Asp Leu Asn<br>835 840 845 | 2544 |
| GAG GAC TTA GGT GTA TGG GTG ATA TTC AAG ATT AAG ACG CAA GAT GGC<br>Glu Asp Leu Gly Val Trp Val Ile Phe Lys Ile Lys Thr Gln Asp Gly<br>850 855 860 | 2592 |
| CAT GCA AGA CTA GGG AAT CTA GAG TTT CTC GAA GAG AAA CCA TTA TTA<br>His Ala Arg Leu Gly Asn Leu Glu Phe Leu Glu Glu Lys Pro Leu Leu<br>865 870 875 880 | 2640 |
| GGG GAA GCA CTA GCT CGT GTG AAA AGA GCG GAG AAG AAG TGG AGA GAC<br>Gly Glu Ala Leu Ala Arg Val Lys Arg Ala Glu Lys Lys Trp Arg Asp<br>885 890 895 | 2688 |
| AAA CGA GAG AAA CTG CAG TTG GAA ACA AAT ATT GTT TAT AAA GAG GCA<br>Lys Arg Glu Lys Leu Gln Leu Glu Thr Asn Ile Val Tyr Lys Glu Ala<br>900 905 910 | 2736 |
| AAA GAA TCT GTA GAT GCT TTA TTT GTA AAC TCT CAA TAT GAT AGA TTA<br>Lys Glu Ser Val Asp Ala Leu Phe Val Asn Ser Gln Tyr Asp Arg Leu<br>915 920 925 | 2784 |
| CAA GTG GAT ACG AAC ATC GCG ATG ATT CAT GCG GCA GAT AAA CGC GTT<br>Gln Val Asp Thr Asn Ile Ala Met Ile His Ala Ala Asp Lys Arg Val<br>930 935 940 | 2832 |
| CAT AGA ATC CGG GAA GCG TAT CTG CCA GAG TTG TCT GTG ATT CCA GGT<br>His Arg Ile Arg Glu Ala Tyr Leu Pro Glu Leu Ser Val Ile Pro Gly<br>945 950 955 960 | 2880 |
| GTC AAT GCG GCC ATT TTC GAA GAA TTA GAG GGA CGT ATT TTT ACA GCG<br>Val Asn Ala Ala Ile Phe Glu Glu Leu Glu Gly Arg Ile Phe Thr Ala<br>965 970 975 | 2928 |
| TAT TCC TTA TAT GAT GCG AGA AAT GTC ATT AAA AAT GGC GAT TTC AAT<br>Tyr Ser Leu Tyr Asp Ala Arg Asn Val Ile Lys Asn Gly Asp Phe Asn<br>980 985 990 | 2976 |
| AAT GGC TTA TTA TGC TGG AAC GTG AAA GGT CAT GTA GAT GTA GAA GAG<br>Asn Gly Leu Leu Cys Trp Asn Val Lys Gly His Val Asp Val Glu Glu<br>995 1000 1005 | 3024 |
| CAA AAC AAC CAC CGT TCG GTC CTT GTT ATC CCA GAA TGG GAG GCA GAA<br>Gln Asn Asn His Arg Ser Val Leu Val Ile Pro Glu Trp Glu Ala Glu<br>1010 1015 1020 | 3072 |
| GTG TCA CAA GAG GTT CGT GTC TGT CCA GGT CGT GGC TAT ATC CTT CGT<br>Val Ser Gln Glu Val Arg Val Cys Pro Gly Arg Gly Tyr Ile Leu Arg<br>1025 1030 1035 1040 | 3120 |
| GTC ACA GCA TAT AAA GAG GGA TAT GGA GAG GGC TGC GTA ACG ATC CAT<br>Val Thr Ala Tyr Lys Glu Gly Tyr Gly Glu Gly Cys Val Thr Ile His<br>1045 1050 1055 | 3168 |
| GAG ATC GAA GAC AAT ACA GAC GAA CTG AAA TTC AGC AAC TGT GTA GAA<br>Glu Ile Glu Asp Asn Thr Asp Glu Leu Lys Phe Ser Asn Cys Val Glu<br>1060 1065 1070 | 3216 |
| GAG GAA GTA TAT CCA AAC AAC ACA GTA ACG TGT AAT AAT TAT ACT GGG<br>Glu Glu Val Tyr Pro Asn Asn Thr Val Thr Cys Asn Asn Tyr Thr Gly | 3264 |

```
                1075              1080              1085
ACT CAA GAA GAA TAT GAG GGT ACG TAC ACT TCT CGT AAT CAA GGA TAT        3312
Thr Gln Glu Glu Tyr Glu Gly Thr Tyr Thr Ser Arg Asn Gln Gly Tyr
        1090              1095              1100

GAC GAA GCC TAT GGT AAT AAC CCT TCC GTA CCA GCT GAT TAC GCT TCA        3360
Asp Glu Ala Tyr Gly Asn Asn Pro Ser Val Pro Ala Asp Tyr Ala Ser
1105              1110              1115              1120

GTC TAT GAA GAA AAA TCG TAT ACA GAT GGA CGA AGA GAG AAT CCT TGT        3408
Val Tyr Glu Glu Lys Ser Tyr Thr Asp Gly Arg Arg Glu Asn Pro Cys
            1125              1130              1135

GAA TCT AAC AGA GGC TAT GGG GAT TAC ACA CCA CTA CCG GCT GGT TAT        3456
Glu Ser Asn Arg Gly Tyr Gly Asp Tyr Thr Pro Leu Pro Ala Gly Tyr
                1140              1145              1150

GTA ACA AAG GAT TTA GAG TAC TTC CCA GAG ACC GAT AAG GTA TGG ATT        3504
Val Thr Lys Asp Leu Glu Tyr Phe Pro Glu Thr Asp Lys Val Trp Ile
            1155              1160              1165

GAG ATC GGA GAA ACA GAA GGA ACA TTC ATC GTG GAT AGC GTG GAA TTA        3552
Glu Ile Gly Glu Thr Glu Gly Thr Phe Ile Val Asp Ser Val Glu Leu
        1170              1175              1180

CTC CTT ATG GAG GAA                                                    3567
Leu Leu Met Glu Glu
1185
```

(2) INFORMATION FOR SEQ ID NO: 2:

(i) SEQUENCE CHARACTERISTICS:
        (A) LENGTH: 1189 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
                20                  25                  30

Ser Ser Ile Asp Ile Ser Leu Ser Leu Val Gln Phe Leu Val Ser Asn
            35                  40                  45

Phe Val Pro Gly Gly Gly Phe Leu Val Gly Leu Ile Asp Phe Val Trp
        50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
                100                 105                 110

Phe Lys Glu Trp Glu Glu Asp Pro Asn Asn Pro Glu Thr Arg Thr Arg
            115                 120                 125

Val Ile Asp Arg Phe Arg Ile Leu Asp Gly Leu Leu Glu Arg Asp Ile
        130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
```

-continued

```
                195                 200                 205
Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620
```

-continued

```
Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
            645                 650                 655

Ser Asn Leu Val Asp Cys Leu Ser Asp Glu Phe Cys Leu Asp Glu Lys
        660                 665                 670

Arg Glu Leu Ser Glu Lys Val Lys His Ala Lys Arg Leu Ser Asp Glu
    675                 680                 685

Arg Asn Leu Leu Gln Asp Pro Asn Phe Arg Gly Ile Asn Arg Gln Pro
690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
            725                 730                 735

Cys Tyr Pro Thr Tyr Leu Tyr Gln Lys Ile Asp Glu Ser Lys Leu Lys
        740                 745                 750

Ala Tyr Thr Arg Tyr Glu Leu Arg Gly Tyr Ile Glu Asp Ser Gln Asp
    755                 760                 765

Leu Glu Ile Tyr Leu Ile Arg Tyr Asn Ala Lys His Glu Ile Val Asn
770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
            805                 810                 815

Pro Asp Leu Asp Cys Ser Cys Arg Asp Gly Glu Lys Cys Ala His His
        820                 825                 830

Ser His His Phe Thr Leu Asp Ile Asp Val Gly Cys Thr Asp Leu Asn
    835                 840                 845

Glu Asp Leu Gly Val Trp Val Ile Phe Lys Ile Lys Thr Gln Asp Gly
850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
            885                 890                 895

Lys Arg Glu Lys Leu Gln Leu Glu Thr Asn Ile Val Tyr Lys Glu Ala
        900                 905                 910

Lys Glu Ser Val Asp Ala Leu Phe Val Asn Ser Gln Tyr Asp Arg Leu
    915                 920                 925

Gln Val Asp Thr Asn Ile Ala Met Ile His Ala Ala Asp Lys Arg Val
930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
            965                 970                 975

Tyr Ser Leu Tyr Asp Ala Arg Asn Val Ile Lys Asn Gly Asp Phe Asn
        980                 985                 990

Asn Gly Leu Leu Cys Trp Asn Val Lys Gly His Val Asp Val Glu Glu
    995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040
```

-continued

```
Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO: 3:

(i) SEQUENCE CHARACTERISTICS:
- (A) LENGTH: 3513 base pairs
- (B) TYPE: nucleic acid
- (C) STRANDEDNESS: single
- (D) TOPOLOGY: unknown (ii) MOLECULE TYPE: cDNA (iii) HYPOTHETICAL: NO (iii) ANTI-SENSE: NO (vi) ORIGINAL SOURCE:
- (A) ORGANISM: Bacillus thuringiensis (ix) FEATURE:
- (A) NAME/KEY: CDS
- (B) LOCATION: 1..3513

(xi) SEQUENCE DESCRIPTION: SEQ ID NO: 3:

```
ATG GAG ATA GTG AAT AAT CAG AAT CAA TGC GTG CCT TAT AAT TGT TTA       48
Met Glu Ile Val Asn Asn Gln Asn Gln Cys Val Pro Tyr Asn Cys Leu
  1               5                  10                  15

AAT AAT CCT GAA AAT GAG ATA TTA GAT ATT GAA AGG TCA AAT AGT ACT       96
Asn Asn Pro Glu Asn Glu Ile Leu Asp Ile Glu Arg Ser Asn Ser Thr
            20                  25                  30

GTA GCA ACA AAC ATC GCC TTG GAG ATT AGT CGT CTG CTC GCT TCC GCA      144
Val Ala Thr Asn Ile Ala Leu Glu Ile Ser Arg Leu Leu Ala Ser Ala
        35                  40                  45

ACT CCA ATA GGG GGG ATT TTA TTA GGA TTG TTT GAT GCA ATA TGG GGG      192
Thr Pro Ile Gly Gly Ile Leu Leu Gly Leu Phe Asp Ala Ile Trp Gly
     50                  55                  60

TCT ATA GGC CCT TCA CAA TGG GAT TTA TTT TTA GAG CAA ATT GAG CTA      240
Ser Ile Gly Pro Ser Gln Trp Asp Leu Phe Leu Glu Gln Ile Glu Leu
 65                  70                  75                  80

TTG ATT GAC CAA AAA ATA GAG GAA TTC GCT AGA AAC CAG GCA ATT TCT      288
Leu Ile Asp Gln Lys Ile Glu Glu Phe Ala Arg Asn Gln Ala Ile Ser
                 85                  90                  95

AGA TTG GAA GGG ATA AGC AGT CTG TAC GGA ATT TAT ACA GAA GCT TTT      336
```

```
Arg Leu Glu Gly Ile Ser Ser Leu Tyr Gly Ile Tyr Thr Glu Ala Phe
        100                 105                 110

AGA GAG TGG GAA GCA GAT CCT ACT AAT CCA GCA TTA AAA GAA GAG ATG        384
Arg Glu Trp Glu Ala Asp Pro Thr Asn Pro Ala Leu Lys Glu Glu Met
        115                 120                 125

CGT ACT CAA TTT AAT GAC ATG AAC AGT ATT CTT GTA ACA GCT ATT CCT        432
Arg Thr Gln Phe Asn Asp Met Asn Ser Ile Leu Val Thr Ala Ile Pro
130                 135                 140

CTT TTT TCA GTT CAA AAT TAT CAA GTC CCA TTT TTA TCA GTA TAT GTT        480
Leu Phe Ser Val Gln Asn Tyr Gln Val Pro Phe Leu Ser Val Tyr Val
145                 150                 155                 160

CAA GCT GCA AAT TTA CAT TTA TCG GTT TTG AGA GAT GTT TCA GTG TTT        528
Gln Ala Ala Asn Leu His Leu Ser Val Leu Arg Asp Val Ser Val Phe
                165                 170                 175

GGG CAG GCT TGG GGA TTT GAT ATA GCA ACA ATA AAT AGT CGT TAT AAT        576
Gly Gln Ala Trp Gly Phe Asp Ile Ala Thr Ile Asn Ser Arg Tyr Asn
                180                 185                 190

GAT CTG ACT AGA CTT ATT CCT ATA TAT ACA GAT TAT GCT GTA CGC TGG        624
Asp Leu Thr Arg Leu Ile Pro Ile Tyr Thr Asp Tyr Ala Val Arg Trp
                195                 200                 205

TAC AAT ACG GGA TTA GAT CGC TTA CCA CGA ACT GGT GGG CTG CGA AAC        672
Tyr Asn Thr Gly Leu Asp Arg Leu Pro Arg Thr Gly Gly Leu Arg Asn
    210                 215                 220

TGG GCA AGA TTT AAT CAG TTT AGA AGA GAG TTA ACA ATA TCA GTA TTA        720
Trp Ala Arg Phe Asn Gln Phe Arg Arg Glu Leu Thr Ile Ser Val Leu
225                 230                 235                 240

GAT ATT ATT TCT TTT TTC AGA AAT TAC GAT TCT AGA TTA TAT CCA ATT        768
Asp Ile Ile Ser Phe Phe Arg Asn Tyr Asp Ser Arg Leu Tyr Pro Ile
                245                 250                 255

CCA ACA AGC TCC CAA TTA ACG CGG GAA GTA TAT ACA GAT CCG GTA ATT        816
Pro Thr Ser Ser Gln Leu Thr Arg Glu Val Tyr Thr Asp Pro Val Ile
                260                 265                 270

AAT ATA ACT GAC TAT AGA GTT GGC CCC AGC TTC GAG AAT ATT GAG AAC        864
Asn Ile Thr Asp Tyr Arg Val Gly Pro Ser Phe Glu Asn Ile Glu Asn
        275                 280                 285

TCA GCC ATT AGA AGC CCC CAC CTT ATG GAC TTC TTA AAT AAT TTG ACC        912
Ser Ala Ile Arg Ser Pro His Leu Met Asp Phe Leu Asn Asn Leu Thr
        290                 295                 300

ATT GAT ACG GAT TTG ATT AGA GGT GTT CAC TAT TGG GCA GGG CAT CGT        960
Ile Asp Thr Asp Leu Ile Arg Gly Val His Tyr Trp Ala Gly His Arg
305                 310                 315                 320

GTA ACT TCT CAT TTT ACA GGT AGT TCT CAA GTG ATA ACA ACC CCT CAA       1008
Val Thr Ser His Phe Thr Gly Ser Ser Gln Val Ile Thr Thr Pro Gln
                325                 330                 335

TAT GGG ATA ACC GCA AAT GCG GAA CCA AGA CGA ACT ATT GCT CCT AGT       1056
Tyr Gly Ile Thr Ala Asn Ala Glu Pro Arg Arg Thr Ile Ala Pro Ser
                340                 345                 350

ACT TTT CCA GGT CTT AAC CTA TTT TAT AGA ACA TTA TCA AAT CCT TTC       1104
Thr Phe Pro Gly Leu Asn Leu Phe Tyr Arg Thr Leu Ser Asn Pro Phe
                355                 360                 365

TTC CGA AGA TCA GAA AAT ATT ACT CCT ACC TTA GGG ATA AAT GTA GTA       1152
Phe Arg Arg Ser Glu Asn Ile Thr Pro Thr Leu Gly Ile Asn Val Val
    370                 375                 380

CAG GGA GTA GGG TTC ATT CAA CCA AAT AAT GCT GAA GTT CTA TAT AGA       1200
Gln Gly Val Gly Phe Ile Gln Pro Asn Asn Ala Glu Val Leu Tyr Arg
385                 390                 395                 400

AGT AGG GGG ACA GTA GAT TCT CTT AAT GAG TTA CCA ATT GAT GGT GAG       1248
Ser Arg Gly Thr Val Asp Ser Leu Asn Glu Leu Pro Ile Asp Gly Glu
                405                 410                 415
```

```
                                                           -continued

AAT TCA TTA GTT GGA TAT AGT CAT CGA TTA AGT CAT GTT ACA CTA ACC              1296
Asn Ser Leu Val Gly Tyr Ser His Arg Leu Ser His Val Thr Leu Thr
            420                 425                 430

AGG TCG TTA TAT AAT ACT AAT ATA ACT AGC CTG CCA ACA TTT GTT TGG              1344
Arg Ser Leu Tyr Asn Thr Asn Ile Thr Ser Leu Pro Thr Phe Val Trp
        435                 440                 445

ACA CAT CAC AGT GCT ACT AAT ACA AAT ACA ATT AAT CCA GAT ATT ATT              1392
Thr His His Ser Ala Thr Asn Thr Asn Thr Ile Asn Pro Asp Ile Ile
    450                 455                 460

ACA CAA ATA CCT TTA GTG AAA GGA TTT AGA CTT GGT GGT GGC ACC TCT              1440
Thr Gln Ile Pro Leu Val Lys Gly Phe Arg Leu Gly Gly Gly Thr Ser
465                 470                 475                 480

GTC ATT AAA GGA CCA GGA TTT ACA GGA GGG GAT ATC CTT CGA AGA AAT              1488
Val Ile Lys Gly Pro Gly Phe Thr Gly Gly Asp Ile Leu Arg Arg Asn
            485                 490                 495

ACC ATT GGT GAG TTT GTG TCT TTA CAA GTC AAT ATT AAC TCA CCA ATT              1536
Thr Ile Gly Glu Phe Val Ser Leu Gln Val Asn Ile Asn Ser Pro Ile
        500                 505                 510

ACC CAA AGA TAC CGT TTA AGA TTT CGT TAT GCT TCC AGT AGG GAT GCA              1584
Thr Gln Arg Tyr Arg Leu Arg Phe Arg Tyr Ala Ser Ser Arg Asp Ala
    515                 520                 525

CGA ATT ACT GTA GCG ATA GGA GGA CAA ATT AGA GTA GAT ATG ACC CTT              1632
Arg Ile Thr Val Ala Ile Gly Gly Gln Ile Arg Val Asp Met Thr Leu
530                 535                 540

GAA AAA ACC ATG GAA ATT GGG GAG AGC TTA ACA TCT AGA ACA TTT AGC              1680
Glu Lys Thr Met Glu Ile Gly Glu Ser Leu Thr Ser Arg Thr Phe Ser
545                 550                 555                 560

TAT ACC AAT TTT AGT AAT CCT TTT TCA TTT AGG GCT AAT CCA GAT ATA              1728
Tyr Thr Asn Phe Ser Asn Pro Phe Ser Phe Arg Ala Asn Pro Asp Ile
            565                 570                 575

ATT AGA ATA GCT GAA GAA CTT CCT ATT CGT GGT GGT GAG CTT TAT ATA              1776
Ile Arg Ile Ala Glu Glu Leu Pro Ile Arg Gly Gly Glu Leu Tyr Ile
        580                 585                 590

GAT AAA ATT GAA CTT ATT CTA GCA GAT GCA ACA TTT GAA GAA GAA TAT              1824
Asp Lys Ile Glu Leu Ile Leu Ala Asp Ala Thr Phe Glu Glu Glu Tyr
    595                 600                 605

GAT TTG GAA AGA GCA CAG AAG GCG GTG AAT GCC CTG TTT ACT TCT ACA              1872
Asp Leu Glu Arg Ala Gln Lys Ala Val Asn Ala Leu Phe Thr Ser Thr
610                 615                 620

AAT CAA CTA GGG CTA AAA ACA GAT GTG ACG GAT TAT CAT ATT GAT CAA              1920
Asn Gln Leu Gly Leu Lys Thr Asp Val Thr Asp Tyr His Ile Asp Gln
625                 630                 635                 640

GTT TCC AAT TTA GTT GAG TGT TTA TCG GAT GAA TTT TGT CTG GAT GAA              1968
Val Ser Asn Leu Val Glu Cys Leu Ser Asp Glu Phe Cys Leu Asp Glu
            645                 650                 655

AAG AGA GAA TTA TCC GAG AAA GTC AAA CAT GCG AAG CGA CTC AGT GAT              2016
Lys Arg Glu Leu Ser Glu Lys Val Lys His Ala Lys Arg Leu Ser Asp
        660                 665                 670

GAA CGG AAT TTA CTT CAA GAT CCA AAC TTC AGA GGG ATC AAT AGG CAA              2064
Glu Arg Asn Leu Leu Gln Asp Pro Asn Phe Arg Gly Ile Asn Arg Gln
    675                 680                 685

CCA GAC CGT GGC TGG AGA GGA AGC ACG GAT ATT ACT ATC CAA GGT GGA              2112
Pro Asp Arg Gly Trp Arg Gly Ser Thr Asp Ile Thr Ile Gln Gly Gly
690                 695                 700

GAT GAC GTA TTC AAA GAG AAT TAC GTC ACA TTA CCG GGT ACC TTT GAT              2160
Asp Asp Val Phe Lys Glu Asn Tyr Val Thr Leu Pro Gly Thr Phe Asp
705                 710                 715                 720

GAG TGC TAT CCA ACG TAT TTA TAT CAA AAA ATA GAT GAG TCG AAG TTA              2208
Glu Cys Tyr Pro Thr Tyr Leu Tyr Gln Lys Ile Asp Glu Ser Lys Leu
            725                 730                 735
```

```
AAA GCT TAT ACC CGC TAT GAA TTA AGA GGG TAT ATC GAG GAT AGT CAA    2256
Lys Ala Tyr Thr Arg Tyr Glu Leu Arg Gly Tyr Ile Glu Asp Ser Gln
            740                 745                 750

GAC TTA GAA ATC TAT TTA ATT CGC TAC AAT GCA AAA CAC GAG ACA GTA    2304
Asp Leu Glu Ile Tyr Leu Ile Arg Tyr Asn Ala Lys His Glu Thr Val
                755                 760                 765

AAC GTG CCA GGT ACG GGT TCC TTA TGG CCG CTT TCA GCC CAA AGT CCA    2352
Asn Val Pro Gly Thr Gly Ser Leu Trp Pro Leu Ser Ala Gln Ser Pro
        770                 775                 780

ATC GGA AAG TGT GGA GAA CCG AAT CGA TGC GCG CCA CAC CTT GAA TGG    2400
Ile Gly Lys Cys Gly Glu Pro Asn Arg Cys Ala Pro His Leu Glu Trp
785                 790                 795                 800

AAT CCT AAT CTA GAT TGC TCC TGC AGA GAC GGG GAA AAA TGT GCC CAT    2448
Asn Pro Asn Leu Asp Cys Ser Cys Arg Asp Gly Glu Lys Cys Ala His
                805                 810                 815

CAT TCC CAT CAT TTC TCC TTG GAC ATT GAT GTT GGA TGT ACA GAC TTA    2496
His Ser His His Phe Ser Leu Asp Ile Asp Val Gly Cys Thr Asp Leu
            820                 825                 830

AAT GAG GAC TTA GGT GTA TGG GTG ATA TTC AAG ATT AAG ACA CAA GAT    2544
Asn Glu Asp Leu Gly Val Trp Val Ile Phe Lys Ile Lys Thr Gln Asp
        835                 840                 845

GGC TAT GCA AGA CTA GGA AAT CTA GAG TTT CTC GAA GAG AAC CCA CTA    2592
Gly Tyr Ala Arg Leu Gly Asn Leu Glu Phe Leu Glu Glu Asn Pro Leu
    850                 855                 860

TTA GGG GAA GCA CTA GCT CGT GTG AAA AGA GCG GAG AAA AAA TGG AGA    2640
Leu Gly Glu Ala Leu Ala Arg Val Lys Arg Ala Glu Lys Lys Trp Arg
865                 870                 875                 880

GAC AAA TGC GAA AAA TTG GAA TGG GAA ACA AAT ATT GTT TAT AAA GAG    2688
Asp Lys Cys Glu Lys Leu Glu Trp Glu Thr Asn Ile Val Tyr Lys Glu
                885                 890                 895

GCA AAA GAA TCT GTA GAT GCT TTA TTT GTA AAC TCT CAA TAT GAT AGA    2736
Ala Lys Glu Ser Val Asp Ala Leu Phe Val Asn Ser Gln Tyr Asp Arg
            900                 905                 910

TTA CAA GCG GAT ACG AAT ATC GCG ATG ATT CAT GCG GCA GAT AAA CGC    2784
Leu Gln Ala Asp Thr Asn Ile Ala Met Ile His Ala Ala Asp Lys Arg
        915                 920                 925

GTT CAT AGC ATT CGA GAA GCG TAT CTG CCA GAG CTG TCT GTG ATT CCG    2832
Val His Ser Ile Arg Glu Ala Tyr Leu Pro Glu Leu Ser Val Ile Pro
    930                 935                 940

GGT GTC AAT GCG GCT ATT TTT GAA GAA TTA GAA GGG CGT ATT TTC ACT    2880
Gly Val Asn Ala Ala Ile Phe Glu Glu Leu Glu Gly Arg Ile Phe Thr
945                 950                 955                 960

GCA TTC TCC CTA TAT GAT GCG AGA AAT GTC ATT AAA AAT GGC GAT TTC    2928
Ala Phe Ser Leu Tyr Asp Ala Arg Asn Val Ile Lys Asn Gly Asp Phe
                965                 970                 975

AAT AAT GGC TTA TCA TGC TGG AAC GTG AAA GGG CAT GTA GAT GTA GAA    2976
Asn Asn Gly Leu Ser Cys Trp Asn Val Lys Gly His Val Asp Val Glu
            980                 985                 990

GAA CAG AAC AAC CAT CGT TCG GTC CTT GTT GTT CCA GAA TGG GAA GCA    3024
Glu Gln Asn Asn His Arg Ser Val Leu Val Val Pro Glu Trp Glu Ala
        995                 1000                1005

GAA GTG TCA CAA GAA GTT CGT GTT TGT CCG GGT CGT GGC TAT ATC CTT    3072
Glu Val Ser Gln Glu Val Arg Val Cys Pro Gly Arg Gly Tyr Ile Leu
    1010                1015                1020

CGT GTT ACA GCG TAC AAA GAG GGA TAT GGA GAG GGC TGT GTA ACG ATT    3120
Arg Val Thr Ala Tyr Lys Glu Gly Tyr Gly Glu Gly Cys Val Thr Ile
1025                1030                1035                1040

CAT GAG ATC GAA GAC AAT ACA GAC GAA CTG AAA TTC AGC AAC TGT GTA    3168
His Glu Ile Glu Asp Asn Thr Asp Glu Leu Lys Phe Ser Asn Cys Val
```

-continued

```
                   1045                1050                1055
GAA GAG GAA GTA TAT CCA AAC AAC ACG GTA ACG TGT AAT AAT TAT ACT          3216
Glu Glu Glu Val Tyr Pro Asn Asn Thr Val Thr Cys Asn Asn Tyr Thr
                1060                1065                1070

GCG ACT CAA GAA GAA CAT GAG GGT ACG TAC ACT TCC CGT AAT CGA GGA          3264
Ala Thr Gln Glu Glu His Glu Gly Thr Tyr Thr Ser Arg Asn Arg Gly
            1075                1080                1085

TAT GAC GAA GCC TAT GAA AGC AAT TCT TCT GTA CAT GCG TCA GTC TAT          3312
Tyr Asp Glu Ala Tyr Glu Ser Asn Ser Ser Val His Ala Ser Val Tyr
        1090                1095                1100

GAA GAA AAA TCG TAT ACA GAT AGA CGA AGA GAG AAT CCT TGT GAA TCT          3360
Glu Glu Lys Ser Tyr Thr Asp Arg Arg Arg Glu Asn Pro Cys Glu Ser
1105                1110                1115                1120

AAC AGA GGA TAT GGG GAT TAC ACA CCA CTA CCA GCT GGC TAT GTG ACA          3408
Asn Arg Gly Tyr Gly Asp Tyr Thr Pro Leu Pro Ala Gly Tyr Val Thr
            1125                1130                1135

AAA GAA TTA GAG TAC TTC CCA GAA ACC GAT AAG GTA TGG ATT GAG ATC          3456
Lys Glu Leu Glu Tyr Phe Pro Glu Thr Asp Lys Val Trp Ile Glu Ile
        1140                1145                1150

GGA GAA ACG GAA GGA ACA TTC ATC GTG GAC AGC GTG GAA TTA CTT CTT          3504
Gly Glu Thr Glu Gly Thr Phe Ile Val Asp Ser Val Glu Leu Leu Leu
    1155                1160                1165

ATG GAG GAA                                                               3513
Met Glu Glu
    1170
```

(2) INFORMATION FOR SEQ ID NO: 4:

(i) SEQUENCE CHARACTERISTICS:
        (A) LENGTH: 1171 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Glu Ile Val Asn Asn Gln Asn Gln Cys Val Pro Tyr Asn Cys Leu
 1               5                  10                  15

Asn Asn Pro Glu Asn Glu Ile Leu Asp Ile Glu Arg Ser Asn Ser Thr
            20                  25                  30

Val Ala Thr Asn Ile Ala Leu Glu Ile Ser Arg Leu Leu Ala Ser Ala
        35                  40                  45

Thr Pro Ile Gly Gly Ile Leu Gly Leu Phe Asp Ala Ile Trp Gly
    50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
            100                 105                 110

Arg Glu Trp Glu Ala Asp Pro Thr Asn Pro Ala Leu Lys Glu Glu Met
        115                 120                 125

Arg Thr Gln Phe Asn Asp Met Asn Ser Ile Leu Val Thr Ala Ile Pro
    130                 135                 140

Leu Phe Ser Val Gln Asn Tyr Gln Val Pro Phe Leu Ser Val Tyr Val
145                 150                 155                 160

Gln Ala Ala Asn Leu His Leu Ser Val Leu Arg Asp Val Ser Val Phe
                165                 170                 175
```

-continued

```
Gly Gln Ala Trp Gly Phe Asp Ile Ala Thr Ile Asn Ser Arg Tyr Asn
            180                 185                 190

Asp Leu Thr Arg Leu Ile Pro Ile Tyr Thr Asp Tyr Ala Val Arg Trp
            195                 200                 205

Tyr Asn Thr Gly Leu Asp Arg Leu Pro Arg Thr Gly Leu Arg Asn
            210                 215                 220

Trp Ala Arg Phe Asn Gln Phe Arg Arg Glu Leu Thr Ile Ser Val Leu
225                 230                 235                 240

Asp Ile Ile Ser Phe Phe Arg Asn Tyr Asp Ser Arg Leu Tyr Pro Ile
                    245                 250                 255

Pro Thr Ser Ser Gln Leu Thr Arg Glu Val Tyr Thr Asp Pro Val Ile
                    260                 265                 270

Asn Ile Thr Asp Tyr Arg Val Gly Pro Ser Phe Glu Asn Ile Glu Asn
                    275                 280                 285

Ser Ala Ile Arg Ser Pro His Leu Met Asp Phe Leu Asn Asn Leu Thr
            290                 295                 300

Ile Asp Thr Asp Leu Ile Arg Gly Val His Tyr Trp Ala Gly His Arg
305                 310                 315                 320

Val Thr Ser His Phe Thr Gly Ser Ser Gln Val Ile Thr Thr Pro Gln
                    325                 330                 335

Tyr Gly Ile Thr Ala Asn Ala Glu Pro Arg Arg Thr Ile Ala Pro Ser
            340                 345                 350

Thr Phe Pro Gly Leu Asn Leu Phe Tyr Arg Thr Leu Ser Asn Pro Phe
            355                 360                 365

Phe Arg Arg Ser Glu Asn Ile Thr Pro Thr Leu Gly Ile Asn Val Val
            370                 375                 380

Gln Gly Val Gly Phe Ile Gln Pro Asn Asn Ala Glu Val Leu Tyr Arg
385                 390                 395                 400

Ser Arg Gly Thr Val Asp Ser Leu Asn Glu Leu Pro Ile Asp Gly Glu
                    405                 410                 415

Asn Ser Leu Val Gly Tyr Ser His Arg Leu Ser His Val Thr Leu Thr
            420                 425                 430

Arg Ser Leu Tyr Asn Thr Asn Ile Thr Ser Leu Pro Thr Phe Val Trp
            435                 440                 445

Thr His His Ser Ala Thr Asn Thr Asn Thr Ile Asn Pro Asp Ile Ile
        450                 455                 460

Thr Gln Ile Pro Leu Val Lys Gly Phe Arg Leu Gly Gly Gly Thr Ser
465                 470                 475                 480

Val Ile Lys Gly Pro Gly Phe Thr Gly Gly Asp Ile Leu Arg Arg Asn
                    485                 490                 495

Thr Ile Gly Glu Phe Val Ser Leu Gln Val Asn Ile Asn Ser Pro Ile
            500                 505                 510

Thr Gln Arg Tyr Arg Leu Arg Phe Arg Tyr Ala Ser Ser Arg Asp Ala
            515                 520                 525

Arg Ile Thr Val Ala Ile Gly Gly Gln Ile Arg Val Asp Met Thr Leu
            530                 535                 540

Glu Lys Thr Met Glu Ile Gly Glu Ser Leu Thr Ser Arg Thr Phe Ser
545                 550                 555                 560

Tyr Thr Asn Phe Ser Asn Pro Phe Ser Phe Arg Ala Asn Pro Asp Ile
                    565                 570                 575

Ile Arg Ile Ala Glu Glu Leu Pro Ile Arg Gly Gly Glu Leu Tyr Ile
            580                 585                 590

Asp Lys Ile Glu Leu Ile Leu Ala Asp Ala Thr Phe Glu Glu Glu Tyr
```

```
            595                 600                 605
Asp Leu Glu Arg Ala Gln Lys Ala Val Asn Ala Leu Phe Thr Ser Thr
            610                 615                 620
Asn Gln Leu Gly Leu Lys Thr Asp Val Thr Asp Tyr His Ile Asp Gln
625                 630                 635                 640
Val Ser Asn Leu Val Glu Cys Leu Ser Asp Glu Phe Cys Leu Asp Glu
                    645                 650                 655
Lys Arg Glu Leu Ser Glu Lys Val Lys His Ala Lys Arg Leu Ser Asp
                660                 665                 670
Glu Arg Asn Leu Leu Gln Asp Pro Asn Phe Arg Gly Ile Asn Arg Gln
            675                 680                 685
Pro Asp Arg Gly Trp Arg Gly Ser Thr Asp Ile Thr Ile Gln Gly Gly
            690                 695                 700
Asp Asp Val Phe Lys Glu Asn Tyr Val Thr Leu Pro Gly Thr Phe Asp
705                 710                 715                 720
Glu Cys Tyr Pro Thr Tyr Leu Tyr Gln Lys Ile Asp Glu Ser Lys Leu
                    725                 730                 735
Lys Ala Tyr Thr Arg Tyr Glu Leu Arg Gly Tyr Ile Glu Asp Ser Gln
                740                 745                 750
Asp Leu Glu Ile Tyr Leu Ile Arg Tyr Asn Ala Lys His Glu Thr Val
            755                 760                 765
Asn Val Pro Gly Thr Gly Ser Leu Trp Pro Leu Ser Ala Gln Ser Pro
770                 775                 780
Ile Gly Lys Cys Gly Glu Pro Asn Arg Cys Ala Pro His Leu Glu Trp
785                 790                 795                 800
Asn Pro Asn Leu Asp Cys Ser Cys Arg Asp Gly Glu Lys Cys Ala His
                805                 810                 815
His Ser His His Phe Ser Leu Asp Ile Asp Val Gly Cys Thr Asp Leu
                820                 825                 830
Asn Glu Asp Leu Gly Val Trp Val Ile Phe Lys Ile Lys Thr Gln Asp
            835                 840                 845
Gly Tyr Ala Arg Leu Gly Asn Leu Glu Phe Leu Glu Glu Asn Pro Leu
            850                 855                 860
Leu Gly Glu Ala Leu Ala Arg Val Lys Arg Ala Glu Lys Lys Trp Arg
865                 870                 875                 880
Asp Lys Cys Glu Lys Leu Glu Trp Glu Thr Asn Ile Val Tyr Lys Glu
                885                 890                 895
Ala Lys Glu Ser Val Asp Ala Leu Phe Val Asn Ser Gln Tyr Asp Arg
                900                 905                 910
Leu Gln Ala Asp Thr Asn Ile Ala Met Ile His Ala Ala Asp Lys Arg
            915                 920                 925
Val His Ser Ile Arg Glu Ala Tyr Leu Pro Glu Leu Ser Val Ile Pro
930                 935                 940
Gly Val Asn Ala Ala Ile Phe Glu Glu Leu Glu Gly Arg Ile Phe Thr
945                 950                 955                 960
Ala Phe Ser Leu Tyr Asp Ala Arg Asn Val Ile Lys Asn Gly Asp Phe
                    965                 970                 975
Asn Asn Gly Leu Ser Cys Trp Asn Val Lys Gly His Val Asp Val Glu
                980                 985                 990
Glu Gln Asn Asn His Arg Ser Val Leu Val Val Pro Glu Trp Glu Ala
                995                 1000                1005
Glu Val Ser Gln Glu Val Arg Val Cys Pro Gly Arg Gly Tyr Ile Leu
            1010                1015                1020
```

```
Arg Val Thr Ala Tyr Lys Glu Gly Tyr Gly Glu Gly Cys Val Thr Ile
1025                1030                1035                1040

His Glu Ile Glu Asp Asn Thr Asp Glu Leu Lys Phe Ser Asn Cys Val
            1045                1050                1055

Glu Glu Glu Val Tyr Pro Asn Thr Val Thr Cys Asn Asn Tyr Thr
        1060                1065                1070

Ala Thr Gln Glu Glu His Gly Thr Tyr Thr Ser Arg Asn Arg Gly
        1075                1080                1085

Tyr Asp Glu Ala Tyr Glu Ser Asn Ser Ser Val His Ala Ser Val Tyr
            1090                1095                1100

Glu Glu Lys Ser Tyr Thr Asp Arg Arg Arg Glu Asn Pro Cys Glu Ser
1105                1110                1115                1120

Asn Arg Gly Tyr Gly Asp Tyr Thr Pro Leu Pro Ala Gly Tyr Val Thr
                1125                1130                1135

Lys Glu Leu Glu Tyr Phe Pro Glu Thr Asp Lys Val Trp Ile Glu Ile
            1140                1145                1150

Gly Glu Thr Glu Gly Thr Phe Ile Val Asp Ser Val Glu Leu Leu Leu
            1155                1160                1165

Met Glu Glu
    1170

(2) INFORMATION FOR SEQ ID NO: 5:

(i) SEQUENCE CHARACTERISTICS:
        (A) LENGTH: 3558 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iii) ANTI-SENSE: NO (vi) ORIGINAL SOURCE:
        (A) ORGANISM: Hybrid sequence (ix) FEATURE:
        (A) NAME/KEY: CDS
        (B) LOCATION: 1..3558

(xi) SEQUENCE DESCRIPTION: SEQ ID NO: 5:

ATG GAG ATA GTG AAT AAT CAG AAT CAA TGC GTG CCT TAT AAT TGT TTA      48
Met Glu Ile Val Asn Asn Gln Asn Gln Cys Val Pro Tyr Asn Cys Leu
1               5                   10                  15

AAT AAT CCT GAA AAT GAG ATA TTA GAT ATT GAA AGG TCA AAT AGT ACT      96
Asn Asn Pro Glu Asn Glu Ile Leu Asp Ile Glu Arg Ser Asn Ser Thr
                20                  25                  30

GTA GCA ACA AAC ATC GCC TTG GAG ATT AGT CGT CTG CTC GCT TCC GCA     144
Val Ala Thr Asn Ile Ala Leu Glu Ile Ser Arg Leu Leu Ala Ser Ala
            35                  40                  45

ACT CCA ATA GGG GGG ATT TTA TTA GGA TTG TTT GAT GCA ATA TGG GGG     192
Thr Pro Ile Gly Gly Ile Leu Leu Gly Leu Phe Asp Ala Ile Trp Gly
        50                  55                  60

TCT ATA GGC CCT TCA CAA TGG GAT TTA TTT TTA GAG CAA ATT GAG CTA     240
Ser Ile Gly Pro Ser Gln Trp Asp Leu Phe Leu Glu Gln Ile Glu Leu
65                  70                  75                  80

TTG ATT GAC CAA AAA ATA GAG GAA TTC GCT AGA AAC CAG GCA ATT TCT     288
Leu Ile Asp Gln Lys Ile Glu Glu Phe Ala Arg Asn Gln Ala Ile Ser
                85                  90                  95
```

| | | |
|---|---|---|
| AGA TTG GAA GGG ATA AGC AGT CTG TAC GGA ATT TAT ACA GAA GCT TTT | 336 | |
| Arg Leu Glu Gly Ile Ser Ser Leu Tyr Gly Ile Tyr Thr Glu Ala Phe | | |
| 100 105 110 | | |
| AGA GAG TGG GAA GCA GAT CCT ACT AAT CCA GCA TTA AAA GAA GAG ATG | 384 | |
| Arg Glu Trp Glu Ala Asp Pro Thr Asn Pro Ala Leu Lys Glu Glu Met | | |
| 115 120 125 | | |
| CGT ACT CAA TTT AAT GAC ATG AAC AGT ATT CTT GTA ACA GCT ATT CCT | 432 | |
| Arg Thr Gln Phe Asn Asp Met Asn Ser Ile Leu Val Thr Ala Ile Pro | | |
| 130 135 140 | | |
| CTT TTT TCA GTT CAA AAT TAT CAA GTC CCA TTT TTA TCA GTA TAT GTT | 480 | |
| Leu Phe Ser Val Gln Asn Tyr Gln Val Pro Phe Leu Ser Val Tyr Val | | |
| 145 150 155 160 | | |
| CAA GCT GCA AAT TTA CAT TTA TCG GTT TTG AGA GAT GTT TCA GTG TTT | 528 | |
| Gln Ala Ala Asn Leu His Leu Ser Val Leu Arg Asp Val Ser Val Phe | | |
| 165 170 175 | | |
| GGG CAG GCT TGG GGA TTT GAT ATA GCA ACA ATA AAT AGT CGT TAT AAT | 576 | |
| Gly Gln Ala Trp Gly Phe Asp Ile Ala Thr Ile Asn Ser Arg Tyr Asn | | |
| 180 185 190 | | |
| GAT CTG ACT AGA CTT ATT CCT ATA TAT ACA GAT TAT GCT GTA CGC TGG | 624 | |
| Asp Leu Thr Arg Leu Ile Pro Ile Tyr Thr Asp Tyr Ala Val Arg Trp | | |
| 195 200 205 | | |
| TAC AAT ACG GGA TTA GAT CGC TTA CCA CGA ACT GGT GGG CTG CGA AAC | 672 | |
| Tyr Asn Thr Gly Leu Asp Arg Leu Pro Arg Thr Gly Gly Leu Arg Asn | | |
| 210 215 220 | | |
| TGG GCA AGA TTT AAT CAG TTT AGA AGA GAG TTA ACA ATA TCA GTA TTA | 720 | |
| Trp Ala Arg Phe Asn Gln Phe Arg Arg Glu Leu Thr Ile Ser Val Leu | | |
| 225 230 235 240 | | |
| GAT ATT ATT TCT TTT TTC AGA AAT TAC GAT TCT AGA TTA TAT CCA ATT | 768 | |
| Asp Ile Ile Ser Phe Phe Arg Asn Tyr Asp Ser Arg Leu Tyr Pro Ile | | |
| 245 250 255 | | |
| CCA ACA AGC TCC CAA TTA ACG CGG GAA GTA TAT ACA GAT CCG GTA ATT | 816 | |
| Pro Thr Ser Ser Gln Leu Thr Arg Glu Val Tyr Thr Asp Pro Val Ile | | |
| 260 265 270 | | |
| AAT ATA ACT GAC TAT AGA GTT GGC CCC AGC TTC GAG AAT ATT GAG AAC | 864 | |
| Asn Ile Thr Asp Tyr Arg Val Gly Pro Ser Phe Glu Asn Ile Glu Asn | | |
| 275 280 285 | | |
| TCA GCC ATT AGA AGC CCC CAC CTT ATG GAC TTC TTA AAT AAT TTG ACC | 912 | |
| Ser Ala Ile Arg Ser Pro His Leu Met Asp Phe Leu Asn Asn Leu Thr | | |
| 290 295 300 | | |
| ATT GAT ACG GAT TTG ATT AGA GGT GTT CAC TAT TGG GCA GGG CAT CGT | 960 | |
| Ile Asp Thr Asp Leu Ile Arg Gly Val His Tyr Trp Ala Gly His Arg | | |
| 305 310 315 320 | | |
| GTA ACT TCT CAT TTT ACA GGT AGT TCT CAA GTG ATA ACA ACC CCT CAA | 1008 | |
| Val Thr Ser His Phe Thr Gly Ser Ser Gln Val Ile Thr Thr Pro Gln | | |
| 325 330 335 | | |
| TAT GGG ATA ACC GCA AAT GCG GAA CCA AGA CGA ACT ATT GCT CCT AGT | 1056 | |
| Tyr Gly Ile Thr Ala Asn Ala Glu Pro Arg Arg Thr Ile Ala Pro Ser | | |
| 340 345 350 | | |
| ACT TTT CCA GGT CTT AAC CTA TTT TAT AGA ACA TTA TCA AAT CCT TTC | 1104 | |
| Thr Phe Pro Gly Leu Asn Leu Phe Tyr Arg Thr Leu Ser Asn Pro Phe | | |
| 355 360 365 | | |
| TTC CGA AGA TCA GAA AAT ATT ACT CCT ACC TTA GGG ATA AAT GTA GTA | 1152 | |
| Phe Arg Arg Ser Glu Asn Ile Thr Pro Thr Leu Gly Ile Asn Val Val | | |
| 370 375 380 | | |
| CAG GGA GTA GGG TTC ATT CAA CCA AAT AAT GCT GAA GTT CTA TAT AGA | 1200 | |
| Gln Gly Val Gly Phe Ile Gln Pro Asn Asn Ala Glu Val Leu Tyr Arg | | |
| 385 390 395 400 | | |
| AGT AGG GGG ACA GTA GAT TCT CTT AAT GAG TTA CCA ATT GAT GGT GAG | 1248 | |
| Ser Arg Gly Thr Val Asp Ser Leu Asn Glu Leu Pro Ile Asp Gly Glu | | |
| 405 410 415 | | |

```
AAT TCA TTA GTT GGA TAT AGT CAT CGA TTA AGT CAT GTT ACA CTA ACC      1296
Asn Ser Leu Val Gly Tyr Ser His Arg Leu Ser His Val Thr Leu Thr
            420                 425                 430

AGG TCG TTA TAT AAT ACT AAT ATA ACT AGC CTG CCA ACA TTT GTT TGG      1344
Arg Ser Leu Tyr Asn Thr Asn Ile Thr Ser Leu Pro Thr Phe Val Trp
            435                 440                 445

ACA CAT CAC AGT GCT ACT AAT ACA AAT ACA ATT AAT CCA GAT ATT ATT      1392
Thr His His Ser Ala Thr Asn Thr Asn Thr Ile Asn Pro Asp Ile Ile
450                 455                 460

ACA CAA ATA CCT TTA GTG AAA GGA TTT AGA GTT TGG GGG GGC ACC TCT      1440
Thr Gln Ile Pro Leu Val Lys Gly Phe Arg Val Trp Gly Gly Thr Ser
465                 470                 475                 480

GTC ATT ACA GGA CCA GGA TTT ACA GGA GGG GAT ATC CTT CGA AGA AAT      1488
Val Ile Thr Gly Pro Gly Phe Thr Gly Gly Asp Ile Leu Arg Arg Asn
                485                 490                 495

ACC TTT GGT GAT TTT GTA TCT CTA CAA GTC AAT ATT AAT TCA CCA ATT      1536
Thr Phe Gly Asp Phe Val Ser Leu Gln Val Asn Ile Asn Ser Pro Ile
            500                 505                 510

ACC CAA AGA TAC CGT TTA AGA TTT CGT TAC GCT TCC AGT AGG GAT GCA      1584
Thr Gln Arg Tyr Arg Leu Arg Phe Arg Tyr Ala Ser Ser Arg Asp Ala
            515                 520                 525

CGA GTT ATA GTA TTA ACA GGA GCG GCA TCC ACA GGA GTG GGA GGC CAA      1632
Arg Val Ile Val Leu Thr Gly Ala Ala Ser Thr Gly Val Gly Gly Gln
530                 535                 540

GTT AGT GTA AAT ATG CCT CTT CAG AAA ACT ATG GAA ATA GGG GAG AAC      1680
Val Ser Val Asn Met Pro Leu Gln Lys Thr Met Glu Ile Gly Glu Asn
545                 550                 555                 560

TTA ACA TCT AGA ACA TTT AGA TAT ACC GAT TTT AGT AAT CCT TTT TCA      1728
Leu Thr Ser Arg Thr Phe Arg Tyr Thr Asp Phe Ser Asn Pro Phe Ser
                565                 570                 575

TTT AGA GCT AAT CCA GAT ATA ATT GGG ATA AGT GAA CAA CCT CTA TTT      1776
Phe Arg Ala Asn Pro Asp Ile Ile Gly Ile Ser Glu Gln Pro Leu Phe
            580                 585                 590

GGT GCA GGT TCT ATT AGT AGC GGT GAA CTT TAT ATA GAT AAA ATT GAA      1824
Gly Ala Gly Ser Ile Ser Ser Gly Glu Leu Tyr Ile Asp Lys Ile Glu
            595                 600                 605

ATT ATT CTA GCA GAT GCA ACA TTT GAA GCA GAA TCT GAT TTA GAA AGA      1872
Ile Ile Leu Ala Asp Ala Thr Phe Glu Ala Glu Ser Asp Leu Glu Arg
610                 615                 620

GCA CAA AAG GCG GTG AAT GCC CTG TTT ACT TCT TCC AAT CAA ATC GGG      1920
Ala Gln Lys Ala Val Asn Ala Leu Phe Thr Ser Ser Asn Gln Ile Gly
625                 630                 635                 640

TTA AAA ACC GAT GTG ACG GAT TAT CAT ATT GAT CAA GTA TCC AAT TTA      1968
Leu Lys Thr Asp Val Thr Asp Tyr His Ile Asp Gln Val Ser Asn Leu
                645                 650                 655

GTG GAT TGT TTA TCA GAT GAA TTT TGT CTG GAT GAA AAG CGA GAA TTG      2016
Val Asp Cys Leu Ser Asp Glu Phe Cys Leu Asp Glu Lys Arg Glu Leu
            660                 665                 670

TCC GAG AAA GTC AAA CAT GCG AAG CGA CTC AGT GAT GAG CGG AAT TTA      2064
Ser Glu Lys Val Lys His Ala Lys Arg Leu Ser Asp Glu Arg Asn Leu
            675                 680                 685

CTT CAA GAT CCA AAC TTC AGA GGG ATC AAT AGA CAA CCA GAC CGT GGC      2112
Leu Gln Asp Pro Asn Phe Arg Gly Ile Asn Arg Gln Pro Asp Arg Gly
            690                 695                 700

TGG AGA GGA AGT ACA GAT ATT ACC ATC CAA GGA GGA GAT GAC GTA TTC      2160
Trp Arg Gly Ser Thr Asp Ile Thr Ile Gln Gly Gly Asp Asp Val Phe
705                 710                 715                 720

AAA GAG AAT TAC GTC ACA CTA CCG GGT ACC GTT GAT GAG TGC TAT CCA      2208
Lys Glu Asn Tyr Val Thr Leu Pro Gly Thr Val Asp Glu Cys Tyr Pro
```

```
                725                 730                     735
ACG TAT TTA TAT CAG AAA ATA GAT GAG TCG AAA TTA AAA GCT TAT ACC    2256
Thr Tyr Leu Tyr Gln Lys Ile Asp Glu Ser Lys Leu Lys Ala Tyr Thr
            740                 745                 750

CGT TAT GAA TTA AGA GGG TAT ATC GAA GAT AGT CAA GAC TTA GAA ATC    2304
Arg Tyr Glu Leu Arg Gly Tyr Ile Glu Asp Ser Gln Asp Leu Glu Ile
            755                 760                 765

TAT TTG ATC CGT TAC AAT GCA AAA CAC GAA ATA GTA AAT GTG CCA GGC    2352
Tyr Leu Ile Arg Tyr Asn Ala Lys His Glu Ile Val Asn Val Pro Gly
            770                 775                 780

ACG GGT TCC TTA TGG CCG CTT TCA GCC CAA AGT CCA ATC GGA AAG TGT    2400
Thr Gly Ser Leu Trp Pro Leu Ser Ala Gln Ser Pro Ile Gly Lys Cys
785                 790                 795                 800

GGA GAA CCG AAT CGA TGC GCG CCA CAC CTT GAA TGG AAT CCT GAT CTA    2448
Gly Glu Pro Asn Arg Cys Ala Pro His Leu Glu Trp Asn Pro Asp Leu
                805                 810                 815

GAT TGT TCC TGC AGA GAC GGG GAA AAA TGT GCA CAT CAT TCC CAT CAT    2496
Asp Cys Ser Cys Arg Asp Gly Glu Lys Cys Ala His His Ser His His
            820                 825                 830

TTC ACC TTG GAT ATT GAT GTT GGA TGT ACA GAC TTA AAT GAG GAC TTA    2544
Phe Thr Leu Asp Ile Asp Val Gly Cys Thr Asp Leu Asn Glu Asp Leu
            835                 840                 845

GGT GTA TGG GTG ATA TTC AAG ATT AAG ACG CAA GAT GGC CAT GCA AGA    2592
Gly Val Trp Val Ile Phe Lys Ile Lys Thr Gln Asp Gly His Ala Arg
    850                 855                 860

CTA GGG AAT CTA GAG TTT CTC GAA GAG AAA CCA TTA TTA GGG GAA GCA    2640
Leu Gly Asn Leu Glu Phe Leu Glu Glu Lys Pro Leu Leu Gly Glu Ala
865                 870                 875                 880

CTA GCT CGT GTG AAA AGA GCG GAG AAG AAG TGG AGA GAC AAA CGA GAG    2688
Leu Ala Arg Val Lys Arg Ala Glu Lys Lys Trp Arg Asp Lys Arg Glu
                885                 890                 895

AAA CTG CAG TTG GAA ACA AAT ATT GTT TAT AAA GAG GCA AAA GAA TCT    2736
Lys Leu Gln Leu Glu Thr Asn Ile Val Tyr Lys Glu Ala Lys Glu Ser
            900                 905                 910

GTA GAT GCT TTA TTT GTA AAC TCT CAA TAT GAT AGA TTA CAA GTG GAT    2784
Val Asp Ala Leu Phe Val Asn Ser Gln Tyr Asp Arg Leu Gln Val Asp
            915                 920                 925

ACG AAC ATC GCG ATG ATT CAT GCG GCA GAT AAA CGC GTT CAT AGA ATC    2832
Thr Asn Ile Ala Met Ile His Ala Ala Asp Lys Arg Val His Arg Ile
            930                 935                 940

CGG GAA GCG TAT CTG CCA GAG TTG TCT GTG ATT CCA GGT GTC AAT GCG    2880
Arg Glu Ala Tyr Leu Pro Glu Leu Ser Val Ile Pro Gly Val Asn Ala
945                 950                 955                 960

GCC ATT TTC GAA GAA TTA GAG GGA CGT ATT TTT ACA GCG TAT TCC TTA    2928
Ala Ile Phe Glu Glu Leu Glu Gly Arg Ile Phe Thr Ala Tyr Ser Leu
                965                 970                 975

TAT GAT GCG AGA AAT GTC ATT AAA AAT GGC GAT TTC AAT AAT GGC TTA    2976
Tyr Asp Ala Arg Asn Val Ile Lys Asn Gly Asp Phe Asn Asn Gly Leu
            980                 985                 990

TTA TGC TGG AAC GTG AAA GGT CAT GTA GAT GTA GAA GAG CAA AAC AAC    3024
Leu Cys Trp Asn Val Lys Gly His Val Asp Val Glu Glu Gln Asn Asn
            995                 1000                1005

CAC CGT TCG GTC CTT GTT ATC CCA GAA TGG GAG GCA GAA GTG TCA CAA    3072
His Arg Ser Val Leu Val Ile Pro Glu Trp Glu Ala Glu Val Ser Gln
            1010                1015                1020

GAG GTT CGT GTC TGT CCA GGT CGT GGC TAT ATC CTT CGT GTC ACA GCA    3120
Glu Val Arg Val Cys Pro Gly Arg Gly Tyr Ile Leu Arg Val Thr Ala
1025                1030                1035                1040

TAT AAA GAG GGA TAT GGA GAG GGC TGC GTA ACG ATC CAT GAG ATC GAA    3168
```

```
                                                          -continued

Tyr Lys Glu Gly Tyr Gly Glu Gly Cys Val Thr Ile His Glu Ile Glu
                1045                1050                1055

GAC AAT ACA GAC GAA CTG AAA TTC AGC AAC TGT GTA GAA GAG GAA GTA       3216
Asp Asn Thr Asp Glu Leu Lys Phe Ser Asn Cys Val Glu Glu Glu Val
                1060                1065                1070

TAT CCA AAC AAC ACA GTA ACG TGT AAT AAT TAT ACT GGG ACT CAA GAA       3264
Tyr Pro Asn Asn Thr Val Thr Cys Asn Asn Tyr Thr Gly Thr Gln Glu
                1075                1080                1085

GAA TAT GAG GGT ACG TAC ACT TCT CGT AAT CAA GGA TAT GAC GAA GCC       3312
Glu Tyr Glu Gly Thr Tyr Thr Ser Arg Asn Gln Gly Tyr Asp Glu Ala
                1090                1095                1100

TAT GGT AAT AAC CCT TCC GTA CCA GCT GAT TAC GCT TCA GTC TAT GAA       3360
Tyr Gly Asn Asn Pro Ser Val Pro Ala Asp Tyr Ala Ser Val Tyr Glu
1105                1110                1115                1120

GAA AAA TCG TAT ACA GAT GGA CGA AGA GAG AAT CCT TGT GAA TCT AAC       3408
Glu Lys Ser Tyr Thr Asp Gly Arg Arg Glu Asn Pro Cys Glu Ser Asn
                1125                1130                1135

AGA GGC TAT GGG GAT TAC ACA CCA CTA CCG GCT GGT TAT GTA ACA AAG       3456
Arg Gly Tyr Gly Asp Tyr Thr Pro Leu Pro Ala Gly Tyr Val Thr Lys
                1140                1145                1150

GAT TTA GAG TAC TTC CCA GAG ACC GAT AAG GTA TGG ATT GAG ATC GGA       3504
Asp Leu Glu Tyr Phe Pro Glu Thr Asp Lys Val Trp Ile Glu Ile Gly
                1155                1160                1165

GAA ACA GAA GGA ACA TTC ATC GTG GAT AGC GTG GAA TTA CTC CTT ATG       3552
Glu Thr Glu Gly Thr Phe Ile Val Asp Ser Val Glu Leu Leu Leu Met
                1170                1175                1180

GAG GAA                                                               3558
Glu Glu
1185

(2) INFORMATION FOR SEQ ID NO: 6:

(i) SEQUENCE CHARACTERISTICS:
        (A) LENGTH: 1186 amino acids
        (B) TYPE: amino acid
        (D) TOPOLOGY: linear (ii) MOLECULE TYPE: protein (xi) SEQUENCE DESCRIPTION: SEQ ID NO: 6:

Met Glu Ile Val Asn Asn Gln Asn Gln Cys Val Pro Tyr Asn Cys Leu
 1                   5                  10                  15

Asn Asn Pro Glu Asn Glu Ile Leu Asp Ile Glu Arg Ser Asn Ser Thr
                20                  25                  30

Val Ala Thr Asn Ile Ala Leu Glu Ile Ser Arg Leu Leu Ala Ser Ala
            35                  40                  45

Thr Pro Ile Gly Gly Ile Leu Leu Gly Leu Phe Asp Ala Ile Trp Gly
        50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
                100                 105                 110

Arg Glu Trp Glu Ala Asp Pro Thr Asn Pro Ala Leu Lys Glu Glu Met
            115                 120                 125

Arg Thr Gln Phe Asn Asp Met Asn Ser Ile Leu Val Thr Ala Ile Pro
        130                 135                 140

Leu Phe Ser Val Gln Asn Tyr Gln Val Pro Phe Leu Ser Val Tyr Val
```

```
                145                 150                 155                 160
Gln Ala Asn Leu His Leu Ser Val Leu Arg Asp Val Ser Val Phe
                    165                 170                 175
Gly Gln Ala Trp Gly Phe Asp Ile Ala Thr Ile Asn Ser Arg Tyr Asn
                180                 185                 190
Asp Leu Thr Arg Leu Ile Pro Ile Tyr Thr Asp Tyr Ala Val Arg Trp
                195                 200                 205
Tyr Asn Thr Gly Leu Asp Arg Leu Pro Arg Thr Gly Leu Arg Asn
    210                 215                 220
Trp Ala Arg Phe Asn Gln Phe Arg Glu Leu Thr Ile Ser Val Leu
225                 230                 235                 240
Asp Ile Ile Ser Phe Phe Arg Asn Tyr Asp Ser Arg Leu Tyr Pro Ile
                245                 250                 255
Pro Thr Ser Ser Gln Leu Thr Arg Glu Val Tyr Thr Asp Pro Val Ile
                260                 265                 270
Asn Ile Thr Asp Tyr Arg Val Gly Pro Ser Phe Glu Asn Ile Glu Asn
                275                 280                 285
Ser Ala Ile Arg Ser Pro His Leu Met Asp Phe Leu Asn Asn Leu Thr
    290                 295                 300
Ile Asp Thr Asp Leu Ile Arg Gly Val His Tyr Trp Ala Gly His Arg
305                 310                 315                 320
Val Thr Ser His Phe Thr Gly Ser Ser Gln Val Ile Thr Thr Pro Gln
                325                 330                 335
Tyr Gly Ile Thr Ala Asn Ala Glu Pro Arg Arg Thr Ile Ala Pro Ser
                340                 345                 350
Thr Phe Pro Gly Leu Asn Leu Phe Tyr Arg Thr Leu Ser Asn Pro Phe
                355                 360                 365
Phe Arg Arg Ser Glu Asn Ile Thr Pro Thr Leu Gly Ile Asn Val Val
    370                 375                 380
Gln Gly Val Gly Phe Ile Gln Pro Asn Asn Ala Glu Val Leu Tyr Arg
385                 390                 395                 400
Ser Arg Gly Thr Val Asp Ser Leu Asn Glu Leu Pro Ile Asp Gly Glu
                405                 410                 415
Asn Ser Leu Val Gly Tyr Ser His Arg Leu Ser His Val Thr Leu Thr
                420                 425                 430
Arg Ser Leu Tyr Asn Thr Asn Ile Thr Ser Leu Pro Thr Phe Val Trp
    435                 440                 445
Thr His His Ser Ala Thr Asn Thr Asn Thr Ile Asn Pro Asp Ile Ile
450                 455                 460
Thr Gln Ile Pro Leu Val Lys Gly Phe Arg Val Trp Gly Gly Thr Ser
465                 470                 475                 480
Val Ile Thr Gly Pro Gly Phe Thr Gly Gly Asp Ile Leu Arg Arg Asn
                485                 490                 495
Thr Phe Gly Asp Phe Val Ser Leu Gln Val Asn Ile Asn Ser Pro Ile
                500                 505                 510
Thr Gln Arg Tyr Arg Leu Arg Phe Arg Tyr Ala Ser Ser Arg Asp Ala
                515                 520                 525
Arg Val Ile Val Leu Thr Gly Ala Ala Ser Thr Gly Val Gly Gly Gln
                530                 535                 540
Val Ser Val Asn Met Pro Leu Gln Lys Thr Met Glu Ile Gly Glu Asn
545                 550                 555                 560
Leu Thr Ser Arg Thr Phe Arg Tyr Thr Asp Phe Ser Asn Pro Phe Ser
                565                 570                 575
```

```
Phe Arg Ala Asn Pro Asp Ile Ile Gly Ile Ser Glu Gln Pro Leu Phe
            580                 585                 590
Gly Ala Gly Ser Ile Ser Ser Gly Glu Leu Tyr Ile Asp Lys Ile Glu
        595                 600                 605
Ile Ile Leu Ala Asp Ala Thr Phe Glu Ala Glu Ser Asp Leu Glu Arg
    610                 615                 620
Ala Gln Lys Ala Val Asn Ala Leu Phe Thr Ser Ser Asn Gln Ile Gly
625                 630                 635                 640
Leu Lys Thr Asp Val Thr Asp Tyr His Ile Asp Gln Val Ser Asn Leu
                645                 650                 655
Val Asp Cys Leu Ser Asp Glu Phe Cys Leu Asp Glu Lys Arg Glu Leu
            660                 665                 670
Ser Glu Lys Val Lys His Ala Lys Arg Leu Ser Asp Glu Arg Asn Leu
        675                 680                 685
Leu Gln Asp Pro Asn Phe Arg Gly Ile Asn Arg Gln Pro Asp Arg Gly
    690                 695                 700
Trp Arg Gly Ser Thr Asp Ile Thr Ile Gln Gly Gly Asp Asp Val Phe
705                 710                 715                 720
Lys Glu Asn Tyr Val Thr Leu Pro Gly Thr Val Asp Glu Cys Tyr Pro
                725                 730                 735
Thr Tyr Leu Tyr Gln Lys Ile Asp Glu Ser Lys Leu Lys Ala Tyr Thr
            740                 745                 750
Arg Tyr Glu Leu Arg Gly Tyr Ile Glu Asp Ser Gln Asp Leu Glu Ile
        755                 760                 765
Tyr Leu Ile Arg Tyr Asn Ala Lys His Glu Ile Val Asn Val Pro Gly
    770                 775                 780
Thr Gly Ser Leu Trp Pro Leu Ser Ala Gln Ser Pro Ile Gly Lys Cys
785                 790                 795                 800
Gly Glu Pro Asn Arg Cys Ala Pro His Leu Glu Trp Asn Pro Asp Leu
                805                 810                 815
Asp Cys Ser Cys Arg Asp Gly Glu Lys Cys Ala His His Ser His His
            820                 825                 830
Phe Thr Leu Asp Ile Asp Val Gly Cys Thr Asp Leu Asn Glu Asp Leu
        835                 840                 845
Gly Val Trp Val Ile Phe Lys Ile Lys Thr Gln Asp Gly His Ala Arg
    850                 855                 860
Leu Gly Asn Leu Glu Phe Leu Glu Glu Lys Pro Leu Leu Gly Glu Ala
865                 870                 875                 880
Leu Ala Arg Val Lys Arg Ala Glu Lys Lys Trp Arg Asp Lys Arg Glu
                885                 890                 895
Lys Leu Gln Leu Glu Thr Asn Ile Val Tyr Lys Glu Ala Lys Glu Ser
            900                 905                 910
Val Asp Ala Leu Phe Val Asn Ser Gln Tyr Asp Arg Leu Gln Val Asp
        915                 920                 925
Thr Asn Ile Ala Met Ile His Ala Ala Asp Lys Arg Val His Arg Ile
    930                 935                 940
Arg Glu Ala Tyr Leu Pro Glu Leu Ser Val Ile Pro Gly Val Asn Ala
945                 950                 955                 960
Ala Ile Phe Glu Glu Leu Glu Gly Arg Ile Phe Thr Ala Tyr Ser Leu
                965                 970                 975
Tyr Asp Ala Arg Asn Val Ile Lys Asn Gly Asp Phe Asn Asn Gly Leu
            980                 985                 990
```

-continued

```
Leu Cys Trp Asn Val Lys Gly His Val Asp Val Glu Glu Gln Asn Asn
        995                 1000                1005

His Arg Ser Val Leu Val Ile Pro Glu Trp Glu Ala Glu Val Ser Gln
   1010                 1015                1020

Glu Val Arg Val Cys Pro Gly Arg Gly Tyr Ile Leu Arg Val Thr Ala
1025                1030                1035                1040

Tyr Lys Glu Gly Tyr Gly Glu Gly Cys Val Thr Ile His Glu Ile Glu
                1045                1050                1055

Asp Asn Thr Asp Glu Leu Lys Phe Ser Asn Cys Val Glu Glu Glu Val
            1060                1065                1070

Tyr Pro Asn Asn Thr Val Thr Cys Asn Asn Tyr Thr Gly Thr Gln Glu
        1075                1080                1085

Glu Tyr Glu Gly Thr Tyr Thr Ser Arg Asn Gln Gly Tyr Asp Glu Ala
    1090                1095                1100

Tyr Gly Asn Asn Pro Ser Val Pro Ala Asp Tyr Ala Ser Val Tyr Glu
1105                1110                1115                1120

Glu Lys Ser Tyr Thr Asp Gly Arg Arg Glu Asn Pro Cys Glu Ser Asn
                1125                1130                1135

Arg Gly Tyr Gly Asp Tyr Thr Pro Leu Pro Ala Gly Tyr Val Thr Lys
            1140                1145                1150

Asp Leu Glu Tyr Phe Pro Glu Thr Asp Lys Val Trp Ile Glu Ile Gly
        1155                1160                1165

Glu Thr Glu Gly Thr Phe Ile Val Asp Ser Val Glu Leu Leu Leu Met
    1170                1175                1180

Glu Glu
1185
```

(2) INFORMATION FOR SEQ ID NO: 7:

(i) SEQUENCE CHARACTERISTICS:
        (A) LENGTH: 3579 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iii) ANTI-SENSE: NO (vi) ORIGINAL SOURCE:
        (A) ORGANISM: Hybrid toxin (ix) FEATURE:
        (A) NAME/KEY: CDS
        (B) LOCATION: 1..3579

(xi) SEQUENCE DESCRIPTION: SEQ ID NO: 7:

```
ATG GAT AAC AAT CCG AAC ATC AAT GAA TGC ATT CCT TAT AAT TGT TTA      48
Met Asp Asn Asn Pro Asn Ile Asn Glu Cys Ile Pro Tyr Asn Cys Leu
 1               5                  10                  15

AGT AAC CCT GAA GTA GAA GTA TTA GGT GGA GAA AGA ATA GAA ACT GGT      96
Ser Asn Pro Glu Val Glu Val Leu Gly Gly Glu Arg Ile Glu Thr Gly
            20                  25                  30

TAC ACC CCA ATC GAT ATT TCC TTG TCG CTA ACG CAA TTT CTT TTG AGT     144
Tyr Thr Pro Ile Asp Ile Ser Leu Ser Leu Thr Gln Phe Leu Leu Ser
        35                  40                  45

GAA TTT GTT CCC GGT GCT GGA TTT GTG TTA GGA CTA GTT GAT ATA ATA     192
Glu Phe Val Pro Gly Ala Gly Phe Val Leu Gly Leu Val Asp Ile Ile
    50                  55                  60
```

-continued

| | |
|---|---|
| TGG GGA ATT TTT GGT CCC TCT CAA TGG GAC GCA TTT CTT GTA CAA ATT<br>Trp Gly Ile Phe Gly Pro Ser Gln Trp Asp Ala Phe Leu Val Gln Ile<br>65                      70                    75                    80 | 240 |
| GAA CAG TTA ATT AAC CAA AGA ATA GAA GAA TTC GCT AGG AAC CAA GCC<br>Glu Gln Leu Ile Asn Gln Arg Ile Glu Glu Phe Ala Arg Asn Gln Ala<br>                    85                    90                    95 | 288 |
| ATT TCT AGA TTA GAA GGA CTA AGC AAT CTT TAT CAA ATT TAC GCA GAA<br>Ile Ser Arg Leu Glu Gly Leu Ser Asn Leu Tyr Gln Ile Tyr Ala Glu<br>        100                    105                  110 | 336 |
| TCT TTT AGA GAG TGG GAA GCA GAT CCT ACT AAT CCA GCA TTA AGA GAA<br>Ser Phe Arg Glu Trp Glu Ala Asp Pro Thr Asn Pro Ala Leu Arg Glu<br>        115                    120                  125 | 384 |
| GAG ATG CGT ATT CAA TTC AAT GAC ATG AAC AGT GCC CTT ACA ACC GCT<br>Glu Met Arg Ile Gln Phe Asn Asp Met Asn Ser Ala Leu Thr Thr Ala<br>130                      135                    140 | 432 |
| ATT CCT CTT TTT GCA GTT CAA AAT TAT CAA GTT CCT CTT TTA TCA GTA<br>Ile Pro Leu Phe Ala Val Gln Asn Tyr Gln Val Pro Leu Leu Ser Val<br>145                      150                    155                    160 | 480 |
| TAT GTT CAA GCT GCA AAT TTA CAT TTA TCA GTT TTG AGA GAT GTT TCA<br>Tyr Val Gln Ala Ala Asn Leu His Leu Ser Val Leu Arg Asp Val Ser<br>                    165                    170                    175 | 528 |
| GTG TTT GGA CAA AGG TGG GGA TTT GAT GCC GCG ACT ATC AAT AGT CGT<br>Val Phe Gly Gln Arg Trp Gly Phe Asp Ala Ala Thr Ile Asn Ser Arg<br>        180                    185                  190 | 576 |
| TAT AAT GAT TTA ACT AGG CTT ATT GGC AAC TAT ACA GAT CAT GCT GTA<br>Tyr Asn Asp Leu Thr Arg Leu Ile Gly Asn Tyr Thr Asp His Ala Val<br>        195                    200                  205 | 624 |
| CGC TGG TAC AAT ACG GGA TTA GAG CGT GTA TGG GGA CCG GAT TCT AGA<br>Arg Trp Tyr Asn Thr Gly Leu Glu Arg Val Trp Gly Pro Asp Ser Arg<br>210                      215                    220 | 672 |
| GAT TGG ATA AGA TAT AAT CAA TTT AGA AGA GAA TTA ACA CTA ACT GTA<br>Asp Trp Ile Arg Tyr Asn Gln Phe Arg Arg Glu Leu Thr Leu Thr Val<br>225                      230                    235                    240 | 720 |
| TTA GAT ATC GTT TCT CTA TTT CCG AAC TAT GAT AGT AGA ACG TAT CCA<br>Leu Asp Ile Val Ser Leu Phe Pro Asn Tyr Asp Ser Arg Thr Tyr Pro<br>                    245                    250                    255 | 768 |
| ATT CGA ACA GTT TCC CAA TTA ACA AGA GAA ATT TAT ACA AAC CCA GTA<br>Ile Arg Thr Val Ser Gln Leu Thr Arg Glu Ile Tyr Thr Asn Pro Val<br>        260                    265                  270 | 816 |
| TTA GAA AAT TTT GAT GGT AGT TTT CGA GGC TCG GCT CAG GGC ATA GAA<br>Leu Glu Asn Phe Asp Gly Ser Phe Arg Gly Ser Ala Gln Gly Ile Glu<br>        275                    280                  285 | 864 |
| GGA AGT ATT AGG AGT CCA CAT TTG ATG GAT ATA CTT AAC AGT ATA ACC<br>Gly Ser Ile Arg Ser Pro His Leu Met Asp Ile Leu Asn Ser Ile Thr<br>290                      295                    300 | 912 |
| ATC TAT ACG GAT GCT CAT AGA GGA GAA TAT TAT TGG TCA GGG CAT CAA<br>Ile Tyr Thr Asp Ala His Arg Gly Glu Tyr Tyr Trp Ser Gly His Gln<br>305                      310                    315                    320 | 960 |
| ATA ATG GCT TCT CCT GTA GGG TTT TCG GGG CCA GAA TTC ACT TTT CCG<br>Ile Met Ala Ser Pro Val Gly Phe Ser Gly Pro Glu Phe Thr Phe Pro<br>                    325                    330                    335 | 1008 |
| CTA TAT GGA ACT ATG GGA AAT GCA GCT CCA CAA CAA CGT ATT GTT GCT<br>Leu Tyr Gly Thr Met Gly Asn Ala Ala Pro Gln Gln Arg Ile Val Ala<br>        340                    345                  350 | 1056 |
| CAA CTA GGT CAG GGC GTG TAT AGA ACA TTA TCG TCC ACT TTA TAT AGA<br>Gln Leu Gly Gln Gly Val Tyr Arg Thr Leu Ser Ser Thr Leu Tyr Arg<br>        355                    360                  365 | 1104 |
| AGA CCT TTT AAT ATA GGG ATA AAT AAT CAA CAA CTA TCT GTT CTT GAC<br>Arg Pro Phe Asn Ile Gly Ile Asn Asn Gln Gln Leu Ser Val Leu Asp<br>        370                    375                  380 | 1152 |

```
GGG ACA GAA TTT GCT TAT GGA ACC TCC TCA AAT TTG CCA TCC GCT GTA      1200
Gly Thr Glu Phe Ala Tyr Gly Thr Ser Ser Asn Leu Pro Ser Ala Val
385                 390                 395                 400

TAC AGA AAA AGC GGA ACG GTA GAT TCG CTG GAT GAA ATA CCG CCA CAG      1248
Tyr Arg Lys Ser Gly Thr Val Asp Ser Leu Asp Glu Ile Pro Pro Gln
                405                 410                 415

AAT AAC AAC GTG CCA CCT AGG CAA GGA TTT AGT CAT CGA TTA AGC CAT      1296
Asn Asn Asn Val Pro Pro Arg Gln Gly Phe Ser His Arg Leu Ser His
            420                 425                 430

GTT TCA ATG TTT CGT TCA GGC TTT AGT AAT AGT AGT GTA AGT ATA ATA      1344
Val Ser Met Phe Arg Ser Gly Phe Ser Asn Ser Ser Val Ser Ile Ile
        435                 440                 445

AGA GCT CCT ATG TTC TCT TGG ATA CAT CGT AGT GCA ACT CTT ACA AAT      1392
Arg Ala Pro Met Phe Ser Trp Ile His Arg Ser Ala Thr Leu Thr Asn
    450                 455                 460

ACA ATT GAT CCA GAG AGA ATT AAT CAA ATA CCT TTA GTG AAA GGA TTT      1440
Thr Ile Asp Pro Glu Arg Ile Asn Gln Ile Pro Leu Val Lys Gly Phe
465                 470                 475                 480

AGA GTT TGG GGG GGC ACC TCT GTC ATT ACA GGA CCA GGA TTT ACA GGA      1488
Arg Val Trp Gly Gly Thr Ser Val Ile Thr Gly Pro Gly Phe Thr Gly
                485                 490                 495

GGG GAT ATC CTT CGA AGA AAT ACC TTT GGT GAT TTT GTA TCT CTA CAA      1536
Gly Asp Ile Leu Arg Arg Asn Thr Phe Gly Asp Phe Val Ser Leu Gln
            500                 505                 510

GTC AAT ATT AAT TCA CCA ATT ACC CAA AGA TAC CGT TTA AGA TTT CGT      1584
Val Asn Ile Asn Ser Pro Ile Thr Gln Arg Tyr Arg Leu Arg Phe Arg
        515                 520                 525

TAC GCT TCC AGT AGG GAT GCA CGA GTT ATA GTA TTA ACA GGA GCG GCA      1632
Tyr Ala Ser Ser Arg Asp Ala Arg Val Ile Val Leu Thr Gly Ala Ala
    530                 535                 540

TCC ACA GGA GTG GGA GGC CAA GTT AGT GTA AAT ATG CCT CTT CAG AAA      1680
Ser Thr Gly Val Gly Gly Gln Val Ser Val Asn Met Pro Leu Gln Lys
545                 550                 555                 560

ACT ATG GAA ATA GGG GAG AAC TTA ACA TCT AGA ACA TTT AGA TAT ACC      1728
Thr Met Glu Ile Gly Glu Asn Leu Thr Ser Arg Thr Phe Arg Tyr Thr
                565                 570                 575

GAT TTT AGT AAT CCT TTT TCA TTT AGA GCT AAT CCA GAT ATA ATT GGG      1776
Asp Phe Ser Asn Pro Phe Ser Phe Arg Ala Asn Pro Asp Ile Ile Gly
            580                 585                 590

ATA AGT GAA CAA CCT CTA TTT GGT GCA GGT TCT ATT AGT AGC GGT GAA      1824
Ile Ser Glu Gln Pro Leu Phe Gly Ala Gly Ser Ile Ser Ser Gly Glu
        595                 600                 605

CTT TAT ATA GAT AAA ATT GAA ATT ATT CTA GCA GAT GCA ACA TTT GAA      1872
Leu Tyr Ile Asp Lys Ile Glu Ile Ile Leu Ala Asp Ala Thr Phe Glu
    610                 615                 620

GCA GAA TCT GAT TTA GAA AGA GCA CAA AAG GCG GTG AAT GCC CTG TTT      1920
Ala Glu Ser Asp Leu Glu Arg Ala Gln Lys Ala Val Asn Ala Leu Phe
625                 630                 635                 640

ACT TCT TCC AAT CAA ATC GGG TTA AAA ACC GAT GTG ACG GAT TAT CAT      1968
Thr Ser Ser Asn Gln Ile Gly Leu Lys Thr Asp Val Thr Asp Tyr His
                645                 650                 655

ATT GAT CAA GTA TCC AAT TTA GTG GAT TGT TTA TCA GAT GAA TTT TGT      2016
Ile Asp Gln Val Ser Asn Leu Val Asp Cys Leu Ser Asp Glu Phe Cys
            660                 665                 670

CTG GAT GAA AAG CGA GAA TTG TCC GAG AAA GTC AAA CAT GCG AAG CGA      2064
Leu Asp Glu Lys Arg Glu Leu Ser Glu Lys Val Lys His Ala Lys Arg
        675                 680                 685

CTC AGT GAT GAG CGG AAT TTA CTT CAA GAT CCA AAC TTC AGA GGG ATC      2112
Leu Ser Asp Glu Arg Asn Leu Leu Gln Asp Pro Asn Phe Arg Gly Ile
```

```
              690                 695                 700
AAT AGA CAA CCA GAC CGT GGC TGG AGA GGA AGT ACA GAT ATT ACC ATC          2160
Asn Arg Gln Pro Asp Arg Gly Trp Arg Gly Ser Thr Asp Ile Thr Ile
705                 710                 715                 720

CAA GGA GGA GAT GAC GTA TTC AAA GAG AAT TAC GTC ACA CTA CCG GGT          2208
Gln Gly Gly Asp Asp Val Phe Lys Glu Asn Tyr Val Thr Leu Pro Gly
                    725                 730                 735

ACC GTT GAT GAG TGC TAT CCA ACG TAT TTA TAT CAG AAA ATA GAT GAG          2256
Thr Val Asp Glu Cys Tyr Pro Thr Tyr Leu Tyr Gln Lys Ile Asp Glu
                740                 745                 750

TCG AAA TTA AAA GCT TAT ACC CGT TAT GAA TTA AGA GGG TAT ATC GAA          2304
Ser Lys Leu Lys Ala Tyr Thr Arg Tyr Glu Leu Arg Gly Tyr Ile Glu
            755                 760                 765

GAT AGT CAA GAC TTA GAA ATC TAT TTG ATC CGT TAC AAT GCA AAA CAC          2352
Asp Ser Gln Asp Leu Glu Ile Tyr Leu Ile Arg Tyr Asn Ala Lys His
        770                 775                 780

GAA ATA GTA AAT GTG CCA GGC ACG GGT TCC TTA TGG CCG CTT TCA GCC          2400
Glu Ile Val Asn Val Pro Gly Thr Gly Ser Leu Trp Pro Leu Ser Ala
785                 790                 795                 800

CAA AGT CCA ATC GGA AAG TGT GGA GAA CCG AAT CGA TGC GCG CCA CAC          2448
Gln Ser Pro Ile Gly Lys Cys Gly Glu Pro Asn Arg Cys Ala Pro His
                    805                 810                 815

CTT GAA TGG AAT CCT GAT CTA GAT TGT TCC TGC AGA GAC GGG GAA AAA          2496
Leu Glu Trp Asn Pro Asp Leu Asp Cys Ser Cys Arg Asp Gly Glu Lys
                820                 825                 830

TGT GCA CAT CAT TCC CAT CAT TTC ACC TTG GAT ATT GAT GTT GGA TGT          2544
Cys Ala His His Ser His His Phe Thr Leu Asp Ile Asp Val Gly Cys
            835                 840                 845

ACA GAC TTA AAT GAG GAC TTA GGT GTA TGG GTG ATA TTC AAG ATT AAG          2592
Thr Asp Leu Asn Glu Asp Leu Gly Val Trp Val Ile Phe Lys Ile Lys
        850                 855                 860

ACG CAA GAT GGC CAT GCA AGA CTA GGG AAT CTA GAG TTT CTC GAA GAG          2640
Thr Gln Asp Gly His Ala Arg Leu Gly Asn Leu Glu Phe Leu Glu Glu
865                 870                 875                 880

AAA CCA TTA TTA GGG GAA GCA CTA GCT CGT GTG AAA AGA GCG GAG AAG          2688
Lys Pro Leu Leu Gly Glu Ala Leu Ala Arg Val Lys Arg Ala Glu Lys
                    885                 890                 895

AAG TGG AGA GAC AAA CGA GAG AAA CTG CAG TTG GAA ACA AAT ATT GTT          2736
Lys Trp Arg Asp Lys Arg Glu Lys Leu Gln Leu Glu Thr Asn Ile Val
                900                 905                 910

TAT AAA GAG GCA AAA GAA TCT GTA GAT GCT TTA TTT GTA AAC TCT CAA          2784
Tyr Lys Glu Ala Lys Glu Ser Val Asp Ala Leu Phe Val Asn Ser Gln
            915                 920                 925

TAT GAT AGA TTA CAA GTG GAT ACG AAC ATC GCG ATG ATT CAT GCG GCA          2832
Tyr Asp Arg Leu Gln Val Asp Thr Asn Ile Ala Met Ile His Ala Ala
        930                 935                 940

GAT AAA CGC GTT CAT AGA ATC CGG GAA GCG TAT CTG CCA GAG TTG TCT          2880
Asp Lys Arg Val His Arg Ile Arg Glu Ala Tyr Leu Pro Glu Leu Ser
945                 950                 955                 960

GTG ATT CCA GGT GTC AAT GCG GCC ATT TTC GAA GAA TTA GAG GGA CGT          2928
Val Ile Pro Gly Val Asn Ala Ala Ile Phe Glu Glu Leu Glu Gly Arg
                    965                 970                 975

ATT TTT ACA GCG TAT TCC TTA TAT GAT GCG AGA AAT GTC ATT AAA AAT          2976
Ile Phe Thr Ala Tyr Ser Leu Tyr Asp Ala Arg Asn Val Ile Lys Asn
                980                 985                 990

GGC GAT TTC AAT AAT GGC TTA TTA TGC TGG AAC GTG AAA GGT CAT GTA          3024
Gly Asp Phe Asn Asn Gly Leu Leu Cys Trp Asn Val Lys Gly His Val
            995                 1000                1005

GAT GTA GAA GAG CAA AAC AAC CAC CGT TCG GTC CTT GTT ATC CCA GAA          3072
```

```
Asp Val Glu Gln Asn Asn His Arg Ser Val Leu Val Ile Pro Glu
    1010                1015                1020

TGG GAG GCA GAA GTG TCA CAA GAG GTT CGT GTC TGT CCA GGT CGT GGC         3120
Trp Glu Ala Glu Val Ser Gln Glu Val Arg Val Cys Pro Gly Arg Gly
1025                1030                1035                1040

TAT ATC CTT CGT GTC ACA GCA TAT AAA GAG GGA TAT GGA GAG GGC TGC         3168
Tyr Ile Leu Arg Val Thr Ala Tyr Lys Glu Gly Tyr Gly Glu Gly Cys
                1045                1050                1055

GTA ACG ATC CAT GAG ATC GAA GAC AAT ACA GAC GAA CTG AAA TTC AGC         3216
Val Thr Ile His Glu Ile Glu Asp Asn Thr Asp Glu Leu Lys Phe Ser
            1060                1065                1070

AAC TGT GTA GAA GAG GAA GTA TAT CCA AAC AAC ACA GTA ACG TGT AAT         3264
Asn Cys Val Glu Glu Glu Val Tyr Pro Asn Asn Thr Val Thr Cys Asn
        1075                1080                1085

AAT TAT ACT GGG ACT CAA GAA GAA TAT GAG GGT ACG TAC ACT TCT CGT         3312
Asn Tyr Thr Gly Thr Gln Glu Glu Tyr Glu Gly Thr Tyr Thr Ser Arg
    1090                1095                1100

AAT CAA GGA TAT GAC GAA GCC TAT GGT AAT AAC CCT TCC GTA CCA GCT         3360
Asn Gln Gly Tyr Asp Glu Ala Tyr Gly Asn Asn Pro Ser Val Pro Ala
1105                1110                1115                1120

GAT TAC GCT TCA GTC TAT GAA GAA AAA TCG TAT ACA GAT GGA CGA AGA         3408
Asp Tyr Ala Ser Val Tyr Glu Glu Lys Ser Tyr Thr Asp Gly Arg Arg
                1125                1130                1135

GAG AAT CCT TGT GAA TCT AAC AGA GGC TAT GGG GAT TAC ACA CCA CTA         3456
Glu Asn Pro Cys Glu Ser Asn Arg Gly Tyr Gly Asp Tyr Thr Pro Leu
            1140                1145                1150

CCG GCT GGT TAT GTA ACA AAG GAT TTA GAG TAC TTC CCA GAG ACC GAT         3504
Pro Ala Gly Tyr Val Thr Lys Asp Leu Glu Tyr Phe Pro Glu Thr Asp
        1155                1160                1165

AAG GTA TGG ATT GAG ATC GGA GAA ACA GAA GGA ACA TTC ATC GTG GAT         3552
Lys Val Trp Ile Glu Ile Gly Glu Thr Glu Gly Thr Phe Ile Val Asp
    1170                1175                1180

AGC GTG GAA TTA CTC CTT ATG GAG GAA                                     3579
Ser Val Glu Leu Leu Leu Met Glu Glu
1185                1190

(2) INFORMATION FOR SEQ ID NO: 8:

(i) SEQUENCE CHARACTERISTICS:
        (A) LENGTH: 1193 amino acids
        (B) TYPE: amino acid
        (D) TOPOLOGY: linear (ii) MOLECULE TYPE: protein (xi) SEQUENCE DESCRIPTION: SEQ ID NO: 8:

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110
```

-continued

```
Ser Phe Arg Glu Trp Glu Ala Asp Pro Thr Asn Pro Ala Leu Arg Glu
    115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                    165                 170                 175
Val Phe Gly Gln Arg Trp Gly Phe Asp Ala Ala Thr Ile Asn Ser Arg
                180                 185                 190
Tyr Asn Asp Leu Thr Arg Leu Ile Gly Asn Tyr Thr Asp His Ala Val
            195                 200                 205
Arg Trp Tyr Asn Thr Gly Leu Glu Arg Val Trp Gly Pro Asp Ser Arg
        210                 215                 220
Asp Trp Ile Arg Tyr Asn Gln Phe Arg Arg Glu Leu Thr Leu Thr Val
225                 230                 235                 240
Leu Asp Ile Val Ser Leu Phe Pro Asn Tyr Asp Ser Arg Thr Tyr Pro
                    245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
            275                 280                 285
Gly Ser Ile Arg Ser Pro His Leu Met Asp Ile Leu Asn Ser Ile Thr
        290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                    325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
        370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                    405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Thr Leu Thr Asn
        450                 455                 460
Thr Ile Asp Pro Glu Arg Ile Asn Gln Ile Pro Leu Val Lys Gly Phe
465                 470                 475                 480
Arg Val Trp Gly Gly Thr Ser Val Ile Thr Gly Pro Gly Phe Thr Gly
                    485                 490                 495
Gly Asp Ile Leu Arg Arg Asn Thr Phe Gly Asp Phe Val Ser Leu Gln
                500                 505                 510
Val Asn Ile Asn Ser Pro Ile Thr Gln Arg Tyr Arg Leu Arg Phe Arg
            515                 520                 525
```

```
Tyr Ala Ser Ser Arg Asp Ala Arg Val Ile Val Leu Thr Gly Ala Ala
    530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
            580                 585                 590

Ile Ser Glu Gln Pro Leu Phe Gly Ala Gly Ser Ile Ser Ser Gly Glu
    595                 600                 605

Leu Tyr Ile Asp Lys Ile Glu Ile Ile Leu Ala Asp Ala Thr Phe Glu
    610                 615                 620

Ala Glu Ser Asp Leu Glu Arg Ala Gln Lys Ala Val Asn Ala Leu Phe
625                 630                 635                 640

Thr Ser Ser Asn Gln Ile Gly Leu Lys Thr Asp Val Thr Asp Tyr His
                645                 650                 655

Ile Asp Gln Val Ser Asn Leu Val Asp Cys Leu Ser Asp Glu Phe Cys
            660                 665                 670

Leu Asp Glu Lys Arg Glu Leu Ser Glu Lys Val Lys His Ala Lys Arg
    675                 680                 685

Leu Ser Asp Glu Arg Asn Leu Leu Gln Asp Pro Asn Phe Arg Gly Ile
    690                 695                 700

Asn Arg Gln Pro Asp Arg Gly Trp Arg Gly Ser Thr Asp Ile Thr Ile
705                 710                 715                 720

Gln Gly Gly Asp Asp Val Phe Lys Glu Asn Tyr Val Thr Leu Pro Gly
                725                 730                 735

Thr Val Asp Glu Cys Tyr Pro Thr Tyr Leu Tyr Gln Lys Ile Asp Glu
            740                 745                 750

Ser Lys Leu Lys Ala Tyr Thr Arg Tyr Glu Leu Arg Gly Tyr Ile Glu
    755                 760                 765

Asp Ser Gln Asp Leu Glu Ile Tyr Leu Ile Arg Tyr Asn Ala Lys His
    770                 775                 780

Glu Ile Val Asn Val Pro Gly Thr Gly Ser Leu Trp Pro Leu Ser Ala
785                 790                 795                 800

Gln Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
            820                 825                 830

Cys Ala His His Ser His Phe Thr Leu Asp Ile Asp Val Gly Cys
    835                 840                 845

Thr Asp Leu Asn Glu Asp Leu Gly Val Trp Val Ile Phe Lys Ile Lys
850                 855                 860

Thr Gln Asp Gly His Ala Arg Leu Gly Asn Leu Glu Phe Leu Glu Glu
865                 870                 875                 880

Lys Pro Leu Leu Gly Glu Ala Leu Ala Arg Val Lys Arg Ala Glu Lys
                885                 890                 895

Lys Trp Arg Asp Lys Arg Glu Lys Leu Gln Leu Glu Thr Asn Ile Val
            900                 905                 910

Tyr Lys Glu Ala Lys Glu Ser Val Asp Ala Leu Phe Val Asn Ser Gln
    915                 920                 925

Tyr Asp Arg Leu Gln Val Asp Thr Asn Ile Ala Met Ile His Ala Ala
    930                 935                 940

Asp Lys Arg Val His Arg Ile Arg Glu Ala Tyr Leu Pro Glu Leu Ser
```

-continued

```
945                 950                 955                 960
Val Ile Pro Gly Val Asn Ala Ala Ile Phe Glu Glu Leu Glu Gly Arg
                965                 970                 975

Ile Phe Thr Ala Tyr Ser Leu Tyr Asp Ala Arg Asn Val Ile Lys Asn
            980                 985                 990

Gly Asp Phe Asn Asn Gly Leu Leu Cys Trp Asn Val Lys Gly His Val
        995                 1000                1005

Asp Val Glu Glu Gln Asn Asn His Arg Ser Val Leu Val Ile Pro Glu
    1010                1015                1020

Trp Glu Ala Glu Val Ser Gln Glu Val Arg Val Cys Pro Gly Arg Gly
1025                1030                1035                1040

Tyr Ile Leu Arg Val Thr Ala Tyr Lys Glu Gly Tyr Gly Glu Gly Cys
                1045                1050                1055

Val Thr Ile His Glu Ile Glu Asp Asn Thr Asp Glu Leu Lys Phe Ser
            1060                1065                1070

Asn Cys Val Glu Glu Glu Val Tyr Pro Asn Asn Thr Val Thr Cys Asn
        1075                1080                1085

Asn Tyr Thr Gly Thr Gln Glu Glu Tyr Glu Gly Thr Tyr Thr Ser Arg
    1090                1095                1100

Asn Gln Gly Tyr Asp Glu Ala Tyr Gly Asn Asn Pro Ser Val Pro Ala
1105                1110                1115                1120

Asp Tyr Ala Ser Val Tyr Glu Glu Lys Ser Tyr Thr Asp Gly Arg Arg
                1125                1130                1135

Glu Asn Pro Cys Glu Ser Asn Arg Gly Tyr Gly Asp Tyr Thr Pro Leu
            1140                1145                1150

Pro Ala Gly Tyr Val Thr Lys Asp Leu Glu Tyr Phe Pro Glu Thr Asp
        1155                1160                1165

Lys Val Trp Ile Glu Ile Gly Glu Thr Glu Gly Thr Phe Ile Val Asp
    1170                1175                1180

Ser Val Glu Leu Leu Leu Met Glu Glu
1185                1190
```

(2) INFORMATION FOR SEQ ID NO:9:

(i) SEQUENCE CHARACTERISTICS:
(A) LENGTH: 3468 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Bacillus thuringiensis (ix) FEATURE:
(A) NAME/KEY: CDS
(B) LOCATION: 1..3468

(xi) SEQUENCE DESCRIPTION: SEQ ID NO:9:

```
ATG AAT CAA AAT AAA CAC GGA ATT ATT GGC GCT TCC AAT TGT GGT TGT       48
Met Asn Gln Asn Lys His Gly Ile Ile Gly Ala Ser Asn Cys Gly Cys
  1               5                  10                  15

GCA TCT GAT GAT GTT GCG AAA TAT CCT TTA GCC AAC AAT CCA TAT TCA       96
Ala Ser Asp Asp Val Ala Lys Tyr Pro Leu Ala Asn Asn Pro Tyr Ser
            20                  25                  30

TCT GCT TTA AAT TTA AAT TCT TGT CAA AAT AGT AGT ATT CTC AAC TGG      144
Ser Ala Leu Asn Leu Asn Ser Cys Gln Asn Ser Ser Ile Leu Asn Trp
        35                  40                  45
```

-continued

```
ATT AAC ATA ATA GGC GAT GCA GCA AAA GAA GCA GTA TCT ATT GGG ACA        192
Ile Asn Ile Ile Gly Asp Ala Ala Lys Glu Ala Val Ser Ile Gly Thr
    50                  55                  60

ACC ATA GTC TCT CTT ATC ACA GCA CCT TCT CTT ACT GGA TTA ATT TCA        240
Thr Ile Val Ser Leu Ile Thr Ala Pro Ser Leu Thr Gly Leu Ile Ser
65                  70                  75                  80

ATA GTA TAT GAC CTT ATA GGT AAA GTA CTA GGA GGT AGT AGT GGA CAA        288
Ile Val Tyr Asp Leu Ile Gly Lys Val Leu Gly Gly Ser Ser Gly Gln
                85                  90                  95

TCC ATA TCA GAT TTG TCT ATA TGT GAC TTA TTA TCT ATT ATT GAT TTA        336
Ser Ile Ser Asp Leu Ser Ile Cys Asp Leu Leu Ser Ile Ile Asp Leu
            100                 105                 110

CGG GTA AGT CAG AGT GTT TTA AAT GAT GGG ATT GCA GAT TTT AAT GGT        384
Arg Val Ser Gln Ser Val Leu Asn Asp Gly Ile Ala Asp Phe Asn Gly
        115                 120                 125

TCT GTA CTC TTA TAC AGG AAC TAT TTA GAG GCT CTG GAT AGC TGG AAT        432
Ser Val Leu Leu Tyr Arg Asn Tyr Leu Glu Ala Leu Asp Ser Trp Asn
    130                 135                 140

AAG AAT CCT AAT TCT GCT TCT GCT GAA GAA CTC CGT ACT CGT TTT AGA        480
Lys Asn Pro Asn Ser Ala Ser Ala Glu Glu Leu Arg Thr Arg Phe Arg
145                 150                 155                 160

ATC GCC GAC TCA GAA TTT GAT AGA ATT TTA ACC CGA GGG TCT TTA ACG        528
Ile Ala Asp Ser Glu Phe Asp Arg Ile Leu Thr Arg Gly Ser Leu Thr
                165                 170                 175

AAT GGT GGC TCG TTA GCT AGA CAA AAT GCC CAA ATA TTA TTA TTA CCT        576
Asn Gly Gly Ser Leu Ala Arg Gln Asn Ala Gln Ile Leu Leu Leu Pro
            180                 185                 190

TCT TTT GCG AGC GCT GCA TTT TTC CAT TTA TTA CTA CTA AGG GAT GCT        624
Ser Phe Ala Ser Ala Ala Phe Phe His Leu Leu Leu Leu Arg Asp Ala
        195                 200                 205

ACT AGA TAT GGC ACT AAT TGG GGG CTA TAC AAT GCT ACA CCT TTT ATA        672
Thr Arg Tyr Gly Thr Asn Trp Gly Leu Tyr Asn Ala Thr Pro Phe Ile
    210                 215                 220

AAT TAT CAA TCA AAA CTA GTA GAG CTT ATT GAA CTA TAT ACT GAT TAT        720
Asn Tyr Gln Ser Lys Leu Val Glu Leu Ile Glu Leu Tyr Thr Asp Tyr
225                 230                 235                 240

TGC GTA CAT TGG TAT AAT CGA GGT TTC AAC GAA CTA AGA CAA CGA GGC        768
Cys Val His Trp Tyr Asn Arg Gly Phe Asn Glu Leu Arg Gln Arg Gly
                245                 250                 255

ACT AGT GCT ACA GCT TGG TTA GAA TTT CAT AGA TAT CGT AGA GAG ATG        816
Thr Ser Ala Thr Ala Trp Leu Glu Phe His Arg Tyr Arg Arg Glu Met
            260                 265                 270

ACA TTG ATG GTA TTA GAT ATA GTA GCA TCA TTT TCA AGT CTT GAT ATT        864
Thr Leu Met Val Leu Asp Ile Val Ala Ser Phe Ser Ser Leu Asp Ile
        275                 280                 285

ACT AAT TAC CCA ATA GAA ACA GAT TTT CAG TTG AGT AGG GTC ATT TAT        912
Thr Asn Tyr Pro Ile Glu Thr Asp Phe Gln Leu Ser Arg Val Ile Tyr
    290                 295                 300

ACA GAT CCA ATT GGT TTT GTA CAT CGT AGT AGT CTT AGG GGA GAA AGT        960
Thr Asp Pro Ile Gly Phe Val His Arg Ser Ser Leu Arg Gly Glu Ser
305                 310                 315                 320

TGG TTT AGC TTT GTT AAT AGA GCT AAT TTC TCA GAT TTA GAA AAT GCA       1008
Trp Phe Ser Phe Val Asn Arg Ala Asn Phe Ser Asp Leu Glu Asn Ala
                325                 330                 335

ATA CCT AAT CCT AGA CCG TCT TGG TTT TTA AAT AAT ATG ATT ATA TCT       1056
Ile Pro Asn Pro Arg Pro Ser Trp Phe Leu Asn Asn Met Ile Ile Ser
            340                 345                 350

ACT GGT TCA CTT ACA TTG CCG GTT AGC CCA AGT ACT GAT AGA GCG AGG       1104
Thr Gly Ser Leu Thr Leu Pro Val Ser Pro Ser Thr Asp Arg Ala Arg
        355                 360                 365
```

```
GTA TGG TAT GGA AGT CGA GAT CGA ATT TCC CCT GCT AAT TCA CAA TTT    1152
Val Trp Tyr Gly Ser Arg Asp Arg Ile Ser Pro Ala Asn Ser Gln Phe
    370                 375                 380

ATT ACT GAA CTA ATC TCT GGA CAA CAT ACG ACT GCT ACA CAA ACT ATT    1200
Ile Thr Glu Leu Ile Ser Gly Gln His Thr Thr Ala Thr Gln Thr Ile
385                 390                 395                 400

TTA GGG CGA AAT ATA TTT AGA GTA GAT TCT CAA GCT TGT AAT TTA AAT    1248
Leu Gly Arg Asn Ile Phe Arg Val Asp Ser Gln Ala Cys Asn Leu Asn
                405                 410                 415

GAT ACC ACA TAT GGA GTG AAT AGG GCG GTA TTT TAT CAT GAT GCG AGT    1296
Asp Thr Thr Tyr Gly Val Asn Arg Ala Val Phe Tyr His Asp Ala Ser
            420                 425                 430

GAA GGT TCT CAA AGA TCC GTG TAC GAG GGG TAT ATT CGA ACA ACT GGG    1344
Glu Gly Ser Gln Arg Ser Val Tyr Glu Gly Tyr Ile Arg Thr Thr Gly
        435                 440                 445

ATA GAT AAC CCT AGA GTT CAA AAT ATT AAC ACT TAT TTA CCT GGA GAA    1392
Ile Asp Asn Pro Arg Val Gln Asn Ile Asn Thr Tyr Leu Pro Gly Glu
    450                 455                 460

AAT TCA GAT ATC CCA ACT CCA GAA GAC TAT ACT CAT ATA TTA AGC ACA    1440
Asn Ser Asp Ile Pro Thr Pro Glu Asp Tyr Thr His Ile Leu Ser Thr
465                 470                 475                 480

ACA ATA AAT TTA ACA GGA GGA CTT AGA CAA GTA GCA TCT AAT CGC CGT    1488
Thr Ile Asn Leu Thr Gly Gly Leu Arg Gln Val Ala Ser Asn Arg Arg
                485                 490                 495

TCA TCT TTA GTA ATG TAT GGT TGG ACA CAT AAA AGT CTG GCT CGT AAC    1536
Ser Ser Leu Val Met Tyr Gly Trp Thr His Lys Ser Leu Ala Arg Asn
            500                 505                 510

AAT ACC ATT AAT CCA GAT AGA ATT ACA CAG ATA CCA TTG ACG AAG GTT    1584
Asn Thr Ile Asn Pro Asp Arg Ile Thr Gln Ile Pro Leu Thr Lys Val
        515                 520                 525

GAT ACC CGA GGC ACA GGT GTT TCT TAT GTG AAT GAT CCA GGA TTT ATA    1632
Asp Thr Arg Gly Thr Gly Val Ser Tyr Val Asn Asp Pro Gly Phe Ile
    530                 535                 540

GGA GGA GCT CTA CTT CAA AGG ACT GAC CAT GGT TCG CTT GGA GTA TTG    1680
Gly Gly Ala Leu Leu Gln Arg Thr Asp His Gly Ser Leu Gly Val Leu
545                 550                 555                 560

AGG GTC CAA TTT CCA CTT CAC TTA AGA CAA CAA TAT CGT ATT AGA GTC    1728
Arg Val Gln Phe Pro Leu His Leu Arg Gln Gln Tyr Arg Ile Arg Val
                565                 570                 575

CGT TAT GCT TCT ACA ACA AAT ATT CGA TTG AGT GTG AAT GGC AGT TTC    1776
Arg Tyr Ala Ser Thr Thr Asn Ile Arg Leu Ser Val Asn Gly Ser Phe
            580                 585                 590

GGT ACT ATT TCT CAA AAT CTC CCT AGT ACA ATG AGA TTA GGA GAG GAT    1824
Gly Thr Ile Ser Gln Asn Leu Pro Ser Thr Met Arg Leu Gly Glu Asp
        595                 600                 605

TTA AGA TAC GGA TCT TTT GCT ATA AGA GAG TTT AAT ACT TCT ATT AGA    1872
Leu Arg Tyr Gly Ser Phe Ala Ile Arg Glu Phe Asn Thr Ser Ile Arg
    610                 615                 620

CCC ACT GCA AGT CCG GAC CAA ATT CGA TTG ACA ATA GAA CCA TCT TTT    1920
Pro Thr Ala Ser Pro Asp Gln Ile Arg Leu Thr Ile Glu Pro Ser Phe
625                 630                 635                 640

ATT AGA CAA GAG GTC TAT GTA GAT AGA ATT GAG TTC ATT CCA GTT AAT    1968
Ile Arg Gln Glu Val Tyr Val Asp Arg Ile Glu Phe Ile Pro Val Asn
                645                 650                 655

CCG ACG CGA GAG GCG AAA GAG GAT CTA GAA GCA GCA AAA AAA GCG GTG    2016
Pro Thr Arg Glu Ala Lys Glu Asp Leu Glu Ala Ala Lys Lys Ala Val
            660                 665                 670

GCG AGC TTG TTT ACA CGC ACA AGG GAC GGA TTA CAA GTA AAT GTG AAA    2064
Ala Ser Leu Phe Thr Arg Thr Arg Asp Gly Leu Gln Val Asn Val Lys
```

|  |  |  |  |  |  |  |  |  |  |  |  |  |  |  |  |  |
|---|---|---|---|---|---|---|---|---|---|---|---|---|---|---|---|---|
|  | 675 |  |  |  |  | 680 |  |  |  |  |  | 685 |  |  |  |  |
| GAT | TAT | CAA | GTC | GAT | CAA | GCG | GCA | AAT | TTA | GTG | TCA | TGC | TTA | TCA | GAT | 2112 |
| Asp | Tyr | Gln | Val | Asp | Gln | Ala | Ala | Asn | Leu | Val | Ser | Cys | Leu | Ser | Asp |  |
|  | 690 |  |  |  | 695 |  |  |  |  | 700 |  |  |  |  |  |  |
| GAA | CAA | TAT | GGG | TAT | GAC | AAA | AAG | ATG | TTA | TTG | GAA | GCG | GTA | CGT | GCG | 2160 |
| Glu | Gln | Tyr | Gly | Tyr | Asp | Lys | Lys | Met | Leu | Leu | Glu | Ala | Val | Arg | Ala |  |
| 705 |  |  |  |  | 710 |  |  |  |  | 715 |  |  |  |  | 720 |  |
| GCA | AAA | CGA | CTT | AGC | CGA | GAA | CGC | AAC | TTA | CTT | CAG | GAT | CCA | GAT | TTT | 2208 |
| Ala | Lys | Arg | Leu | Ser | Arg | Glu | Arg | Asn | Leu | Leu | Gln | Asp | Pro | Asp | Phe |  |
|  |  |  |  |  | 725 |  |  |  |  | 730 |  |  |  |  | 735 |  |
| AAT | ACA | ATC | AAT | AGT | ACA | GAA | GAA | AAT | GGA | TGG | AAA | GCA | AGT | AAC | GGC | 2256 |
| Asn | Thr | Ile | Asn | Ser | Thr | Glu | Glu | Asn | Gly | Trp | Lys | Ala | Ser | Asn | Gly |  |
|  |  |  |  | 740 |  |  |  |  | 745 |  |  |  |  | 750 |  |  |
| GTT | ACT | ATT | AGT | GAG | GGC | GGG | CCA | TTC | TAT | AAA | GGC | CGT | GCA | ATT | CAG | 2304 |
| Val | Thr | Ile | Ser | Glu | Gly | Gly | Pro | Phe | Tyr | Lys | Gly | Arg | Ala | Ile | Gln |  |
|  |  |  | 755 |  |  |  |  | 760 |  |  |  |  | 765 |  |  |  |
| CTA | GCA | AGT | GCA | CGA | GAA | AAT | TAC | CCA | ACA | TAC | ATC | TAT | CAA | AAA | GTA | 2352 |
| Leu | Ala | Ser | Ala | Arg | Glu | Asn | Tyr | Pro | Thr | Tyr | Ile | Tyr | Gln | Lys | Val |  |
|  |  | 770 |  |  |  |  | 775 |  |  |  |  | 780 |  |  |  |  |
| GAT | GCA | TCG | GAG | TTA | AAG | CCG | TAT | ACA | CGT | TAT | AGA | CTG | GAT | GGG | TTC | 2400 |
| Asp | Ala | Ser | Glu | Leu | Lys | Pro | Tyr | Thr | Arg | Tyr | Arg | Leu | Asp | Gly | Phe |  |
| 785 |  |  |  | 790 |  |  |  |  | 795 |  |  |  |  | 800 |  |  |
| GTG | AAG | AGT | AGT | CAA | GAT | TTA | GAA | ATT | GAT | CTC | ATT | CAC | CAT | CAT | AAA | 2448 |
| Val | Lys | Ser | Ser | Gln | Asp | Leu | Glu | Ile | Asp | Leu | Ile | His | His | His | Lys |  |
|  |  |  | 805 |  |  |  |  | 810 |  |  |  |  | 815 |  |  |  |
| GTC | CAT | CTT | GTG | AAA | AAT | GTA | CCA | GAT | AAT | TTA | GTA | TCT | GAT | ACT | TAC | 2496 |
| Val | His | Leu | Val | Lys | Asn | Val | Pro | Asp | Asn | Leu | Val | Ser | Asp | Thr | Tyr |  |
|  |  | 820 |  |  |  |  | 825 |  |  |  |  | 830 |  |  |  |  |
| CCA | GAT | GAT | TCT | TGT | AGT | GGA | ATC | AAT | CGA | TGT | CAG | GAA | CAA | CAG | ATG | 2544 |
| Pro | Asp | Asp | Ser | Cys | Ser | Gly | Ile | Asn | Arg | Cys | Gln | Glu | Gln | Gln | Met |  |
|  | 835 |  |  |  |  | 840 |  |  |  |  | 845 |  |  |  |  |  |
| GTA | AAT | GCG | CAA | CTG | GAA | ACA | GAG | CAT | CAT | CAT | CCG | ATG | GAT | TGC | TGT | 2592 |
| Val | Asn | Ala | Gln | Leu | Glu | Thr | Glu | His | His | His | Pro | Met | Asp | Cys | Cys |  |
|  | 850 |  |  |  |  | 855 |  |  |  |  | 860 |  |  |  |  |  |
| GAA | GCA | GCT | CAA | ACA | CAT | GAG | TTT | TCT | TCC | TAT | ATT | GAT | ACA | GGG | GAT | 2640 |
| Glu | Ala | Ala | Gln | Thr | His | Glu | Phe | Ser | Ser | Tyr | Ile | Asp | Thr | Gly | Asp |  |
| 865 |  |  |  | 870 |  |  |  |  | 875 |  |  |  |  | 880 |  |  |
| TTA | AAT | TCG | AGT | GTA | GAC | CAG | GGA | ATC | TGG | GCG | ATC | TTT | AAA | GTT | CGA | 2688 |
| Leu | Asn | Ser | Ser | Val | Asp | Gln | Gly | Ile | Trp | Ala | Ile | Phe | Lys | Val | Arg |  |
|  |  |  | 885 |  |  |  |  | 890 |  |  |  |  | 895 |  |  |  |
| ACA | ACC | GAT | GGT | TAT | GCG | ACG | TTA | GGA | AAT | CTT | GAA | TTG | GTA | GAG | GTC | 2736 |
| Thr | Thr | Asp | Gly | Tyr | Ala | Thr | Leu | Gly | Asn | Leu | Glu | Leu | Val | Glu | Val |  |
|  |  |  | 900 |  |  |  |  | 905 |  |  |  |  | 910 |  |  |  |
| GGA | CCG | TTA | TCG | GGT | GAA | TCT | TTA | GAA | CGT | GAA | CAA | AGG | GAT | AAT | ACA | 2784 |
| Gly | Pro | Leu | Ser | Gly | Glu | Ser | Leu | Glu | Arg | Glu | Gln | Arg | Asp | Asn | Thr |  |
|  |  | 915 |  |  |  |  | 920 |  |  |  |  | 925 |  |  |  |  |
| AAA | TGG | AGT | GCA | GAG | CTA | GGA | AGA | AAG | CGT | GCA | GAA | ACA | GAT | CGC | GTG | 2832 |
| Lys | Trp | Ser | Ala | Glu | Leu | Gly | Arg | Lys | Arg | Ala | Glu | Thr | Asp | Arg | Val |  |
| 930 |  |  |  |  | 935 |  |  |  |  | 940 |  |  |  |  |  |  |
| TAT | CAA | GAT | GCC | AAA | CAA | TCC | ATC | AAT | CAT | TTA | TTT | GTG | GAT | TAT | CAA | 2880 |
| Tyr | Gln | Asp | Ala | Lys | Gln | Ser | Ile | Asn | His | Leu | Phe | Val | Asp | Tyr | Gln |  |
| 945 |  |  |  |  | 950 |  |  |  |  | 955 |  |  |  |  | 960 |  |
| GAT | CAA | CAA | TTA | AAT | CCA | GAA | ATA | GGG | ATG | GCA | GAT | ATT | ATG | GAC | GCT | 2928 |
| Asp | Gln | Gln | Leu | Asn | Pro | Glu | Ile | Gly | Met | Ala | Asp | Ile | Met | Asp | Ala |  |
|  |  |  |  | 965 |  |  |  |  | 970 |  |  |  |  | 975 |  |  |
| CAA | AAT | CTT | GTC | GCA | TCA | ATT | TCA | GAT | GTA | TAT | AGC | GAT | GCC | GTA | CTG | 2976 |
| Gln | Asn | Leu | Val | Ala | Ser | Ile | Ser | Asp | Val | Tyr | Ser | Asp | Ala | Val | Leu |  |
|  |  |  | 980 |  |  |  |  | 985 |  |  |  |  | 990 |  |  |  |
| CAA | ATC | CCT | GGA | ATT | AAC | TAT | GAG | ATT | TAC | ACA | GAG | CTG | TCC | AAT | CGC | 3024 |

```
Gln Ile Pro Gly Ile Asn Tyr Glu Ile Tyr Thr Glu Leu Ser Asn Arg
        995                 1000                1005

TTA CAA CAA GCA TCG TAT CTG TAT ACG TCT CGA AAT GCG GTG CAA AAT     3072
Leu Gln Gln Ala Ser Tyr Leu Tyr Thr Ser Arg Asn Ala Val Gln Asn
            1010                1015                1020

GGG GAC TTT AAC AAC GGG CTA GAT AGC TGG AAT GCA ACA GCG GGT GCA     3120
Gly Asp Phe Asn Asn Gly Leu Asp Ser Trp Asn Ala Thr Ala Gly Ala
1025                1030                1035                1040

TCG GTA CAA CAG GAT GGC AAT ACG CAT TTC TTA GTT CTT TCT CAT TGG     3168
Ser Val Gln Gln Asp Gly Asn Thr His Phe Leu Val Leu Ser His Trp
                1045                1050                1055

GAT GCA CAA GTT TCT CAA CAA TTT AGA GTG CAG CCG AAT TGT AAA TAT     3216
Asp Ala Gln Val Ser Gln Gln Phe Arg Val Gln Pro Asn Cys Lys Tyr
            1060                1065                1070

GTA TTA CGT GTA ACA GCA GAG AAA GTA GGC GGC GGA GAC GGA TAC GTG     3264
Val Leu Arg Val Thr Ala Glu Lys Val Gly Gly Gly Asp Gly Tyr Val
        1075                1080                1085

ACT ATC CGG GAT GAT GCT CAT CAT ACA GAA ACG CTT ACA TTT AAT GCA     3312
Thr Ile Arg Asp Asp Ala His His Thr Glu Thr Leu Thr Phe Asn Ala
    1090                1095                1100

TGT GAT TAT GAT ATA AAT GGC ACG TAC GTG ACT GAT AAT ACG TAT CTA     3360
Cys Asp Tyr Asp Ile Asn Gly Thr Tyr Val Thr Asp Asn Thr Tyr Leu
1105                1110                1115                1120

ACA AAA GAA GTG GTA TTC CAT CCG GAG ACA CAA CAC ATG TGG GTA GAG     3408
Thr Lys Glu Val Val Phe His Pro Glu Thr Gln His Met Trp Val Glu
                1125                1130                1135

GTA AAT GAA ACA GAA GGT GCA TTT CAT ATA GAT AGT ATT GAA TTC GTT     3456
Val Asn Glu Thr Glu Gly Ala Phe His Ile Asp Ser Ile Glu Phe Val
            1140                1145                1150

GAA ACA GAA AAG                                                     3468
Glu Thr Glu Lys
        1155

(2) INFORMATION FOR SEQ ID NO:10:

(i) SEQUENCE CHARACTERISTICS:
        (A) LENGTH: 1156 amino acids
        (B) TYPE: amino acid
        (D) TOPOLOGY: linear (ii) MOLECULE TYPE: protein (xi) SEQUENCE DESCRIPTION: SEQ ID NO:10:

Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125
```

-continued

```
Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
```

-continued

```
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
                580                 585                 590

Gly Thr Ile Ser Gln Asn Leu Pro Ser Thr Met Arg Leu Gly Glu Asp
                595                 600                 605

Leu Arg Tyr Gly Ser Phe Ala Ile Arg Glu Phe Asn Thr Ser Ile Arg
                610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
                660                 665                 670

Ala Ser Leu Phe Thr Arg Thr Arg Asp Gly Leu Gln Val Asn Val Lys
                675                 680                 685

Asp Tyr Gln Val Asp Gln Ala Ala Asn Leu Val Ser Cys Leu Ser Asp
                690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
                740                 745                 750

Val Thr Ile Ser Glu Gly Gly Pro Phe Tyr Lys Gly Arg Ala Ile Gln
                755                 760                 765

Leu Ala Ser Ala Arg Glu Asn Tyr Pro Thr Tyr Ile Tyr Gln Lys Val
                770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His Lys
                805                 810                 815

Val His Leu Val Lys Asn Val Pro Asp Asn Leu Val Ser Asp Thr Tyr
                820                 825                 830

Pro Asp Asp Ser Cys Ser Gly Ile Asn Arg Cys Gln Glu Gln Gln Met
                835                 840                 845

Val Asn Ala Gln Leu Glu Thr Glu His His Pro Met Asp Cys Cys
850                 855                 860

Glu Ala Ala Gln Thr His Glu Phe Ser Ser Tyr Ile Asp Thr Gly Asp
865                 870                 875                 880

Leu Asn Ser Ser Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Val
                900                 905                 910

Gly Pro Leu Ser Gly Glu Ser Leu Glu Arg Glu Gln Arg Asp Asn Thr
                915                 920                 925

Lys Trp Ser Ala Glu Leu Gly Arg Lys Arg Ala Glu Thr Asp Arg Val
                930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975
```

```
Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
        995                 1000                1005

Leu Gln Gln Ala Ser Tyr Leu Tyr Thr Ser Arg Asn Ala Val Gln Asn
    1010                1015                1020

Gly Asp Phe Asn Asn Gly Leu Asp Ser Trp Asn Ala Thr Ala Gly Ala
1025                1030                1035                1040

Ser Val Gln Gln Asp Gly Asn Thr His Phe Leu Val Leu Ser His Trp
                1045                1050                1055

Asp Ala Gln Val Ser Gln Gln Phe Arg Val Gln Pro Asn Cys Lys Tyr
            1060                1065                1070

Val Leu Arg Val Thr Ala Glu Lys Val Gly Gly Asp Gly Tyr Val
            1075                1080                1085

Thr Ile Arg Asp Asp Ala His His Thr Glu Thr Leu Thr Phe Asn Ala
        1090                1095                1100

Cys Asp Tyr Asp Ile Asn Gly Thr Tyr Val Thr Asp Asn Thr Tyr Leu
1105                1110                1115                1120

Thr Lys Glu Val Val Phe His Pro Glu Thr Gln His Met Trp Val Glu
                1125                1130                1135

Val Asn Glu Thr Glu Gly Ala Phe His Ile Asp Ser Ile Glu Phe Val
                1140                1145                1150

Glu Thr Glu Lys
        1155

(2) INFORMATION FOR SEQ ID NO:11:

(i) SEQUENCE CHARACTERISTICS:
        (A) LENGTH: 3726 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..3726

(xi) SEQUENCE DESCRIPTION: SEQ ID NO:11:

ATG AAT CAA AAT AAA CAC GGA ATT ATT GGC GCT TCC AAT TGT GGT TGT        48
Met Asn Gln Asn Lys His Gly Ile Ile Gly Ala Ser Asn Cys Gly Cys
  1               5                  10                  15

GCA TCT GAT GAT GTT GCG AAA TAT CCT TTA GCC AAC AAT CCA TAT TCA        96
Ala Ser Asp Asp Val Ala Lys Tyr Pro Leu Ala Asn Asn Pro Tyr Ser
             20                  25                  30

TCT GCT TTA AAT TTA AAT TCT TGT CAA AAT AGT AGT ATT CTC AAC TGG       144
Ser Ala Leu Asn Leu Asn Ser Cys Gln Asn Ser Ser Ile Leu Asn Trp
         35                  40                  45

ATT AAC ATA ATA GGC GAT GCA GCA AAA GAA GCA GTA TCT ATT GGG ACA       192
Ile Asn Ile Ile Gly Asp Ala Ala Lys Glu Ala Val Ser Ile Gly Thr
     50                  55                  60

ACC ATA GTC TCT CTT ATC ACA GCA CCT TCT CTT ACT GGA TTA ATT TCA       240
Thr Ile Val Ser Leu Ile Thr Ala Pro Ser Leu Thr Gly Leu Ile Ser
 65                  70                  75                  80

ATA GTA TAT GAC CTT ATA GGT AAA GTA CTA GGA GGT AGT AGT GGA CAA       288
Ile Val Tyr Asp Leu Ile Gly Lys Val Leu Gly Gly Ser Ser Gly Gln
                 85                  90                  95

TCC ATA TCA GAT TTG TCT ATA TGT GAC TTA TTA TCT ATT ATT GAT TTA       336
```

```
Ser Ile Ser Asp Leu Ser Ile Cys Asp Leu Leu Ser Ile Ile Asp Leu
            100                 105                 110

CGG GTA AGT CAG AGT GTT TTA AAT GAT GGG ATT GCA GAT TTT AAT GGT        384
Arg Val Ser Gln Ser Val Leu Asn Asp Gly Ile Ala Asp Phe Asn Gly
        115                 120                 125

TCT GTA CTC TTA TAC AGG AAC TAT TTA GAG GCT CTG GAT AGC TGG AAT        432
Ser Val Leu Leu Tyr Arg Asn Tyr Leu Glu Ala Leu Asp Ser Trp Asn
    130                 135                 140

AAG AAT CCT AAT TCT GCT TCT GCT GAA GAA CTC CGT ACT CGT TTT AGA        480
Lys Asn Pro Asn Ser Ala Ser Ala Glu Glu Leu Arg Thr Arg Phe Arg
145                 150                 155                 160

ATC GCC GAC TCA GAA TTT GAT AGA ATT TTA ACC CGA GGG TCT TTA ACG        528
Ile Ala Asp Ser Glu Phe Asp Arg Ile Leu Thr Arg Gly Ser Leu Thr
                165                 170                 175

AAT GGT GGC TCG TTA GCT AGA CAA AAT GCC CAA ATA TTA TTA TTA CCT        576
Asn Gly Gly Ser Leu Ala Arg Gln Asn Ala Gln Ile Leu Leu Leu Pro
            180                 185                 190

TCT TTT GCG AGC GCT GCA TTT TTC CAT TTA TTA CTA CTA AGG GAT GCT        624
Ser Phe Ala Ser Ala Ala Phe Phe His Leu Leu Leu Leu Arg Asp Ala
        195                 200                 205

ACT AGA TAT GGC ACT AAT TGG GGG CTA TAC AAT GCT ACA CCT TTT ATA        672
Thr Arg Tyr Gly Thr Asn Trp Gly Leu Tyr Asn Ala Thr Pro Phe Ile
    210                 215                 220

AAT TAT CAA TCA AAA CTA GTA GAG CTT ATT GAA CTA TAT ACT GAT TAT        720
Asn Tyr Gln Ser Lys Leu Val Glu Leu Ile Glu Leu Tyr Thr Asp Tyr
225                 230                 235                 240

TGC GTA CAT TGG TAT AAT CGA GGT TTC AAC GAA CTA AGA CAA CGA GGC        768
Cys Val His Trp Tyr Asn Arg Gly Phe Asn Glu Leu Arg Gln Arg Gly
                245                 250                 255

ACT AGT GCT ACA GCT TGG TTA GAA TTT CAT AGA TAT CGT AGA GAG ATG        816
Thr Ser Ala Thr Ala Trp Leu Glu Phe His Arg Tyr Arg Arg Glu Met
            260                 265                 270

ACA TTG ATG GTA TTA GAT ATA GTA GCA TCA TTT TCA AGT CTT GAT ATT        864
Thr Leu Met Val Leu Asp Ile Val Ala Ser Phe Ser Ser Leu Asp Ile
        275                 280                 285

ACT AAT TAC CCA ATA GAA ACA GAT TTT CAG TTG AGT AGG GTC ATT TAT        912
Thr Asn Tyr Pro Ile Glu Thr Asp Phe Gln Leu Ser Arg Val Ile Tyr
    290                 295                 300

ACA GAT CCA ATT GGT TTT GTA CAT CGT AGT AGT CTT AGG GGA GAA AGT        960
Thr Asp Pro Ile Gly Phe Val His Arg Ser Ser Leu Arg Gly Glu Ser
305                 310                 315                 320

TGG TTT AGC TTT GTT AAT AGA GCT AAT TTC TCA GAT TTA GAA AAT GCA       1008
Trp Phe Ser Phe Val Asn Arg Ala Asn Phe Ser Asp Leu Glu Asn Ala
                325                 330                 335

ATA CCT AAT CCT AGA CCG TCT TGG TTT TTA AAT AAT ATG ATT ATA TCT       1056
Ile Pro Asn Pro Arg Pro Ser Trp Phe Leu Asn Asn Met Ile Ile Ser
            340                 345                 350

ACT GGT TCA CTT ACA TTG CCG GTT AGC CCA AGT ACT GAT AGA GCG AGG       1104
Thr Gly Ser Leu Thr Leu Pro Val Ser Pro Ser Thr Asp Arg Ala Arg
        355                 360                 365

GTA TGG TAT GGA AGT CGA GAT CGA ATT TCC CCT GCT AAT TCA CAA TTT       1152
Val Trp Tyr Gly Ser Arg Asp Arg Ile Ser Pro Ala Asn Ser Gln Phe
    370                 375                 380

ATT ACT GAA CTA ATC TCT GGA CAA CAT ACG ACT GCT ACA CAA ACT ATT       1200
Ile Thr Glu Leu Ile Ser Gly Gln His Thr Thr Ala Thr Gln Thr Ile
385                 390                 395                 400

TTA GGG CGA AAT ATA TTT AGA GTA GAT TCT CAA GCT TGT AAT TTA AAT       1248
Leu Gly Arg Asn Ile Phe Arg Val Asp Ser Gln Ala Cys Asn Leu Asn
                405                 410                 415
```

```
GAT ACC ACA TAT GGA GTG AAT AGG GCG GTA TTT TAT CAT GAT GCG AGT     1296
Asp Thr Thr Tyr Gly Val Asn Arg Ala Val Phe Tyr His Asp Ala Ser
            420                 425                 430

GAA GGT TCT CAA AGA TCC GTG TAC GAG GGG TAT ATT CGA ACA ACT GGG     1344
Glu Gly Ser Gln Arg Ser Val Tyr Glu Gly Tyr Ile Arg Thr Thr Gly
            435                 440                 445

ATA GAT AAC CCT AGA GTT CAA AAT ATT AAC ACT TAT TTA CCT GGA GAA     1392
Ile Asp Asn Pro Arg Val Gln Asn Ile Asn Thr Tyr Leu Pro Gly Glu
450                 455                 460

AAT TCA GAT ATC CCA ACT CCA GAA GAC TAT ACT CAT ATA TTA AGC ACA     1440
Asn Ser Asp Ile Pro Thr Pro Glu Asp Tyr Thr His Ile Leu Ser Thr
465                 470                 475                 480

ACA ATA AAT TTA ACA GGA GGA CTT AGA CAA GTA GCA TCT AAT CGC CGT     1488
Thr Ile Asn Leu Thr Gly Gly Leu Arg Gln Val Ala Ser Asn Arg Arg
            485                 490                 495

TCA TCT TTA GTA ATG TAT GGT TGG ACA CAT AAA AGT CTG GCT CGT AAC     1536
Ser Ser Leu Val Met Tyr Gly Trp Thr His Lys Ser Leu Ala Arg Asn
            500                 505                 510

AAT ACC ATT AAT CCA GAT AGA ATT ACA CAG ATA CCT TTA GTG AAA GGA     1584
Asn Thr Ile Asn Pro Asp Arg Ile Thr Gln Ile Pro Leu Val Lys Gly
            515                 520                 525

TTT AGA GTT TGG GGG GGC ACC TCT GTC ATT ACA GGA CCA GGA TTT ACA     1632
Phe Arg Val Trp Gly Gly Thr Ser Val Ile Thr Gly Pro Gly Phe Thr
530                 535                 540

GGA GGG GAT ATC CTT CGA AGA AAT ACC TTT GGT GAT TTT GTA TCT CTA     1680
Gly Gly Asp Ile Leu Arg Arg Asn Thr Phe Gly Asp Phe Val Ser Leu
545                 550                 555                 560

CAA GTC AAT ATT AAT TCA CCA ATT ACC CAA AGA TAC CGT TTA AGA TTT     1728
Gln Val Asn Ile Asn Ser Pro Ile Thr Gln Arg Tyr Arg Leu Arg Phe
            565                 570                 575

CGT TAC GCT TCC AGT AGG GAT GCA CGA GTT ATA GTA TTA ACA GGA GCG     1776
Arg Tyr Ala Ser Ser Arg Asp Ala Arg Val Ile Val Leu Thr Gly Ala
            580                 585                 590

GCA TCC ACA GGA GTG GGA GGC CAA GTT AGT GTA AAT ATG CCT CTT CAG     1824
Ala Ser Thr Gly Val Gly Gly Gln Val Ser Val Asn Met Pro Leu Gln
            595                 600                 605

AAA ACT ATG GAA ATA GGG GAG AAC TTA ACA TCT AGA ACA TTT AGA TAT     1872
Lys Thr Met Glu Ile Gly Glu Asn Leu Thr Ser Arg Thr Phe Arg Tyr
610                 615                 620

ACC GAT TTT AGT AAT CCT TTT TCA TTT AGA GCT AAT CCA GAT ATA ATT     1920
Thr Asp Phe Ser Asn Pro Phe Ser Phe Arg Ala Asn Pro Asp Ile Ile
625                 630                 635                 640

GGG ATA AGT GAA CAA CCT CTA TTT GGT GCA GGT TCT ATT AGT AGC GGT     1968
Gly Ile Ser Glu Gln Pro Leu Phe Gly Ala Gly Ser Ile Ser Ser Gly
            645                 650                 655

GAA CTT TAT ATA GAT AAA ATT GAA ATT ATT CTA GCA GAT GCA ACA TTT     2016
Glu Leu Tyr Ile Asp Lys Ile Glu Ile Ile Leu Ala Asp Ala Thr Phe
            660                 665                 670

GAA GCA GAA TCT GAT TTA GAA AGA GCA CAA AAG GCG GTG AAT GCC CTG     2064
Glu Ala Glu Ser Asp Leu Glu Arg Ala Gln Lys Ala Val Asn Ala Leu
            675                 680                 685

TTT ACT TCT TCC AAT CAA ATC GGG TTA AAA ACC GAT GTG ACG GAT TAT     2112
Phe Thr Ser Ser Asn Gln Ile Gly Leu Lys Thr Asp Val Thr Asp Tyr
            690                 695                 700

CAT ATT GAT CAA GTA TCC AAT TTA GTG GAT TGT TTA TCA GAT GAA TTT     2160
His Ile Asp Gln Val Ser Asn Leu Val Asp Cys Leu Ser Asp Glu Phe
705                 710                 715                 720

TGT CTG GAT GAA AAG CGA GAA TTG TCC GAG AAA GTC AAA CAT GCG AAG     2208
Cys Leu Asp Glu Lys Arg Glu Leu Ser Glu Lys Val Lys His Ala Lys
            725                 730                 735
```

```
CGA CTC AGT GAT GAG CGG AAT TTA CTT CAA GAT CCA AAC TTC AGA GGG    2256
Arg Leu Ser Asp Glu Arg Asn Leu Leu Gln Asp Pro Asn Phe Arg Gly
            740                 745                 750

ATC AAT AGA CAA CCA GAC CGT GGC TGG AGA GGA AGT ACA GAT ATT ACC    2304
Ile Asn Arg Gln Pro Asp Arg Gly Trp Arg Gly Ser Thr Asp Ile Thr
            755                 760                 765

ATC CAA GGA GGA GAT GAC GTA TTC AAA GAG AAT TAC GTC ACA CTA CCG    2352
Ile Gln Gly Gly Asp Asp Val Phe Lys Glu Asn Tyr Val Thr Leu Pro
            770                 775                 780

GGT ACC GTT GAT GAG TGC TAT CCA ACG TAT TTA TAT CAG AAA ATA GAT    2400
Gly Thr Val Asp Glu Cys Tyr Pro Thr Tyr Leu Tyr Gln Lys Ile Asp
785                 790                 795                 800

GAG TCG AAA TTA AAA GCT TAT ACC CGT TAT GAA TTA AGA GGG TAT ATC    2448
Glu Ser Lys Leu Lys Ala Tyr Thr Arg Tyr Glu Leu Arg Gly Tyr Ile
                805                 810                 815

GAA GAT AGT CAA GAC TTA GAA ATC TAT TTG ATC CGT TAC AAT GCA AAA    2496
Glu Asp Ser Gln Asp Leu Glu Ile Tyr Leu Ile Arg Tyr Asn Ala Lys
            820                 825                 830

CAC GAA ATA GTA AAT GTG CCA GGC ACG GGT TCC TTA TGG CCG CTT TCA    2544
His Glu Ile Val Asn Val Pro Gly Thr Gly Ser Leu Trp Pro Leu Ser
            835                 840                 845

GCC CAA AGT CCA ATC GGA AAG TGT GGA GAA CCG AAT CGA TGC GCG CCA    2592
Ala Gln Ser Pro Ile Gly Lys Cys Gly Glu Pro Asn Arg Cys Ala Pro
850                 855                 860

CAC CTT GAA TGG AAT CCT GAT CTA GAT TGT TCC TGC AGA GAC GGG GAA    2640
His Leu Glu Trp Asn Pro Asp Leu Asp Cys Ser Cys Arg Asp Gly Glu
865                 870                 875                 880

AAA TGT GCA CAT CAT TCC CAT CAT TTC ACC TTG GAT ATT GAT GTT GGA    2688
Lys Cys Ala His His Ser His His Phe Thr Leu Asp Ile Asp Val Gly
                885                 890                 895

TGT ACA GAC TTA AAT GAG GAC TTA GGT GTA TGG GTG ATA TTC AAG ATT    2736
Cys Thr Asp Leu Asn Glu Asp Leu Gly Val Trp Val Ile Phe Lys Ile
            900                 905                 910

AAG ACG CAA GAT GGC CAT GCA AGA CTA GGG AAT CTA GAG TTT CTC GAA    2784
Lys Thr Gln Asp Gly His Ala Arg Leu Gly Asn Leu Glu Phe Leu Glu
            915                 920                 925

GAG AAA CCA TTA TTA GGG GAA GCA CTA GCT CGT GTG AAA AGA GCG GAG    2832
Glu Lys Pro Leu Leu Gly Glu Ala Leu Ala Arg Val Lys Arg Ala Glu
930                 935                 940

AAG AAG TGG AGA GAC AAA CGA GAG AAA CTG CAG TTG GAA ACA AAT ATT    2880
Lys Lys Trp Arg Asp Lys Arg Glu Lys Leu Gln Leu Glu Thr Asn Ile
945                 950                 955                 960

GTT TAT AAA GAG GCA AAA GAA TCT GTA GAT GCT TTA TTT GTA AAC TCT    2928
Val Tyr Lys Glu Ala Lys Glu Ser Val Asp Ala Leu Phe Val Asn Ser
                965                 970                 975

CAA TAT GAT AGA TTA CAA GTG GAT ACG AAC ATC GCG ATG ATT CAT GCG    2976
Gln Tyr Asp Arg Leu Gln Val Asp Thr Asn Ile Ala Met Ile His Ala
            980                 985                 990

GCA GAT AAA CGC GTT CAT AGA ATC CGG GAA GCG TAT CTG CCA GAG TTG    3024
Ala Asp Lys Arg Val His Arg Ile Arg Glu Ala Tyr Leu Pro Glu Leu
            995                 1000                1005

TCT GTG ATT CCA GGT GTC AAT GCG GCC ATT TTC GAA GAA TTA GAG GGA    3072
Ser Val Ile Pro Gly Val Asn Ala Ala Ile Phe Glu Glu Leu Glu Gly
            1010                1015                1020

CGT ATT TTT ACA GCG TAT TCC TTA TAT GAT GCG AGA AAT GTC ATT AAA    3120
Arg Ile Phe Thr Ala Tyr Ser Leu Tyr Asp Ala Arg Asn Val Ile Lys
1025                1030                1035                1040

AAT GGC GAT TTC AAT AAT GGC TTA TTA TGC TGG AAC GTG AAA GGT CAT    3168
Asn Gly Asp Phe Asn Asn Gly Leu Leu Cys Trp Asn Val Lys Gly His
```

```
                    1045                1050                1055
GTA GAT GTA GAA GAG CAA AAC AAC CAC CGT TCG GTC CTT GTT ATC CCA    3216
Val Asp Val Glu Glu Gln Asn Asn His Arg Ser Val Leu Val Ile Pro
            1060                1065                1070

GAA TGG GAG GCA GAA GTG TCA CAA GAG GTT CGT GTC TGT CCA GGT CGT    3264
Glu Trp Glu Ala Glu Val Ser Gln Glu Val Arg Val Cys Pro Gly Arg
            1075                1080                1085

GGC TAT ATC CTT CGT GTC ACA GCA TAT AAA GAG GGA TAT GGA GAG GGC    3312
Gly Tyr Ile Leu Arg Val Thr Ala Tyr Lys Glu Gly Tyr Gly Glu Gly
            1090                1095                1100

TGC GTA ACG ATC CAT GAG ATC GAA GAC AAT ACA GAC GAA CTG AAA TTC    3360
Cys Val Thr Ile His Glu Ile Glu Asp Asn Thr Asp Glu Leu Lys Phe
1105                1110                1115                1120

AGC AAC TGT GTA GAA GAG GAA GTA TAT CCA AAC AAC ACA GTA ACG TGT    3408
Ser Asn Cys Val Glu Glu Glu Val Tyr Pro Asn Asn Thr Val Thr Cys
            1125                1130                1135

AAT AAT TAT ACT GGG ACT CAA GAA GAA TAT GAG GGT ACG TAC ACT TCT    3456
Asn Asn Tyr Thr Gly Thr Gln Glu Glu Tyr Glu Gly Thr Tyr Thr Ser
            1140                1145                1150

CGT AAT CAA GGA TAT GAC GAA GCC TAT GGT AAT AAC CCT TCC GTA CCA    3504
Arg Asn Gln Gly Tyr Asp Glu Ala Tyr Gly Asn Asn Pro Ser Val Pro
            1155                1160                1165

GCT GAT TAC GCT TCA GTC TAT GAA GAA AAA TCG TAT ACA GAT GGA CGA    3552
Ala Asp Tyr Ala Ser Val Tyr Glu Glu Lys Ser Tyr Thr Asp Gly Arg
            1170                1175                1180

AGA GAG AAT CCT TGT GAA TCT AAC AGA GGC TAT GGG GAT TAC ACA CCA    3600
Arg Glu Asn Pro Cys Glu Ser Asn Arg Gly Tyr Gly Asp Tyr Thr Pro
1185                1190                1195                1200

CTA CCG GCT GGT TAT GTA ACA AAG GAT TTA GAG TAC TTC CCA GAG ACC    3648
Leu Pro Ala Gly Tyr Val Thr Lys Asp Leu Glu Tyr Phe Pro Glu Thr
            1205                1210                1215

GAT AAG GTA TGG ATT GAG ATC GGA GAA ACA GAA GGA ACA TTC ATC GTG    3696
Asp Lys Val Trp Ile Glu Ile Gly Glu Thr Glu Gly Thr Phe Ile Val
            1220                1225                1230

GAT AGC GTG GAA TTA CTC CTT ATG GAG GAA                            3726
Asp Ser Val Glu Leu Leu Leu Met Glu Glu
            1235                1240

(2) INFORMATION FOR SEQ ID NO:12:

(i) SEQUENCE CHARACTERISTICS:
        (A) LENGTH: 1242 amino acids
        (B) TYPE: amino acid
        (D) TOPOLOGY: linear (ii) MOLECULE TYPE: protein (xi) SEQUENCE DESCRIPTION: SEQ ID NO:12:

Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
                20                  25                  30

Ser Ala Leu Asn Leu Asn Ser Cys Gln Asn Ser Ser Ile Leu Asn Trp
            35                  40                  45

Ile Asn Ile Ile Gly Asp Ala Ala Lys Glu Ala Val Ser Ile Gly Thr
        50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95
```

```
Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
            115                 120                 125

Ser Val Leu Leu Tyr Arg Asn Tyr Leu Glu Ala Leu Asp Ser Trp Asn
130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Leu Arg Asp Ala
            195                 200                 205

Thr Arg Tyr Gly Thr Asn Trp Gly Leu Tyr Asn Ala Thr Pro Phe Ile
            210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
            275                 280                 285

Thr Asn Tyr Pro Ile Glu Thr Asp Phe Gln Leu Ser Arg Val Ile Tyr
            290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
            355                 360                 365

Val Trp Tyr Gly Ser Arg Asp Arg Ile Ser Pro Ala Asn Ser Gln Phe
            370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
            435                 440                 445

Ile Asp Asn Pro Arg Val Gln Asn Ile Asn Thr Tyr Leu Pro Gly Glu
            450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510
```

-continued

```
Asn Thr Ile Asn Pro Asp Arg Ile Thr Gln Ile Pro Leu Val Lys Gly
        515                 520                 525

Phe Arg Val Trp Gly Gly Thr Ser Val Ile Thr Gly Pro Gly Phe Thr
    530                 535                 540

Gly Gly Asp Ile Leu Arg Arg Asn Thr Phe Gly Asp Phe Val Ser Leu
545                 550                 555                 560

Gln Val Asn Ile Asn Ser Pro Ile Thr Gln Arg Tyr Arg Leu Arg Phe
                565                 570                 575

Arg Tyr Ala Ser Ser Arg Asp Ala Arg Val Ile Val Leu Thr Gly Ala
            580                 585                 590

Ala Ser Thr Gly Val Gly Gly Gln Val Ser Val Asn Met Pro Leu Gln
        595                 600                 605

Lys Thr Met Glu Ile Gly Glu Asn Leu Thr Ser Arg Thr Phe Arg Tyr
    610                 615                 620

Thr Asp Phe Ser Asn Pro Phe Ser Phe Arg Ala Asn Pro Asp Ile Ile
625                 630                 635                 640

Gly Ile Ser Glu Gln Pro Leu Phe Gly Ala Gly Ser Ile Ser Ser Gly
                645                 650                 655

Glu Leu Tyr Ile Asp Lys Ile Glu Ile Ile Leu Ala Asp Ala Thr Phe
            660                 665                 670

Glu Ala Glu Ser Asp Leu Glu Arg Ala Gln Lys Ala Val Asn Ala Leu
        675                 680                 685

Phe Thr Ser Ser Asn Gln Ile Gly Leu Lys Thr Asp Val Thr Asp Tyr
    690                 695                 700

His Ile Asp Gln Val Ser Asn Leu Val Asp Cys Leu Ser Asp Glu Phe
705                 710                 715                 720

Cys Leu Asp Glu Lys Arg Glu Leu Ser Glu Lys Val Lys His Ala Lys
                725                 730                 735

Arg Leu Ser Asp Glu Arg Asn Leu Leu Gln Asp Pro Asn Phe Arg Gly
            740                 745                 750

Ile Asn Arg Gln Pro Asp Arg Gly Trp Arg Gly Ser Thr Asp Ile Thr
        755                 760                 765

Ile Gln Gly Gly Asp Asp Val Phe Lys Glu Asn Tyr Val Thr Leu Pro
    770                 775                 780

Gly Thr Val Asp Glu Cys Tyr Pro Thr Tyr Leu Tyr Gln Lys Ile Asp
785                 790                 795                 800

Glu Ser Lys Leu Lys Ala Tyr Thr Arg Tyr Glu Leu Arg Gly Tyr Ile
                805                 810                 815

Glu Asp Ser Gln Asp Leu Glu Ile Tyr Leu Ile Arg Tyr Asn Ala Lys
            820                 825                 830

His Glu Ile Val Asn Val Pro Gly Thr Gly Ser Leu Trp Pro Leu Ser
        835                 840                 845

Ala Gln Ser Pro Ile Gly Lys Cys Gly Glu Pro Asn Arg Cys Ala Pro
    850                 855                 860

His Leu Glu Trp Asn Pro Asp Leu Asp Cys Ser Cys Arg Asp Gly Glu
865                 870                 875                 880

Lys Cys Ala His His Ser His His Phe Thr Leu Asp Ile Asp Val Gly
                885                 890                 895

Cys Thr Asp Leu Asn Glu Asp Leu Gly Val Trp Val Ile Phe Lys Ile
            900                 905                 910

Lys Thr Gln Asp Gly His Ala Arg Leu Gly Asn Leu Glu Phe Leu Glu
        915                 920                 925

Glu Lys Pro Leu Leu Gly Glu Ala Leu Ala Arg Val Lys Arg Ala Glu
```

930                935                940

Lys Lys Trp Arg Asp Lys Arg Glu Lys Leu Gln Leu Glu Thr Asn Ile
945                950                955                960

Val Tyr Lys Glu Ala Lys Glu Ser Val Asp Ala Leu Phe Val Asn Ser
                965                970                975

Gln Tyr Asp Arg Leu Gln Val Asp Thr Asn Ile Ala Met Ile His Ala
                980                985                990

Ala Asp Lys Arg Val His Arg Ile Arg Glu Ala Tyr Leu Pro Glu Leu
                995                1000                1005

Ser Val Ile Pro Gly Val Asn Ala Ala Ile Phe Glu Glu Leu Glu Gly
                1010                1015                1020

Arg Ile Phe Thr Ala Tyr Ser Leu Tyr Asp Ala Arg Asn Val Ile Lys
1025                1030                1035                1040

Asn Gly Asp Phe Asn Asn Gly Leu Leu Cys Trp Asn Val Lys Gly His
                1045                1050                1055

Val Asp Val Glu Glu Gln Asn Asn His Arg Ser Val Leu Val Ile Pro
                1060                1065                1070

Glu Trp Glu Ala Glu Val Ser Gln Glu Val Arg Val Cys Pro Gly Arg
                1075                1080                1085

Gly Tyr Ile Leu Arg Val Thr Ala Tyr Lys Glu Gly Tyr Gly Glu Gly
                1090                1095                1100

Cys Val Thr Ile His Glu Ile Glu Asp Asn Thr Asp Glu Leu Lys Phe
1105                1110                1115                1120

Ser Asn Cys Val Glu Glu Val Tyr Pro Asn Asn Thr Val Thr Cys
                1125                1130                1135

Asn Asn Tyr Thr Gly Thr Gln Glu Glu Tyr Glu Gly Thr Tyr Thr Ser
                1140                1145                1150

Arg Asn Gln Gly Tyr Asp Glu Ala Tyr Gly Asn Asn Pro Ser Val Pro
                1155                1160                1165

Ala Asp Tyr Ala Ser Val Tyr Glu Glu Lys Ser Tyr Thr Asp Gly Arg
                1170                1175                1180

Arg Glu Asn Pro Cys Glu Ser Asn Arg Gly Tyr Gly Asp Tyr Thr Pro
1185                1190                1195                1200

Leu Pro Ala Gly Tyr Val Thr Lys Asp Leu Glu Tyr Phe Pro Glu Thr
                1205                1210                1215

Asp Lys Val Trp Ile Glu Ile Gly Glu Thr Glu Gly Thr Phe Ile Val
                1220                1225                1230

Asp Ser Val Glu Leu Leu Leu Met Glu Glu
                1235                1240

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "BglII site downstream of
            translation termination codon of CryIC."

(xi) SEQUENCE DESCRIPTION: SEQ ID NO:13:

ATAAGATCTG TT                                                        12

(2) INFORMATION FOR SEQ ID NO:14:

-continued

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

GCTAGCCATG GATCAAAATA AACACGGAAT TATTG                                35

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

CTGGTCAGAT CTTTGAAGTA GAGCTCC                                          27
```